(12) United States Patent
Pickkers et al.

(10) Patent No.: US 12,178,857 B2
(45) Date of Patent: Dec. 31, 2024

(54) RECOMBINANT ALKALINE PHOSPHATASE FOR USE IN TREATING SEPSIS-ASSOCIATED ACUTE KIDNEY INJURY

(71) Applicant: AM-Pharma B.V., Utrecht (NL)

(72) Inventors: Roelof Peter Pickkers, Utrecht (NL); Ravindra Lall Mehta, Utrecht (NL); Patrick Thomas Murray, Utrecht (NL); Michael Joannidis, Utrecht (NL); Erik Jan Van Den Berg, Utrecht (NL); Jacques Salomon Robert Arend, Utrecht (NL)

(73) Assignee: AM-Pharma B.V., Utrecht (NL)

(*) Notice: Subject to any disclaimer, the term of this patent is extended or adjusted under 35 U.S.C. 154(b) by 681 days.

(21) Appl. No.: 16/979,117

(22) PCT Filed: Mar. 8, 2019

(86) PCT No.: PCT/NL2019/050153
§ 371 (c)(1),
(2) Date: Sep. 8, 2020

(87) PCT Pub. No.: WO2019/172766
PCT Pub. Date: Sep. 12, 2019

(65) Prior Publication Data
US 2020/0397870 A1   Dec. 24, 2020

Related U.S. Application Data

(60) Provisional application No. 62/640,494, filed on Mar. 8, 2018.

(51) Int. Cl.
*A61K 38/46* (2006.01)
*A61K 9/00* (2006.01)
*A61P 13/12* (2006.01)

(52) U.S. Cl.
CPC .......... *A61K 38/465* (2013.01); *A61K 9/0019* (2013.01); *A61P 13/12* (2018.01); *C12Y 301/03001* (2013.01)

(58) Field of Classification Search
CPC .......... A61K 38/465; C12Y 301/03001; A61P 13/12
See application file for complete search history.

(56) References Cited

U.S. PATENT DOCUMENTS

| 8,557,545 B2 | 10/2013 | Velders et al. |
| 8,586,032 B2 | 11/2013 | Pickkers et al. |

(Continued)

FOREIGN PATENT DOCUMENTS

| WO | WO-2015160805 A1 | 10/2015 |
| WO | WO-2019172766 A1 | 9/2019 |

OTHER PUBLICATIONS

Kiffer-Moreira, T., et al., "Catalytic Signature of a Heat-stable, Chimeric Human Alkaline Phosphatase With Therapeutic Potential," PLoS One 9(2):e89374, Public Library of Science, United States (2014). (Year: 2014).*

(Continued)

*Primary Examiner* — Gary B Nickol
*Assistant Examiner* — Amelia Nicole Dickens
(74) *Attorney, Agent, or Firm* — Sterne, Kessler, Goldstein & Fox P.L.L.C.

(57) ABSTRACT

The present disclosure relates to the use of alkaline phosphatases, and in particular improved alkaline phosphatases such as RecAP, for the prevention, treatment, cure, or amelioration of the symptoms of acute kidney injury caused, e.g., by sepsis. The application relates to methods of preserving renal function renal function, shortening the duration of renal replacement therapy, increasing the creatinine clearance, decreasing the risk of death in subjects with (Continued)

sepsis-associate acute kidney injury (SA-AKI) or at risk of SA-AKI.

13 Claims, 37 Drawing Sheets

Specification includes a Sequence Listing.

(56) References Cited

U.S. PATENT DOCUMENTS

| | | | |
|---|---|---|---|
| 2014/0193388 A1 | 7/2014 | Velders et al. | |
| 2014/0219984 A1* | 8/2014 | Arend | G01N 33/49 424/94.6 |
| 2016/0250299 A1 | 9/2016 | Arend et al. | |
| 2017/0009216 A1* | 1/2017 | Raaben | C12Y 301/03001 |

OTHER PUBLICATIONS

Peters, E., et al., "Alkaline Phosphatase Protects Against Renal Inflammation Through Dephosphorylation of Lipopolysaccharide and Adenosine Triphosphate," British Journal of Pharmacology 172(20):4932-4945, Wiley, United Kingdom (2015). (Year: 2015).*

Peters, E., et al., "Study Protocol For A Multicentre Randomised Controlled Trial: Safety, Tolerability, Efficacy and Quality of Life Of A Human Recombinant Alkaline Phosphatase in Patients With Sepsis-Associated Acute Kidney Injury (STOP-AKI)," Bmj Open 6(9):e012371. (2016). (Year: 2016).*

Pikkers et al. "Study protocol of a randomised, double-blind, placebo-controlled, two-arm parallel-group, multi-centre phase 3 pivotal trial to investigate the efficacy and safety of recombinant human alkaline phosphatase . . . ", 2023, BMJ Open, ;13:e065613, p. 1-8. (Year: 2023).*

"Ilofotase Alfa" article from Global Substance Registration System—GSRS, last edited May 25, 2024, accessed Aug. 12, 2024 at gsrs.ncats.nih.gov/ginas/app/beta/substances/9N4Y2R43OM (Year: 2024).*

Bellomo, R., et al., "Acute Kidney Injury," Lancet 380(9843):756-766, Elsevier Ltd., United Kingdom (2012).

Billings, F.T and Shaw, A.D., "Clinical Trial Endpoints In Acute Kidney Injury," Nephron Clinical Practice 127(1-4):89-93, S. Karger AG, Switzerland (2014).

Bone, R.C., et al., "Definitions for Sepsis and Organ Failure and Guidelines for the Use of Innovative Therapies in Sepsis. The ACCP/SCCM Consensus Conference Committee. American College of Chest Physicians/Society of Critical Care Medicine," Chest 101(6):1644-1655, American College of Chest Physicians, United States (Jun. 1992).

Bonventre, J.V., et al., "Cellular Pathophysiology of Ischemic Acute Kidney Injury," The Journal of Clinical Investigation 121(11):4210-4221, American Society for Clinical Investigation, United States (2011).

Chawla, L.S., et al., "The Severity of Acute Kidney Injury Predicts Progression to Chronic Kidney Disease," Kidney International 79(12):1361-1369, Elsevier Inc., United States (2011).

Gomez, H., et al., "A Unified Theory of Sepsis-Induced Acute Kidney Injury: Inflammation, Microcirculatory Dysfunction, Bioenergetics, and The Tubular Cell Adaptation To Injury," Shock 41(1):3-11, Lippincott Williams & Wilkins, United States (2014).

Heemskerk, S., et al., "Alkaline Phosphatase Treatment Improves Renal Function in Severe Sepsis or Septic Shock Patients," Critical Care Medicine 37(2):417-423, Lippincott Williams & Wilkins, United States (2009).

Hoste, E.A.J., et al., "RIFLE Criteria for Acute Kidney Injury are Associated With Hospital Mortality in Critically Ill Patients: A Cohort Analysis," Critical care 10(3):R73, BioMed Central Ltd., United Kingdom (2006).

Hoste, E.A.J., et al., "Epidemiology of Acute Kidney Injury In Critically Ill Patients: The Multinational AKI-EPI Study," Intensive Care Medicine 41(8):1411-1423, Springer International, United States (2015).

Joannidis, M., et al., "Prevention of Acute Kidney Injury And Protection of Renal Function In The Intensive Care Unit: Update 2017 : Expert Opinion of The Working Group on Prevention, AKI Section, European Society of Intensive Care Medicine," Intensive Care Medicine 43(6):730-749, Springer Verlag, Germany (2017).

Kellum, J. A., et al., "The Effects of Alternative Resuscitation Strategies on Acute Kidney Injury in Patients With Septic Shock," American Journal Of Respiratory And Critical Care Medicine 193(3):281-287, American Thoracic Society, United States (2016).

Kellum, J. A., et al., "Recovery After Acute Kidney Injury," American Journal of Respiratory and Critical Care Medicine 195(6):784-791, American Thoracic Society, United States (2017).

Kellum, J. A., et al., "Paradigms of Acute Kidney Injury in The Intensive Care Setting," Nature Reviews Nephrology 14(4):217-230, Wiley-Blackwell Publishing Ltd., United Kingdom (2018).

Khundmiri, S. J., et al., "Effect of Reversible and Irreversible Ischemia on Marker Enzymes of BBM From Renal Cortical PT Subpopulations," The American Journal Of Physiology 273(6):F849-F856, American Physiological Society, United States (1997).

Kiffer-Moreira, T., et al., "Catalytic Signature of a Heat-stable, Chimeric Human Alkaline Phosphatase With Therapeutic Potential," PLoS One 9(2):e89374, Public Library of Science, United States (2014).

Levy, M., et al., "2001 SCCM/ESICM/ACCP/ATS/SIS International Sepsis Definitions Conference," Critical care medicine 31(4):1250-1256, Lippincott Williams & Wilkins, United States (2003).

Mehta, R.L., et al., "Acute Kidney Injury Network: Report of an Initiative to Improve Outcomes in Acute Kidney Injury," Critical Care 11(2): R31, BioMed Central Ltd, United Kingdom (2007).

Nisula, S., et al., "Incidence, Risk Factors and 90-Day Mortality of Patients With Acute Kidney Injury in Finnish Intensive Care Units: The FINNAKI Study," Intensive Care Medicine 39(3):420-428, Springer Verlag, Germany (2013).

Okusa, M.D., et al., "Reading Between The (guide)lines—The KDIGO Practice Guideline on Acute Kidney Injury in The Individual Patient," Kidney International 85(1):39-48, Elsevier Inc., United States (2014).

Oppert, M., et al., "Acute Renal Failure In Patients with Severe Sepsis and Septic Shock—A Significant Independent Risk Factor for Mortality: Results From The German Prevalence Study," European Dialysis and Transplant Association 23(3):904-909, Oxford University Press, United Kingdom (2008).

Perrone, R.D., et al., "Serum Creatinine as an Index of Renal Function: New Insights Into Old Concepts," Clinical chemistry 38(10):1933-1953, Oxford University Press, United Kingdom (Nov. 1992).

Peters, E., et al., "Alkaline Phosphatase Protects Against Renal Inflammation Through Dephosphorylation of Lipopolysaccharide and Adenosine Triphosphate," British Journal of Pharmacology 172(20):4932-4945, Wiley, United Kingdom (2015).

Peters, E., et al., "Study Protocol For A Multicentre Randomised Controlled Trial: Safety, Tolerability, Efficacy and Quality of Life Of A Human Recombinant Alkaline Phosphatase in Patients With Sepsis-Associated Acute Kidney Injury (STOP-AKI)," BMJ Open 6(9):e012371, BMJ Publishing Group Ltd, United Kingdom (2016).

Peters, E., et al., "Pharmacokinetic Modeling and Dose Selection in a Randomized, Double-Blind, Placebo-Controlled Trial of a Human Recombinant Alkaline Phosphatase in Healthy Volunteers," *Clinical Pharmacokinetics*, 55(10): 1227-1237, Springer Nature, Netherlands (2016).

Pickkers, P., et al., "Alkaline Phosphatase for Treatment of Sepsis-induced Acute Kidney Injury: a Prospective Randomized Double-blind Placebo-controlled Trial," Critical Care 16(1):R14, BioMed Central Ltd, United Kingdom (2012).

Poelstra, K., et al., "Dephosphorylation of Endotoxin by Alkaline Phosphatase in Vivo," American Journal of Pathology 151(4):1163-1169, Elsevier, United States (1997).

Shemesh, O., et al., "Limitations of Creatinine as a Filtration Marker in Glomerulopathic Patients," Kidney International 28(5):830-838, Elsevier, United States (1985).

Vaara, S.T., et al., "Fluid Overload Is Associated With An Increased Risk for 90-Day Mortality In Critically Ill Patients With Renal

(56) References Cited

OTHER PUBLICATIONS

Replacement Therapy: Data From The Prospective FINNAKI Study," Critical care 16(5):R197, BioMed Central Ltd, United Kingdom (2012).

Verweij, W. R., et al., "Protection Against an Escherichia Coli-induced Sepsis by Alkaline Phosphatase in Mice," Shock 22(2):174-179, Lippincott Williams & Wilkins, United States (2004).

Vincent, J. L., et al., "Sepsis in European Intensive Care Units: Results of The SOAP Study, " Critical care medicine 34(2):344-353, Lippincott Williams & Wilkins, United States (2006).

International Search Report and Written Opinion for International Application No. PCT/NL2019/050153, European Patent Office, Netherlands, mailed on Jul. 30, 2019, 10 pages.

Doi, K., et al., "CQ3-4: What should be assessed as risk factors for AKI development in sepsis?" in The Japanese Clinical Practice Guideline for Acute Kidney Injury 2016 with English Translation, The Scientific Academy Committee of Japanese Society for Dialysis Therapy, Japan (2016).

Yanai, M., "Measurement of glomerular filtration rate and its estimation equation," Mod. Media 59(6):155-160, Division of General Medicine, Department of Internal Medicine, Nihon University School of Medicine, Tokyo, Japan (2013).

Pickkers, P., et al., "Effect of Human Recombinant Alkaline Phosphatase on 7-Day Creatinine Clearance in Patients With Sepsis-Associated Acute Kidney Injury: A Randomized Clinical Trial," *JAMA* 320(19):1998-2009, American Medical Association, United States (Nov. 2018).

Peters, E., et al., "Alkaline Phosphatase as a Treatment of Sepsis-Associated Acute Kidney Injury," *Journal of Pharmacology and Experimental Therapeutics* 344(1):2-7, The American Society for Pharmacology and Experimental Therapeutics, United States (Jan. 2013).

Peters, E., et al., "The Potential of Alkaline Phosphatase as a Treatment for Sepsis-Associated Acute Kidney Injury," *Nephron Clinical Practice* 127(1-4):144-148, S. Karger AG, Switzerland (Sep. 2014).

Peters, E., et al., "Biodistribution and translational pharmacokinetic modeling of a human recombinant alkaline phosphatase," *International Journal of Pharmaceutics* 495(1):122-131, Elsevier, Netherlands (published online Sep. 2015, published in print Nov. 2015).

Peters, E., et al., "Effects of a human recombinant alkaline phosphatase on renal hemodynamics, oxygenation and inflammation in two models of acute kidney injury," *Toxicology and Applied Pharmacology* 313:88-96, Elsevier, Netherlands (published online Oct. 2016, published in print Dec. 2016).

Peters, E., et al., "Alkaline phosphatase: a possible treatment for sepsis-associated acute kidney injury in critically ill patients," *American Journal of Kidney Diseases* 63(6):1038-1048, National Kidney Foundation, United States (published online Jan. 2014, published in print Jun. 2014).

Tunjungputri, R. N., et al., "Human recombinant alkaline phosphatase inhibits ex vivo platelet activation in humans," *Thrombosis and Haemostasis* 116(6):1111-1121, Georg Thieme Verlag KG, Germany (published online Sep. 2016, published in print Nov. 2016).

Peters, E., et al., "Effects of a human recombinant alkaline phosphatase during impaired mitochondrial function in human renal proximal tubule epithelial cells," *European Journal of Pharmacology* 796:149-157, Elsevier, Netherlands (published online Dec. 2016, published in print Feb. 2017).

Mehta, R. L., "Timed and targeted therapy for acute kidney injury: a glimpse of the future," *Kidney International* 77(11):947-949, Elsevier for the International Society of Nephrology, Netherlands (Jun. 2010).

Wan, S.J., et al., "Diagnostic value of cystatin C in sepsis-associated acute kidney injury," Chin J Clinicians (Electronic Edition), 4(5):568-573, Chinese Medical Association, Chinese (May 2010).

\* cited by examiner

| Dose Group | AUC$_{0-inf}$ (h·U/L) Median [IQR] | Fold (over BiAP) | C$_{min}$ (U/L) Mean (SD) | Fold (over BiAP) | T$_{trough}$ (h) |
|---|---|---|---|---|---|
| 250 U/kg or 0.40 mg/kg qd × 3 | 45762 [26225-75202] | 2.29 | C$_{min1}$: 120 (74 - 187) C$_{min2}$: 183 (113 - 287) | 0.41 | t$_{trough1}$: 7.2 t$_{trough2}$: 35.0 t$_{trough3}$: 63.2 |
| 500 U/kg or 0.80 mg/kg qd × 3 | 90901 [50782-156914] | 4.55 | C$_{min1}$: 241 (140 - 391) C$_{min2}$: 369 (213 - 599) | 0.62 0.82 | t$_{trough1}$: 18.7 t$_{trough2}$: NR t$_{trough3}$: 92.1 |
| 1000 U/kg or 1.60 mg/kg qd × 3 | 184347 [102688-301544] | 9.22 | C$_{min1}$: 486 (288 - 742) C$_{min2}$: 746 (443 - 1136) | 1.26 1.66 2.54 | t$_{trough1}$: NR t$_{trough2}$: NR t$_{trough3}$: 144 |
| BiAP 67.5 U/kg (10 min) + 132.5 U/kg/24 h for 48 h | 20000 (estimated) | NA | 293 ± 257 ('trough') | NA | NA |

AUC$_{0-inf}$ denotes area under the concentration-time curve from zero to an infinite time, BiAP bovine intestinal alkaline phosphatase, C$_{min}$ observed minimum plasma or serum concentration after administration, NA not available, NR not recorded; qd every day (quaque die).
C$_{min}$ was determined just before re-infusion (C$_{min1}$ at t = 24 h; C$_{min2}$ at t = 48 h). Trough was set at 293 U/L T$_{trough}$ reflected the time to reach trough (t$_{trough1}$ after first infusion, t$_{trough2}$ after second infusion, etc).

Demographic and Baseline Disease Characteristics

| Characteristic | Placebo (N=116) | recAP 0.4 mg/kg (N=31) | recAP 0.8 mg/kg (N=32) | recAP 1.6 mg/kg (N=111) | Total (N=290) |
|---|---|---|---|---|---|
| Age, median [IQR] — years | 68.0 [61.0 - 75.0] | 67.0 [61.0 - 72.0] | 66.5 [62.5 - 72.0] | 65.0 [57.0 - 73.0] | 67.0 [59.0 - 73.0] |
| Male — no. (%) | 84 (72.4) | 23 (74.2) | 16 (50.0) | 82 (73.9) | 205 (70.7) |
| Caucasian — no. (%) | 95 (81.9) | 25 (80.6) | 27 (84.4) | 95 (85.6) | 242 (83.4) |
| Weight, median [IQR] — kg | 79.2 [70.0 - 86.5] | 78.0 [70.0 - 86.0] | 79.0 [72.0 - 90.0] | 80.0 [71.8 - 90.0] | 80.0 [70.0 - 89.1] |
| Height, median [IQR] — cm | 174.0 [165.0 - 178.0] | 172.5 [165.0 - 184.0] | 167.0 [160.0 - 174.0] | 173.0 [168.0 - 179.0] | 173.0 [165.0 - 178.5] |
| BMI, median [IQR] — kg/m² | 26.3 [23.9 - 29.4] | 25.8 [22.4 - 28.4] | 27.4 [25.2 - 30.7] | 26.8 [23.9 - 30.2] | 26.6 [23.9 - 29.4] |
| Disease severity | | | | | |
| APACHE II score, median [IQR] | 26.0 [20.0 - 33.5] | 30.0 [25.0 - 35.0] | 26.0 [20.0 - 34.5] | 25.0 [19.0 - 31.0] | 26.0 [21.0 - 33.0] |
| SAPS, median [IQR] | 47.0 [39.0 - 60.0] | 52.0 [42.0 - 70.0] | 50.5 [38.0 - 60.5] | 50.0 [42.0 - 61.0] | 49.5 [40.0 - 63.0] |
| SOFA score, median [IQR] | 10.0 [8.0 - 12.0] | 10.0 [8.0 - 13.0] | 9.0 [8.0 - 11.0] | 10.0 [8.0 - 12.0] | 10 [8.0 - 12.0] |
| Mechanical ventilation — no. (%) | 68 (58.6) | 23 (74.2) | 20 (62.5) | 70 (63.1) | 181 (62.4) |
| Vasopressor/inotropic therapy use — no. (%) | 103 (88.8) | 28 (90.3) | 30 (93.8) | 102 (91.9) | 263 (90.7) |
| Vital signs | | | | | |
| Heart rate, median [IQR] — beats/min | 98.0 [85.0 - 111.0] | 93.0 [77.0 - 115.0] | 90.0 [75.5 - 107.5] | 95.0 [83.0 - 110.0] | 95.5 [81.0 - 110.0] |
| Systolic blood pressure, median [IQR] — mm Hg | 112.0 [101.5 - 131.5] | 108.0 [100.0 - 119.0] | 118.5 [96.0 - 131.0] | 107.0 [95.0 - 119.0] | 110.0 [98.0 - 123.0] |
| Diastolic blood pressure, median [IQR] — mm Hg | 56.5 [51.0 - 63.5] | 54.0 [49.0 - 62.0] | 58.0 [54.0 - 62.0] | 55.0 [49.0 - 62.0] | 56.0 [50.0 - 62.0] |
| Body temperature — no. (%) | | | | | |
| <36°C | 11 (9.5) | 4 (12.9) | 5 (15.6) | 11 (9.9) | 31 (10.7) |
| ≥36°C to ≤38°C | 76 (65.5) | 20 (64.5) | 22 (68.8) | 79 (71.2) | 197 (67.9) |
| >38°C | 27 (23.3) | 7 (22.6) | 5 (15.6) | 18 (16.2) | 57 (19.7) |
| Renal function | | | | | |
| eGFR, median [IQR] — ml/min | 37.5 [23.9 - 50.8] | 27.2 [20.0 - 42.4] | 25.6 [20.4 - 40.7] | 29.7 [20.5 - 46.5] | 31.8 [21.0 - 47.8] |
| ECC, median [IQR; no.] — ml/min | | | | | |
| Day 0 | 31.8 [14.7 - 62.5; 49] | 14.4 [8.8 - 58.0; 10] | 26.0 [5.4 - 30.6; 12] | 24.1 [10.5 - 54.9; 46] | 27.9 [9.3 - 58.0; 117] |
| Day 1 | 35.9 [12.2 - 82.9; 103] | 28.3 [4.3 - 64.4; 30] | 25.2 [9.4 - 61.0; 31] | 26.0 [8.8 - 59.5; 102] | 29.4 [10.0 - 67.9, 266] |
| AKI stage — no. (%) | | | | | |
| Stage 1 | 91 (78.4) | 22 (71.0) | 23 (71.9) | 81 (73.0) | 217 (74.8) |
| Stage 2 | 16 (13.8) | 5 (16.1) | 5 (15.6) | 17 (15.3) | 43 (14.8) |
| Stage 3 | 5 (4.3) | 4 (12.9) | 4 (12.5) | 11 (9.9) | 24 (8.3) |
| Urine output, median [IQR] — ml/h | 60.0 [21.8 - 99.3] | 50.0 [21.7 - 101.7] | 27.4 [16.4 - 50.0] | 39.1 [10.9 - 85.7] | 46.3 [16.7 - 91.7] |
| Serum creatinine, median [IQR] — mg/dl | 1.8 [1.3 - 2.4] | 2.3 [1.5 - 2.8] | 1.9 [1.5 - 2.8] | 2.0 [1.4 - 2.8] | 1.9 [1.4 - 2.6] |

FIG. 5

Primary and Secondary Endpoints

| Endpoint | recAP 1.6 mg/kg | Placebo | Mean difference (Lower; Upper limit 95% CI) | P-value |
|---|---|---|---|---|
| Primary endpoint | | | | |
| Area under the time-corrected ECC curve (AUC₁₋₇), median [IQR] — ml/min | | | | |
| Part 1 | 60.7 [3.7–92.4] | 46.2 [21.5–114.6] | -16.5§§ (-62.6; 29.5) | 0.949 |
| Part 2 | 51.8 [17.6–94.6] | 44.5 [17.7–108.5] | -4.7§§ (-23.1; 13.8) | 0.691 |
| Part 1 + Part 2 | 55.1 [15.0–93.9] | 45.6 [17.7–112.4] | -7.8§§ (-7.4; 23.0) | 0.312 |
| Secondary endpoints | | | | |
| RRT incidence§ (days 1–28) — % | 36.0 | 29.3 | 1.4†† (0.8; 2.4) | 0.281 |
| RRT-free days (days 1–28), median [IQR] — days | 28 [16-28] | 28 [16-28] | 0.7§§ (1.8; 3.2) | 0.601 |
| Renal function, median [IQR] — ml/min | | | | |
| Day 28 (ECC/eGFR) | 88.0 [61.9 – 107.5] | 82.6 [53.8 – 104.8] | -3.9§§ (-23.7; 15.9) | 0.699 |
| Day 60 (eGFR) | 90.7 [75.8 – 108.9] | 88.6 [74.1 – 104.0] | -1.9§§ (-10.4; 6.6) | 0.658 |
| Day 90 (eGFR) | 91.1 [79.7 – 107.8] | 88.6 [72.1 – 101.3] | -2.0§§ (-10.2; 6.3) | 0.638 |
| Composite endpoints (MAKE) — no. (%) | | | | |
| MAKE 28* | 42.3 (47) | 41.4 (48) | 1.0†† (0.6; 1.6) | 0.883 |
| MAKE 60† | 27.0 (30) | 39.7 (46) | 1.8†† (1.0; 3.1) | 0.045 |
| MAKE 90‡ | 26.1 (29) | 39.7 (46) | 1.9†† (1.1; 3.3) | 0.031 |
| Non-renal clinical endpoints | | | | |
| Ventilator-free days (days 1–28), median [IQR] — days | 17 [1 – 23] | 14 [1 – 22] | 1.3§§ (-1.7; 4.3) | 0.396 |
| Shock-free days (days 1–28), median [IQR] — days | 23 [13 – 25] | 22 [1 – 25] | 1.8§§ (-1.0; 4.7) | 0.200 |
| ICU length of stay (days 1–90), median [IQR] — days | 13 [7 – 28] | 14 [6 – 28] | 1.0‡‡ (-0.8; 1.3) | 0.932 |
| Hospital length of stay (days 1–90), median [IQR] — days | 28 [22-28] | 28 [24-28] | 0.9‡‡ (-0.8; 1.3) | 0.908 |
| All-cause mortality at day 28 — no. (%) | 16 (14.4) | 31 (26.7) | 12.3 (1.9 – 22.7) | 0.022 |

FIG. 8

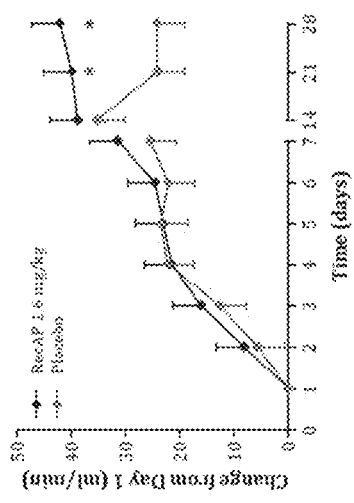
FIG. 9A Endogenous Creatinine Clearance
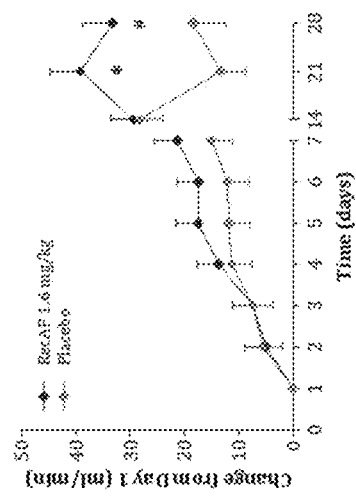
FIG. 9B BUN Clearance

PRIMARY AND SECONDARY ENDPOINTS FOR ALL GROUPS

| Endpoint | 1.6 mg/kg (n=111) | recAP 0.8 mg/kg (n=32) | 0.4 mg/kg (n=31) | Placebo (n=116) |
|---|---|---|---|---|
| Primary endpoint | | | | |
| Area under the time-corrected ECC curve (AUC1-7), median [IQR; no.] — ml/min | | | | |
| Part I | 60.72 [3.67 – 92.4; 28] | 63.54 [8.07 – 96.77; 32] | 46.95 [6.58 – 88.40; 30] | 46.16 [21.49 – 114.55; 29] |
| Part II | 51.76 [17.61 – 94.58; 80] | NA | NA | 44.51 [17.71 – 108.51; 77] |
| Part I + Part II | 55.06 [15.01 – 93.88; 108] | 63.54 [8.07 – 96.77; 32] | 46.95 [6.58 – 88.40; 30] | 45.58 [17.71 – 112.38; 106] |
| Secondary endpoints | | | | |
| RRT incidence§ (day 1-28) — % | 36.0 | 21.9 | 35.5 | 29.3 |
| RRT-free days (day 1-28), median [IQR; no.] - days | 28.0 [16.0 – 28.0; 111] | 28.0 [21.0 – 28.0; 32] | 28.0 [6.0 – 28.0; 31] | 28.0 [16.0 – 28.0; 116] |
| Renal function‖, median [IQR; no.] — ml/min | | | | |
| Day 28 (ECC/eGFR) | 88.0 [61.9 – 107.5; 73] | 84.96 [62.6 – 119.4; 21] | 89.63 [47.8 – 113.2; 18] | 82.64 [53.8 – 104.8; 59] |
| Day 60 (eGFR) | 90.7 [75.8 – 108.9; 92] | 87.14 [64.8 – 107.8; 26] | 92.07 [69.0-99.5; 22] | 88.62 [74.1 – 104.0; 81] |
| Day 90 (eGFR) | 91.1 [79.7 – 107.8; 92] | 90.03 [66.2 – 105.5; 26] | 89.46 [74.3 – 97.2; 22] | 88.62 [72.1 – 101.3; 81] |
| Composite endpoints (MAKE^) — no.(%) | | | | |
| MAKE 28* | 47 (42.3) | 9 (28.1) | 15 (48.4) | 48 (41.4) |
| MAKE 60† | 30 (27.0) | 11 (34.4) | 13 (41.9) | 46 (39.7) |
| MAKE 90‡ | 29 (26.1) | 10 (31.3) | 13 (41.9) | 46 (39.7) |
| Non-renal clinical endpoints | | | | |
| Ventilator-free days (days 1-28), median [IQR; no.] | 17.0 [1.0 – 23.0; 92] | 20.0 [3.0 – 25.0; 27] | 12.0 [2.0 – 22.0; 26] | 14.0 [1.0 – 22.0; 93] |
| Shock-free days (days1-28), median [IQR; no.] | 23.0 [13.0 – 25.0; 101] | 23.0 [15.0 – 26.0; 30] | 18.5 [4.0 – 25.5; 28] | 22.0 [1.0 – 25.0; 103] |
| ICU length of stay (days 1-90), median [IQR; no.] — days | 13.0 [7.0 – 28.0; 109] | 11.0 [5.5 – 28.0; 32] | 16.0 [6 – 28; 31] | 14.0 [6.0 – 28.0; 112] |
| Hospital length of stay (days 1-90), median [IQR; no.] — days | 28.0 [22.0-28.0; 109] | 28.0 [14.0 –28.5; 32] | 28.0 [21.0 – 28.0; 31] | 28.0 [23.5-28.0; 112] |
| All-cause mortality at day 28 — no.(%) | 16 (14.4) | 4 (12.5) | 8 (25.8) | 31 (26.7) |

AUC1-7 denotes area under the endogenous creatinine clearance (ECC) curve from day 1 through day 7, divided by 7 to provide a time-corrected clearance in ml/min.
CI indicates confidence interval, CKD-EPI Chronic Kidney Disease Epidemiology Collaboration, ECC endogenous creatinine clearance, eGFR estimated glomerular filtration rate, ICU intensive care unit, IQR interquartile range, MAKE major adverse kidney events, RRT renal-replacement therapy, and SOFA Sequential Organ Failure Assessment.
§ RRT incidence indicates the percentage of patients that needed RRT following randomisation.
‖ With last observation carried forward.
* MAKE 28: received RRT before or on day 28 or died before or on day 28. Proportion that met at least one of the criteria.
† MAKE 60: eGFR <60 ml/min at day 60 estimated by the CKD-EPI formula based on serum creatinine or required chronic RRT, before or on day 60 or died before or on day 60. Proportion that met at least one of the criteria.
‡ MAKE 90: 60: eGFR <60 ml/min at day 90 estimated by the CKD-EPI formula based on serum creatinine or required chronic RRT, before or on day 90 or hospitalization for new episode of AKI before or on day 90 or died before or on day 90. Proportion that met at least one of the criteria.

FIG. 12

| Parameter | Comparison | HR | lower CL | upper CL | p-value |
|---|---|---|---|---|---|
| Treatment arm | recAP 1.6 mg/kg vs placebo | 0.50 | 0.28 | 0.899 | 0.020 |
| SOFA Resp | (SOFA Resp + 1) vs SOFA Resp | 1.68 | 1.22 | 2.31 | 0.001 |
| SOFA CNS | (SOFA CNS + 1) vs SOFA CNS | 1.17 | 1.00 | 1.39 | 0.057 |
| SOFA Cardio | (SOFA Cardio + 1) vs SOFA Cardio | 1.52 | 1.01 | 2.28 | 0.044 |
| SOFA Liver | (SOFA Liver + 1) vs SOFA Liver | 1.08 | 0.79 | 1.47 | 0.636 |
| SOFA Coagulation | (SOFA Coag + 1) vs SOFA Coag | 1.37 | 1.03 | 1.81 | 0.030 |
| SOFA Renal | (SOFA Renal + 1) vs SOFA Renal | 1.15 | 0.88 | 1.51 | 0.306 |

CL denotes confidence limit, and HR hazard ratio

SOFA Resp: Respiratory system
SOFA CNS: Central Nervous system
SOFA Cardio: Cardiovascular system
SOFA Liver: Liver
SOFA Coag: Coagulation
SOFA Renal: Renal "SOFA Resp+1" indicates the increase in hazard ratio associated with an increase in the SOFA subgroup Respiratory of 1 point.

FIG. 14

TREATMENT-EMERGENT (SERIOUS) ADVERSE EVENTS

| Adverse event | Treatment emergent AEs | | | | Treatment emergent SAEs | | | |
|---|---|---|---|---|---|---|---|---|
| | Placebo (N=112) | recAP 0.4 mg (N=38) | recAP 0.8 mg (N=35) | 1.6 mg (N=109) | Placebo (N=112) | 0.4 mg (N=38) | recAP 0.8 mg (N=35) | 1.6 mg (N=109) |
| Total number of events | 898 | 277 | 252 | 898 | 89 | 34 | 19 | 76 |
| Number of patients with at least one treatment-emergent event | 111 (99.1) | 35 (92.1) | 31 (88.6) | 103 (94.5) | 56 (50.0) | 18 (47.4) | 11 (31.4) | 47 (43.1) |
| Gastrointestinal disorders | 49 (43.8) | 17 (44.7) | 16 (45.7) | 63 (57.8) | 6 (5.4) | 3 (7.9) | 2 (5.7) | 11 (10.1) |
| Infections and infestations | 47 (42.0) | 16 (42.1) | 16 (45.7) | 60 (55.0) | 18 (16.1) | 5 (13.2) | 5 (14.3) | 18 (16.5) |
| Metabolism and nutrition disorders | 41 (36.6) | 13 (34.2) | 13 (37.1) | 49 (45.0) | 1 (0.9) | 0 | 0 | 0 |
| General disorders and administration site conditions | 43 (38.4) | 10 (26.3) | 13 (37.1) | 44 (40.4) | 9 (8.0) | 2 (5.3) | 0 | 5 (4.6) |
| Cardiac disorders | 44 (39.3) | 11 (28.9) | 12 (34.3) | 43 (39.4) | 11 (9.8) | 0 | 3 (8.6) | 9 (8.3) |
| Psychiatric disorders | 39 (34.8) | 12 (31.6) | 13 (37.1) | 42 (38.5) | 0 | 0 | 0 | 1 (0.9) |
| Respiratory, thoracic and mediastinal disorders | 52 (46.4) | 14 (36.8) | 14 (40.0) | 40 (36.7) | 14 (12.5) | 6 (15.8) | 3 (8.6) | 9 (8.3) |
| Vascular disorders | 40 (35.7) | 12 (31.6) | 9 (25.7) | 36 (33.0) | 7 (6.3) | 1 (2.6) | 0 | 5 (4.6) |
| Investigations | 30 (26.8) | 8 (21.1) | 10 (28.6) | 30 (27.5) | 1 (0.9) | 0 | 0 | 1 (0.9) |
| Blood and lymphatic system disorders | 22 (19.6) | 10 (26.3) | 8 (22.9) | 24 (22.0) | 2 (1.8) | 2 (5.3) | 0 | 2 (1.8) |
| Skin and subcutaneous tissue disorders | 17 (15.2) | 7 (18.4) | 5 (14.3) | 22 (20.2) | 0 | 0 | 0 | 0 |
| Nervous system disorders | 15 (13.4) | 6 (15.8) | 10 (28.6) | 19 (17.4) | 1 (0.9) | 4 (10.5) | 1 (2.9) | 4 (3.7) |
| Renal and urinary disorders | 12 (10.7) | 6 (15.8) | 2 (5.7) | 16 (14.7) | 2 (1.8) | 1 (2.6) | 0 | 1 (0.9) |
| Injury, poisoning and procedural complications | 15 (13.4) | 13 (34.2) | 7 (20.0) | 14 (12.8) | 3 (2.7) | 3 (7.9) | 2 (5.7) | 0 |
| Musculoskeletal and connective tissue disorders | 14 (12.5) | 3 (7.9) | 1 (2.9) | 13 (11.9) | 1 (0.9) | 0 | 0 | 0 |
| Hepatobiliary disorders | 9 (8.0) | 1 (2.6) | 1 (2.9) | 9 (8.3) | 4 (3.6) | 1 (2.6) | 0 | 0 |
| Endocrine disorders | 4 (3.6) | 1 (2.6) | 1 (2.9) | 3 (2.8) | 0 | 0 | 0 | 0 |
| Eye disorders | 2 (1.8) | 3 (7.9) | 1 (2.9) | 3 (2.8) | 0 | 0 | 0 | 0 |
| Ear and labyrinth disorders | 1 (0.9) | 0 | 0 | 2 (1.8) | 0 | 0 | 0 | 0 |
| Neoplasm benign, malignant and unspecified (incl cyst and polyps) | 1 (0.9) | 0 | 0 | 1 (0.9) | 0 | 0 | 0 | 1 (0.9) |
| Congenital, familial and genetic disorders | 0 | 0 | 0 | 1 (0.9) | 0 | 0 | 0 | 0 |
| Reproductive system and breast disorders | 0 | 0 | 0 | 1 (0.9) | 0 | 0 | 0 | 0 |

Data presented as no. (%)

AE denotes adverse event. SAE denotes serious adverse event.

Treatment-emergent (serious) adverse events were coded according to the Medical Dictionary for Regulatory Activities. Patients were counted once for each event category event if they had multiple events in that category. There were no significant differences at P<0.05 between the groups in the percentage of patients with treatment-emergent (serious) adverse events.

FIG. 16

Cox model with ECC is highly significant
And comparable to Cox model with CKD Table:

| | Dependent variable: | |
|---|---|---|
| | OS | |
| | (1) | (2) |
| MeanBaseECC | −0.032*** | |
| | (0.007) | |
| CKD Severe-Mild | | −0.751*** |
| | | (0.274) |
| CKD Normal | | −2.435*** |
| | | (0.602) |
| Observations | 268 | 268 |
| $R^2$ | 0.144 | 0.109 |
| Log Likelihood | −298.534 | −303.956 |
| LR Test | 41.786*** (df = 1) | 30.941*** (df = 2) |
| Score (Logrank) Test | 18.734*** (df = 1) | 27.901*** (df = 2) |

Note: *$p<0.1$; $p<0.05$; *$p<0.01$

FIG. 18

Cox HR predictions for CKD group medians and cut-offs

| CKD | median | n | HR | seHR |
|---|---|---|---|---|
| Kidney failure | 5.46 | 87 | 3.79 | 28.6 |
| Severe-Mild | 31.2 | 109 | 1.64 | 10.6 |
| Normal | 97.3 | 72 | 0.192 | 35.3 |
| critLow | 15.0 | | 2.78 | 21.9 |
| critHigh | 60.0 | | 0.646 | 9.37 |

FIG. 20

RECOMBINANT ALKALINE PHOSPHATASE FOR USE IN TREATING SEPSIS-ASSOCIATED ACUTE KIDNEY INJURY

REFERENCE TO SEQUENCE LISTING SUBMITTED ELECTRONICALLY

The content of the electronically submitted sequence listing in ASCII text file (3151_0110001_Seqlisting_ST25; Size: 4,571 bytes; and Date of Creation: Oct. 3, 2023) filed with the application is incorporated herein.

BACKGROUND

The kidneys perform several functions in an animal body, such as excretion of waste, acid-base homeostasis, osmolality regulation, blood pressure regulation and hormone secretion. To enable the kidneys to perform these tasks, the kidneys receive, despite their relatively small size, approximately 20% of the cardiac output. Consequently a disruption of blood flow to the kidneys (renal blood flow, RBF) has a direct impact on many of the functions of the kidney. For instance, reduction of excretion of nitrogenous waste and disturbances of fluid and electrolyte balances could then occur. On the long term, reduced RBF, but also other toxic events, such as ischemia (reperfusion injury), use of contrast media or (other) nephrotoxic drugs, e.g. antibiotics, can be so stressful to the kidneys that it results in acute kidney injury (AKI).

Acute Kidney Injury (AKI) is observed in up to 60% of patients in intensive care units (ICUs), and its incidence is increasing (Hoste et al. Intensive Care Med 2015; 41:1411-23; Hoste et al. Critical Care; 10; Nisula et al. Intensive Care Med 2013; 39:420-8; Vincent et al. Critical Care Medicine 2006; 34:344-53). Development of AKI in sepsis patients is associated with an increased mortality (Kellum et al. Critical Care Medicine 2016; 193:281-7), while survivors are at risk of developing chronic kidney disease (Chawla et al. Kidney Int 2011; 79:1361-9; Oppert et al. Nephrol Dial Transplant 2008; 23:904-9; Vaara et al. Crit Care 2012; 16:R197) resulting in a tremendous burden for both patient and society.

It is very important to prevent and/or adequately treat AKI, because first, AKI is accompanied with high costs, morbidity and mortality, and second, prolonged AKI may lead to chronic kidney injury (CKI), possibly leading to irreversible loss of renal function. Additionally, an individual that has acquired CKI is more prone to (again) acquire AKI, which is then called "acute on chronic kidney injury". Because the renal function in CKI patients is already reduced, acute on chronic kidney injury may reduce renal function below a critical threshold.

BRIEF SUMMARY

The present disclosure provides methods to treat sepsis-associated acute kidney disease injury (SA-AKI) in a subject in need thereof comprising administering an effective amount of alkaline phosphatase (AP) to said subject, wherein (i) the subject has an ECC (endogenous creatinine clearance) rate ≤60 ml/min prior to the treatment with AP or an eGFR (estimated glomerular filtration rate) ≤60 ml/min prior to the treatment with AP, (ii) the AP is administered in at least one 500 U/kg to 2,000 U/kg dose, and (iii) the administration of the AP results in an increase in renal function.

In some aspects, the subject has moderate kidney injury (15-60 ml/min ECC) prior to treatment with AP. In some aspects, the subject has severe kidney injury (<15 ml/min ECC) prior to treatment with AP. In some aspects, the subject does not have mild kidney injury (>60 ml/min ECC) prior to treatment with AP. In some aspects, the subject has 15-60 ml/min eGFR prior to treatment with AP. In some aspects, the subject has <15 ml/min eGFR prior to treatment with AP. In some aspects, the subject does not have >60 ml/min eGFR prior to treatment with AP. In some aspects, the AP is a human AP. In some aspects, the AP is a recombinant AP. In some aspects, the recombinant AP is chimeric. In some aspects, the chimeric AP has at least 70%, at least 75%, at least 80%, at least 85%, at least 90%, at least 95%, at least 96%, at least 97%, at least 98%, at least 99% or 100% sequence identity to RecAP (SEQ ID NO: 1).

In some aspects, the increase in renal function comprises an increase in ECC with respect to ECC in the absence of treatment or an increase in eGFR with respect to eGFR in the absence of treatment. In some aspects, sepsis is detected less than 96 hours prior to AP administration. In some aspects, the sepsis is detected less than 72 hours prior to SA-AKI detection.

In some aspects, treatment in initiated within 24 hours after sepsis is detected. In some aspects, treatment is initiated within 24 hours after SA-AKI is detected. In some aspects, AP is administered once daily. In some aspects, AP is administered intravenously. In some aspects, AP is administered in three daily doses. In some aspects, the AP dose is 0.8 mg/kg or 1.6 mg/kg of RecAP, e.g., the clinical grade RecAP used in the present disclosure. In some aspects, the AP dose is 500 U/kg or 1000 U/kg of RecAP, e.g., the clinical grade RecAP used in the present disclosure.

In some aspects, the administration of at least one dose of AP results in a shortening of duration or cessation of renal replacement therapy (RRT) in a subject undergoing RRT. In some aspects, the administration of at least one dose of AP results in the preservation or increase of glomerular filtration rate (GFR) or eGFR in the subject.

BRIEF DESCRIPTION OF THE DRAWINGS/FIGURES

FIG. 1 is a table showing proposed RecAP dose groups.

FIG. 2 shows a RecAP amino acid sequence (SEQ ID NO: 1).

Figure 4:
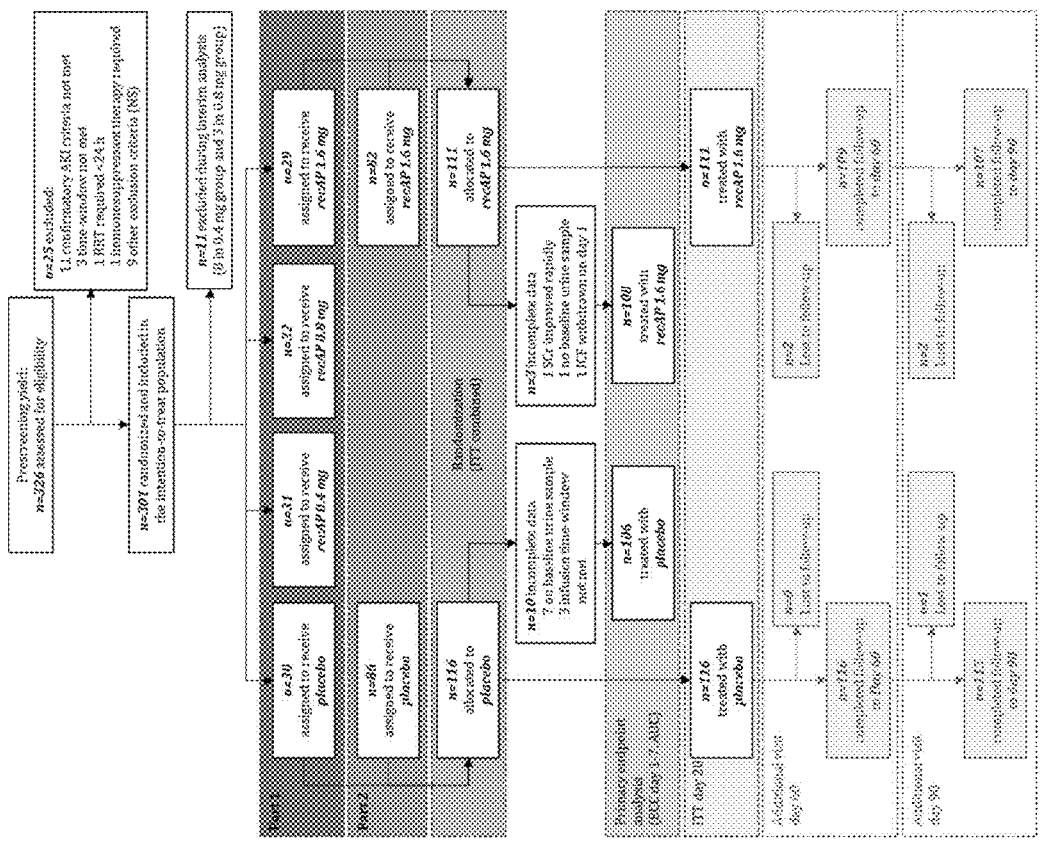

FIG. 4 is a flowchart showing the enrollment, randomization, and follow-up of the patients in the trial. Abbreviations: AKI (acute kidney injury), AUC (time-corrected area under the curve), ECC (endogenous creatinine clearance), ICF (informed consent form), ITT (intention-to-treat), IV (intravenous), MAKE (major adverse kidney events), NS (not specified), RecAP (human recombinant alkaline phosphatase having the sequence of SEQ ID NO: 1), RRT (renal-replacement therapy), SA-AKI (sepsis-associated acute kidney injury), SCr (serum creatinine).

FIG. 5 is a table presenting the demographic and baseline characteristics of all groups in the trial, showing that there were no significant differences between groups in any baseline characteristics. For variables with missing data, summary data are based on the adjusted number. Body-mass index (BMI) is the weight in kilograms divided by the square of the height in meters. Scores on the Acute Physiology and Chronic Health Evaluation II (APACHE II) range from 0-71, with higher scores indicating greater disease severity. Scores on the Sequential Organ Failure Assessment (SOFA) range from 0-24, with higher scores indicating more severe dysfunction. Scores on the Simplified Acute Physiology Score (SAPS) range from 0-163 with higher scores indicating greater disease severity. Estimated glomerular filtration rate (eGFR) was calculated according to the CKD-EPI (Chronic Kidney Disease Epidemiology Collaboration) equation: $141*\min(Scr/\kappa,1)\alpha*\max(Scr/\kappa,1)-1.209*0.993^{Age}*1.018$ [if female]*1.159 [if black]. Scr is serum creatinine (mg/dL), $\kappa$ is 0.7 for females and 0.9 for males, $\alpha$ is −0.329 for females and −0.411 for males, min indicates the minimum of Scr/κ or 1, and max indicates the maximum of Scr/κ or 1. (www.kidney.org/content/ckd-epi-creatinine-equation-2009). Acute Kidney Injury (AKI) stage was stratified according to the AKI-Network definition (www.akinet.org/akinstudies.php). Median and interquartile values, or number and percentages are depicted.

Figure 6:
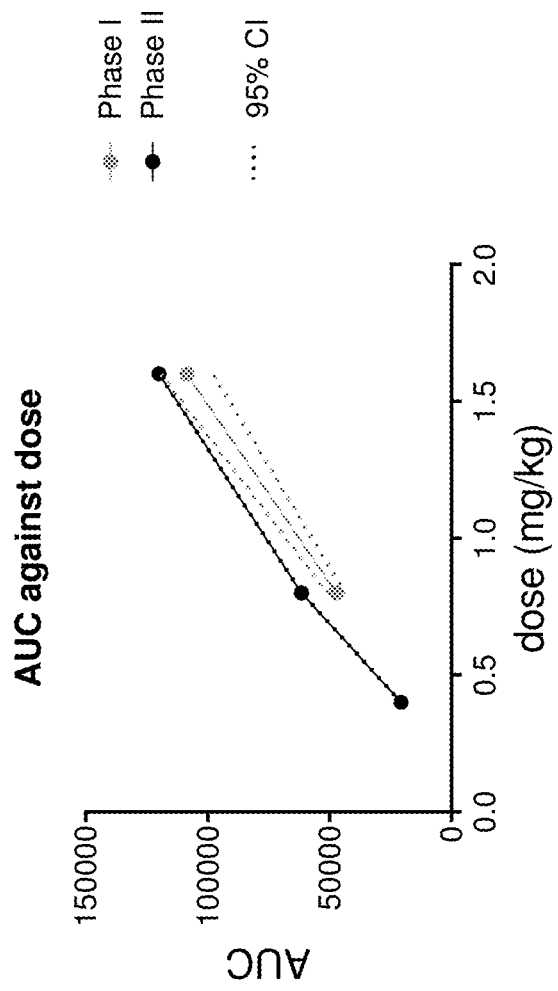

FIG. 6 is an AUC vs. dose graph showing a linear increase in RecAP concentrations. Exposure in patients in the STOP-AKI clinical trial is slightly higher compared to healthy subjects. Dose linearity and proportionality were observed over the dose range (0.4-1.6 mg/kg).

Figure 7:
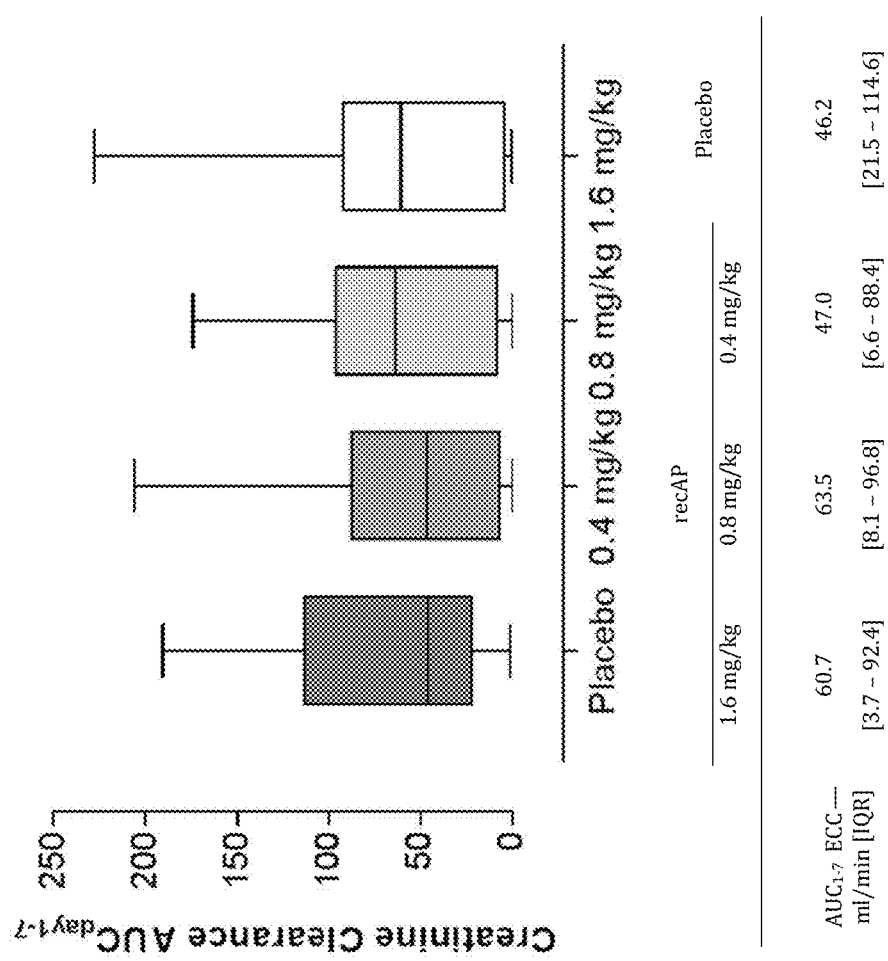

FIG. 7 is a box whisker plot showing creatinine clearance $AUC_{1-7}$ values corresponding to placebo, and RecAP doses of 0.4 mg/kg, 0.8 mg/kg, and 1.6 mg/kg. The values plotted are shown in the table under the plot. $AUC_{1-7}$ denotes area under the ECC curve from day 1 through day 7, divided by 7 to provide a time-corrected clearance in ml/min.

FIG. 8 is a table showing primary and secondary end points (placebo and RecAP 0.6 mg/kg group). $AUC_{1-7}$ denotes area under the ECC curve from day 1 through day 7, divided by 7 to provide a time-corrected clearance in ml/min. Abbreviations: CI (confidence interval), CKD-EPI (Chronic Kidney Disease Epidemiology Collaboration), ECC (endogenous creatinine clearance), eGFR (estimated glomerular filtration rate), ICU (intensive care unit), IQR (interquartile range), MAKE (major adverse kidney events), RRT (renal-replacement therapy), SOFA (Sequential Organ Failure Assessment).

§ RRT incidence indicates the percentage of patients that needed RRT following randomization.

| With last observation carried forward.

* MAKE 28: received RRT before or on day 28 or died before or on day 28. Proportion that met at least one of the criteria.

† MAKE 60: eGFR <60 ml/min at day 60 estimated by the CKD-EPI formula based on serum creatinine or required chronic RRT, before or on day 60 or died before or on day 60. Proportion that met at least one of the criteria.

‡ MAKE 90: 60: eGFR <60 ml/min at day 90 estimated by the CKD-EPI formula based on serum creatinine or required chronic RRT, before or on day 90 or hospitalization for new episode of AKI before or on day 90 or died before or on day 90. Proportion that met at least one of the criteria.

§§ Denotes the absolute difference (for continuous variables).

†† Denotes the odds ratio (for categorical variables).

‡‡ Denotes the hazard ratio (for events).

FIG. 9A shows the effect of RecAP on Endogenous Creatinine Clearance (ECC). Treatment effect of RecAP compared with placebo on ECC total curve: P=0.036. For missing values last observation carried forward (LOCF) and interpolation was applied. * depicts P<0.05, # depicts P=0.06.

FIG. 9B shows the effect of RecAP on Blood Urea Nitrogen (BUN) clearance. Treatment effect of RecAP compared with placebo on BUN clearance total curve: P=0.033. For missing values last observation carried forward (LOCF) and interpolation was applied. * depicts P<0.05, # depicts P=0.06.

Figure 10:
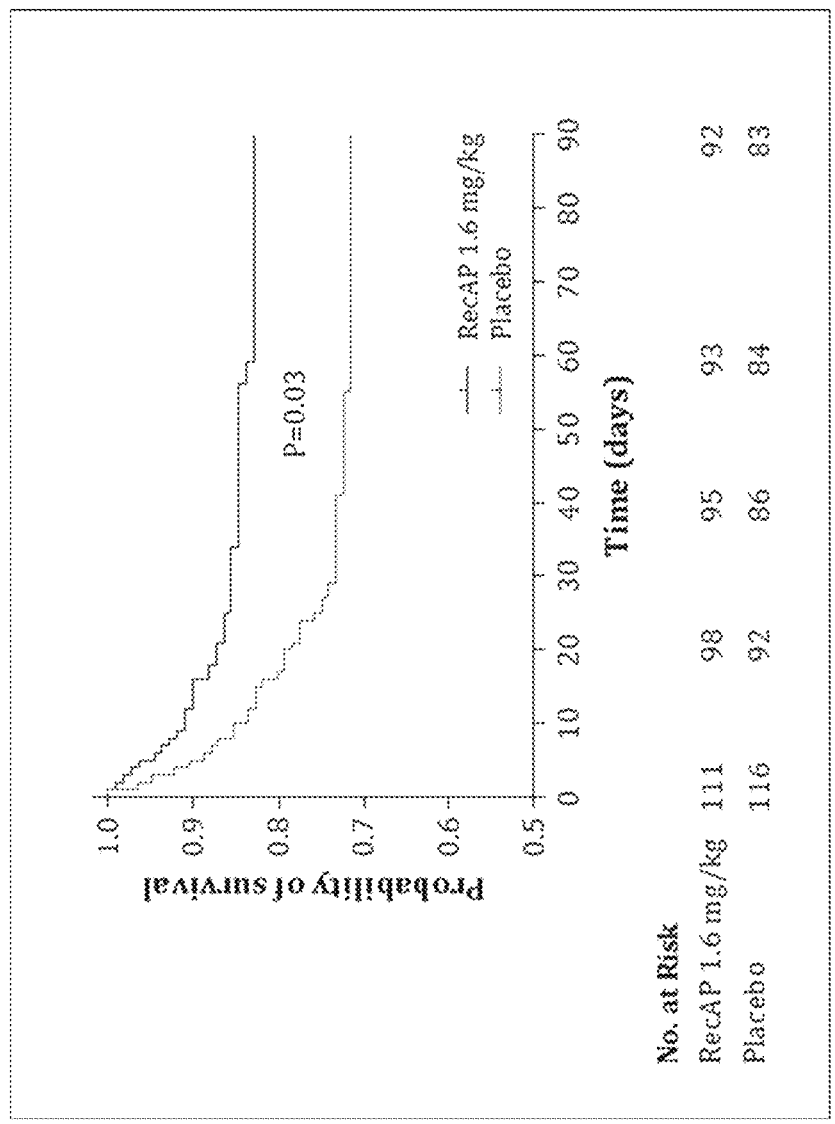

FIG. 10 shows a Kaplan-Meier probability of survival curve for SA-AKI subjects from randomization to day 90 (placebo group and RecAP 1.6 mg/kg group). Effect of RecAP compared with placebo on day 28 mortality: P=0.02. Effect of RecAP compared with placebo on day 90 mortality: P=0.03.

Figure 11:
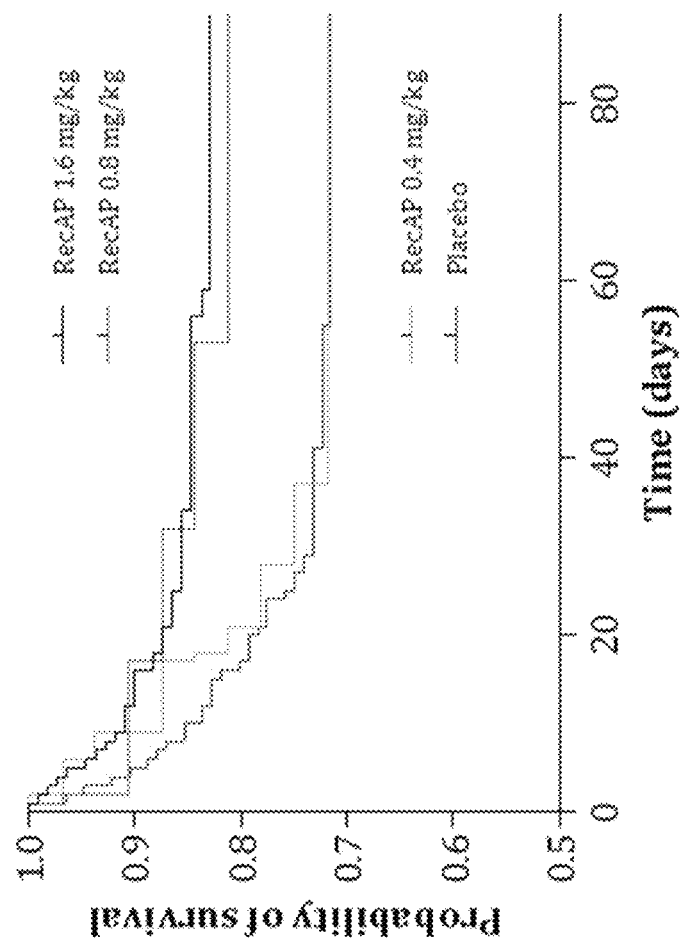

FIG. 11 shows probability of survival for SA-AKI subjects after administration of RecAP at 0.4. mg/kg, 0.8 mg/kg, or 1.6 mg/kg doses, or placebo over 90 days.

FIG. 12 shows primary and secondary endpoints for all treatment groups (RecAP at 0.4. mg/kg, 0.8 mg/kg, or 1.6 mg/kg doses, or placebo).

Figure 13A:
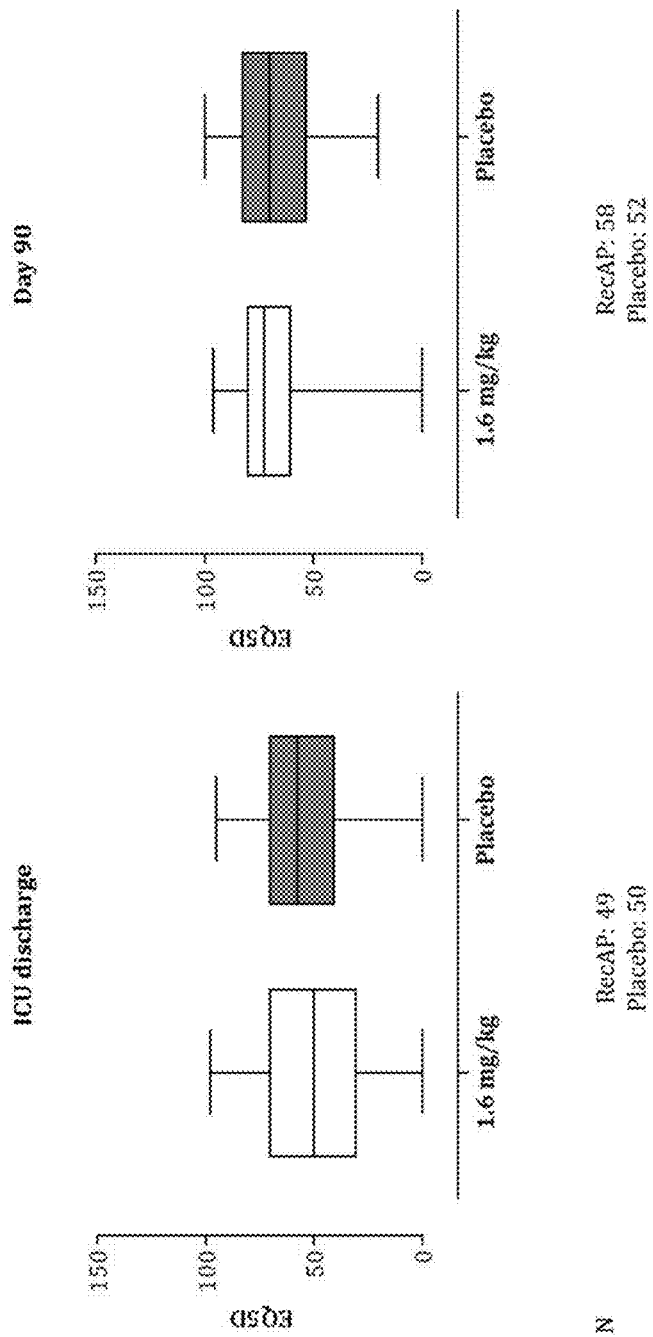

FIG. 13A shows quality of life (QoL) assessments measured by EuroQoL (EQSD) score at ICU (left drawing) and Day 90 (right drawing).

Figure 13B:
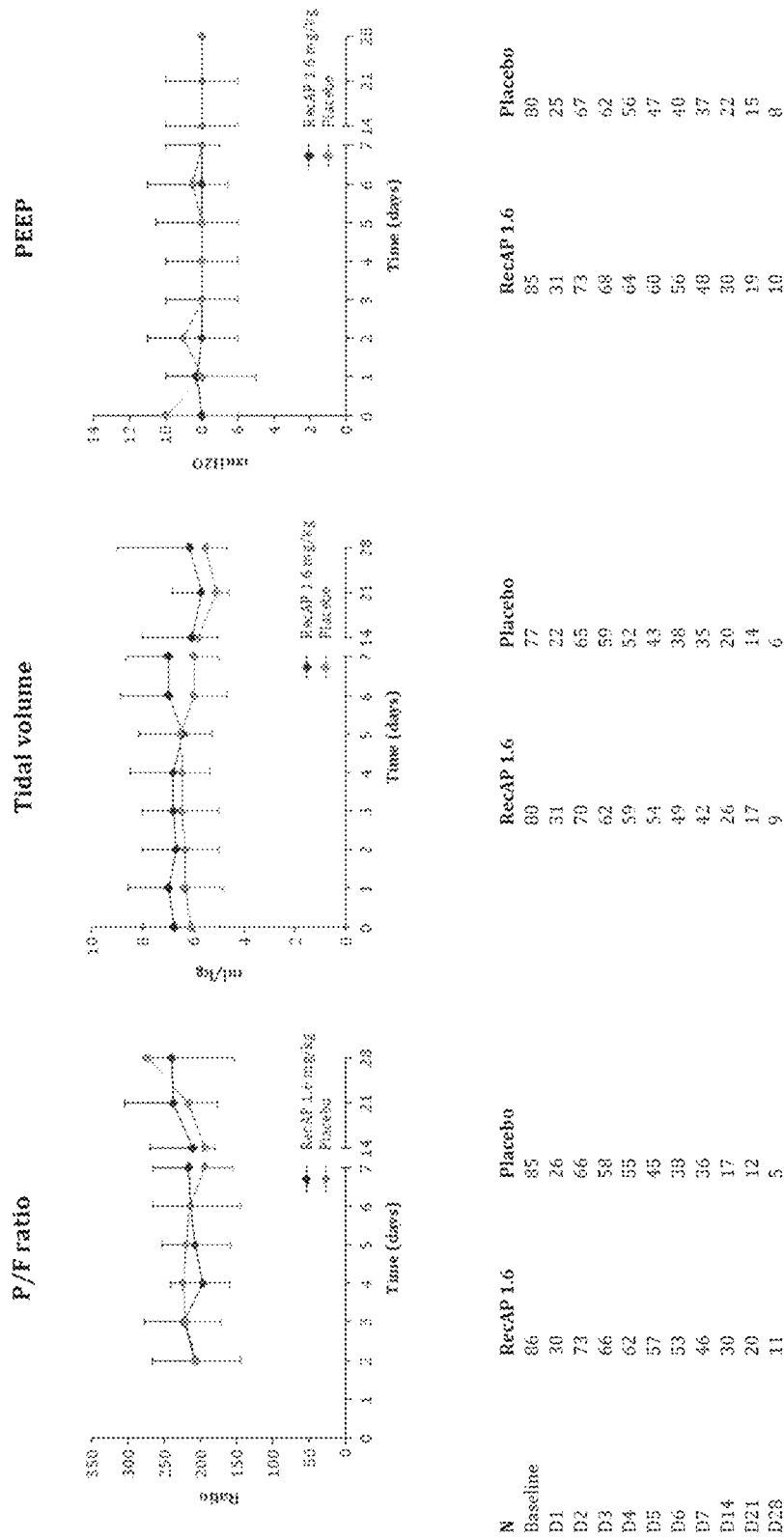

FIG. 13B shows lung function parameters (P/F ratio, tidal volume and PEEP), depicted as medians, for the 1.6 mg/kg RecAP dose and placebo groups. Numeric values are shown below the graphics.

Figure 13C:
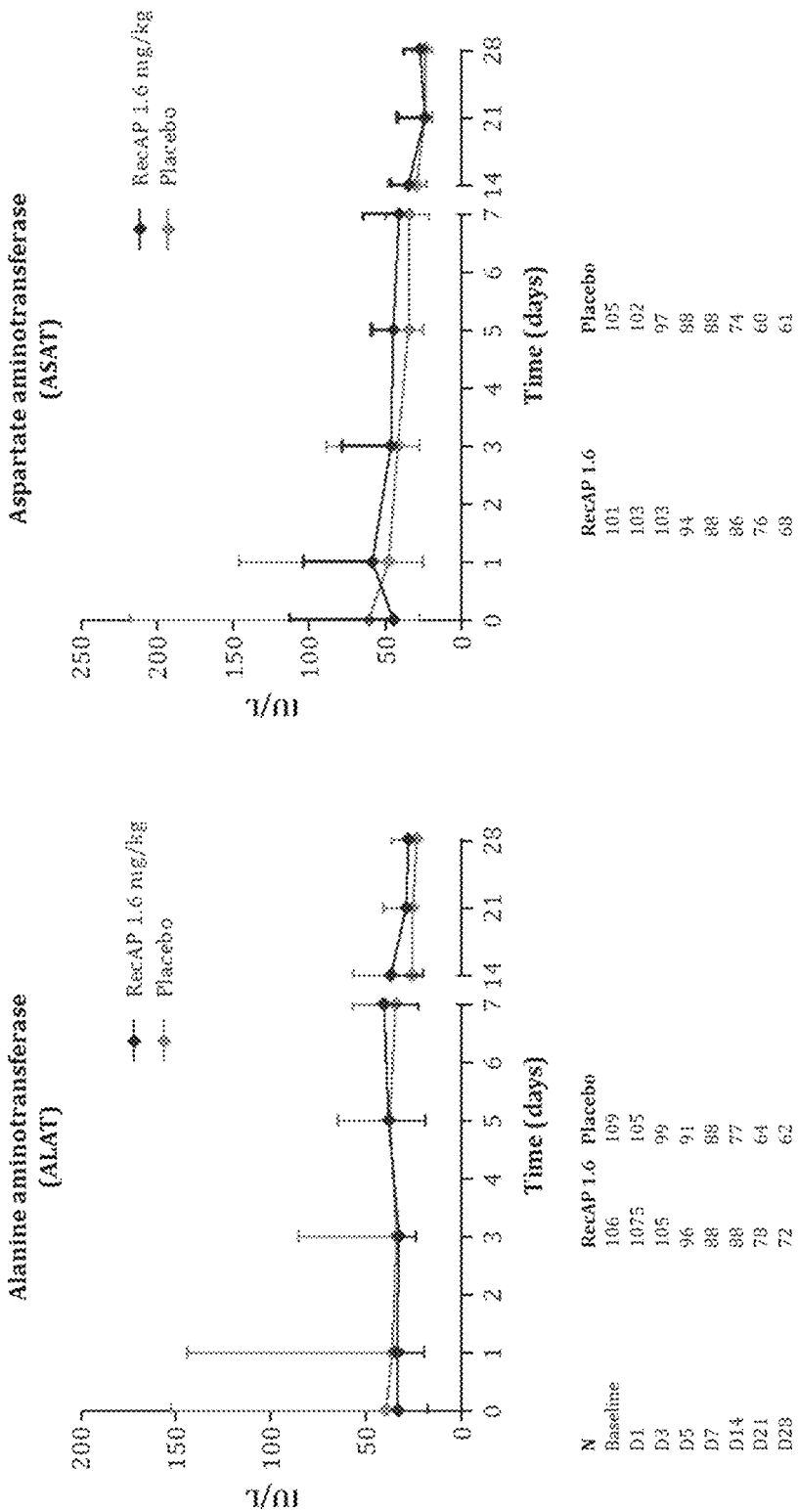

FIG. 13C shows liver function parameters (alanine aminotransferase, and aspartate aminotransferase activity), depicted as medians, for the 1.6 mg/kg RecAP dose and placebo groups. Numeric values are shown below the graphics.

Figure 13D:
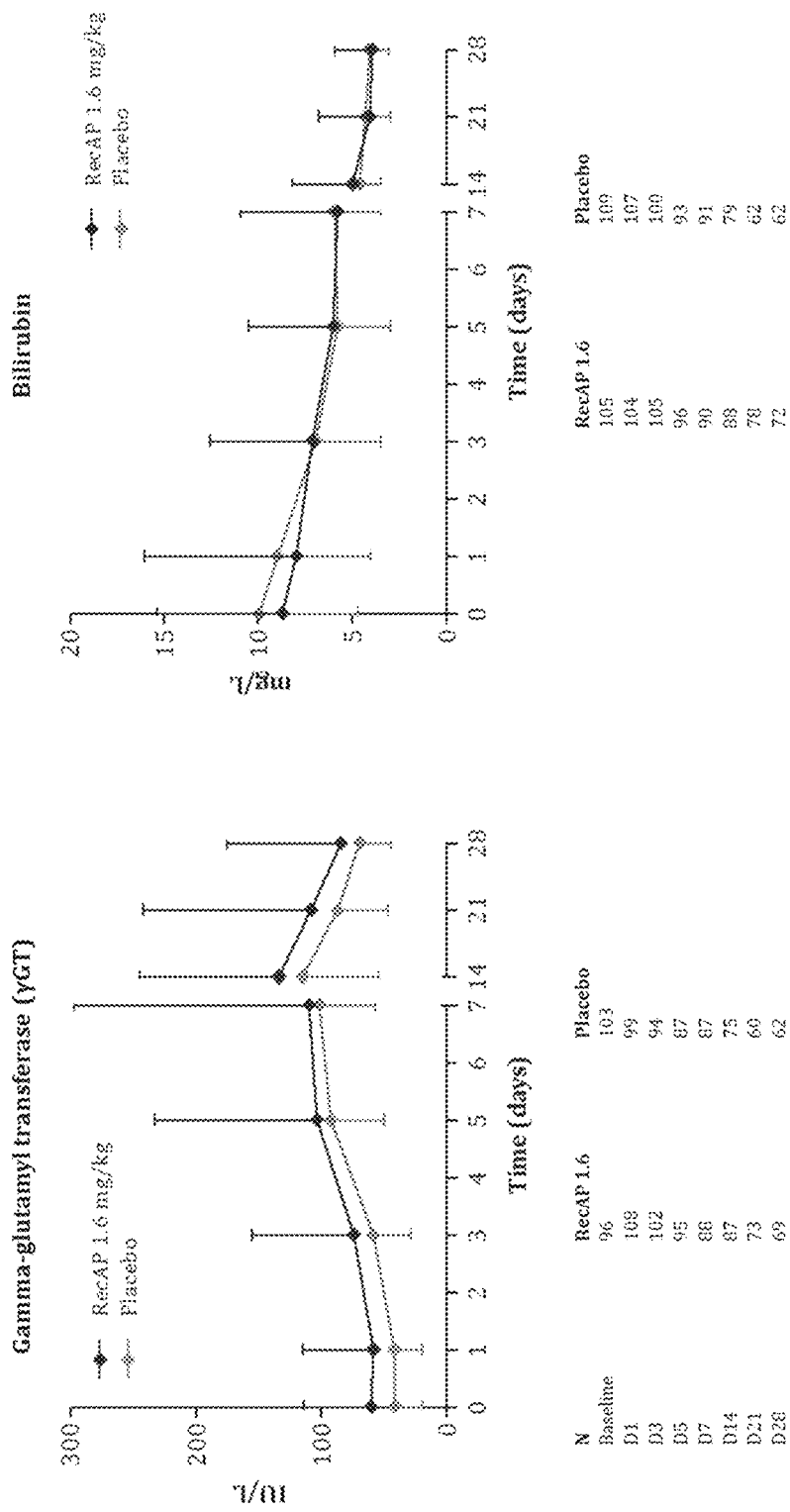

FIG. 13D shows liver function parameters (gamma-glutamyl transferase activity, and bilirubin levels), depicted as medians, for the 1.6 mg/kg RecAP dose and placebo groups. Numeric values are shown below the graphics.

Figure 13E:
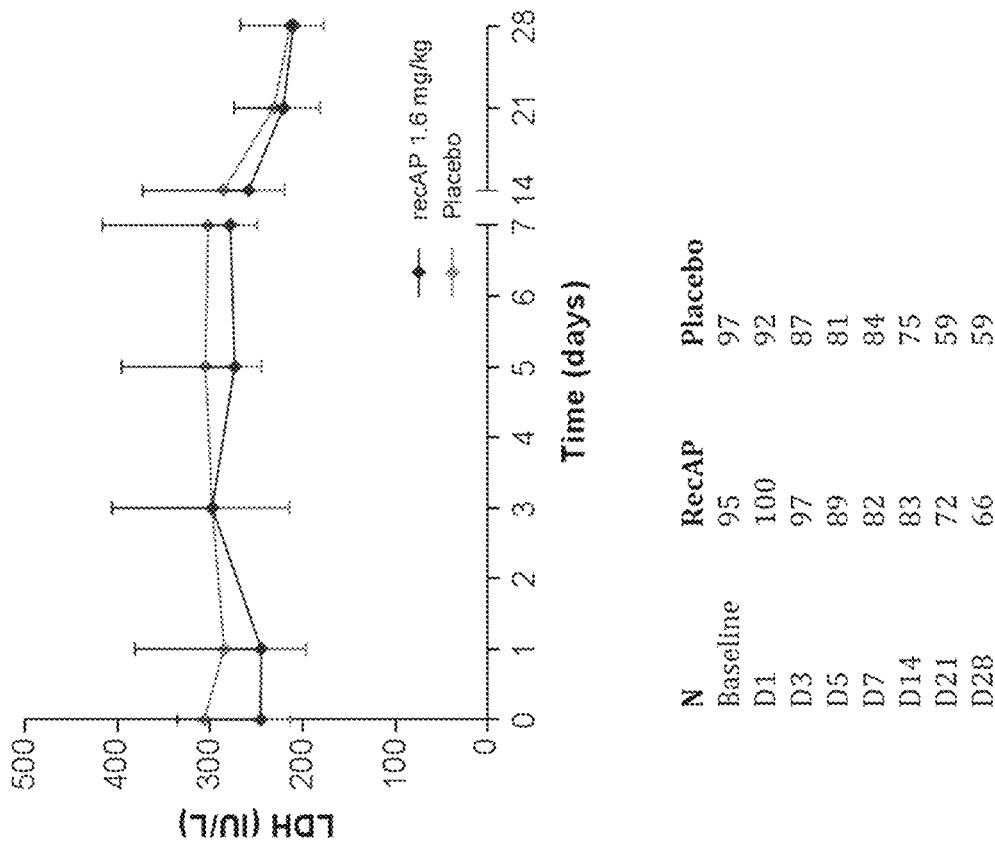

FIG. 13E shows LDH activity, depicted as median, for the 1.6 mg/kg RecAP dose and placebo groups. Numeric values are shown below the graphics.

FIG. 14 shows the results of a post hoc multivariate analysis.

Figure 15A:
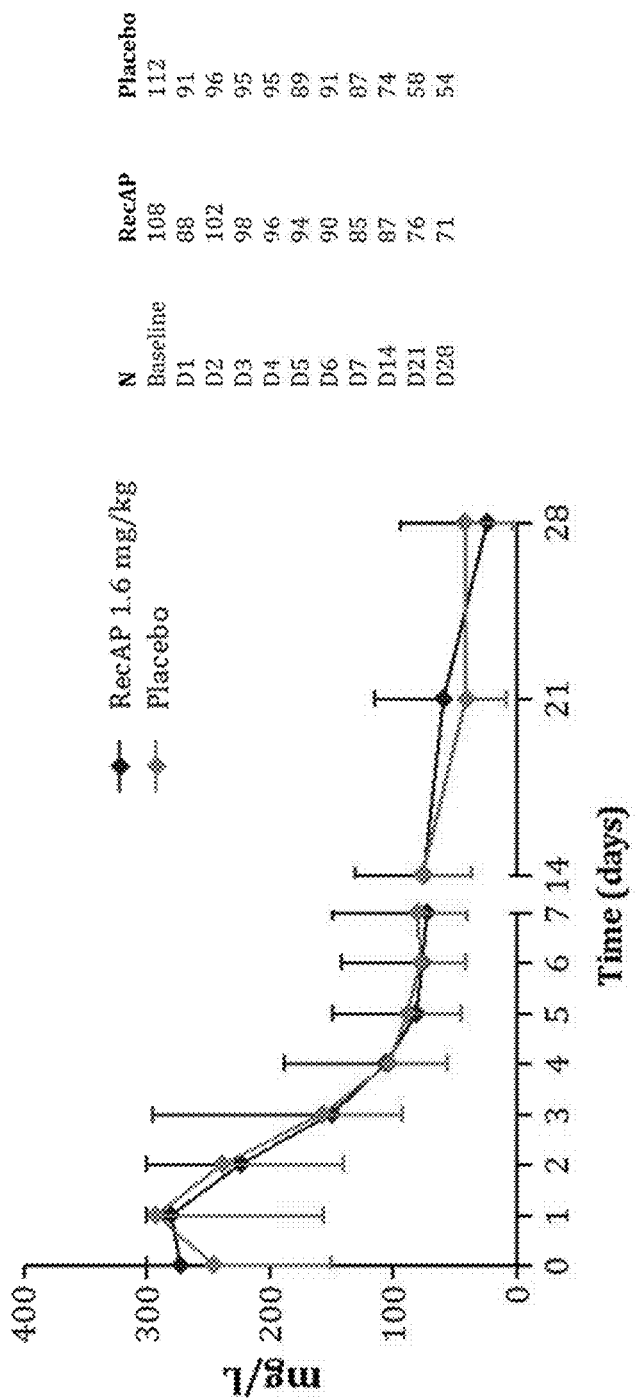

FIG. 15A shows C-reactive protein (CRP) concentrations (mg/L), depicted as medians, for the 1.6 mg/kg RecAP dose and placebo groups. Numeric values are show to the right of the graphic.

Figure 15B:
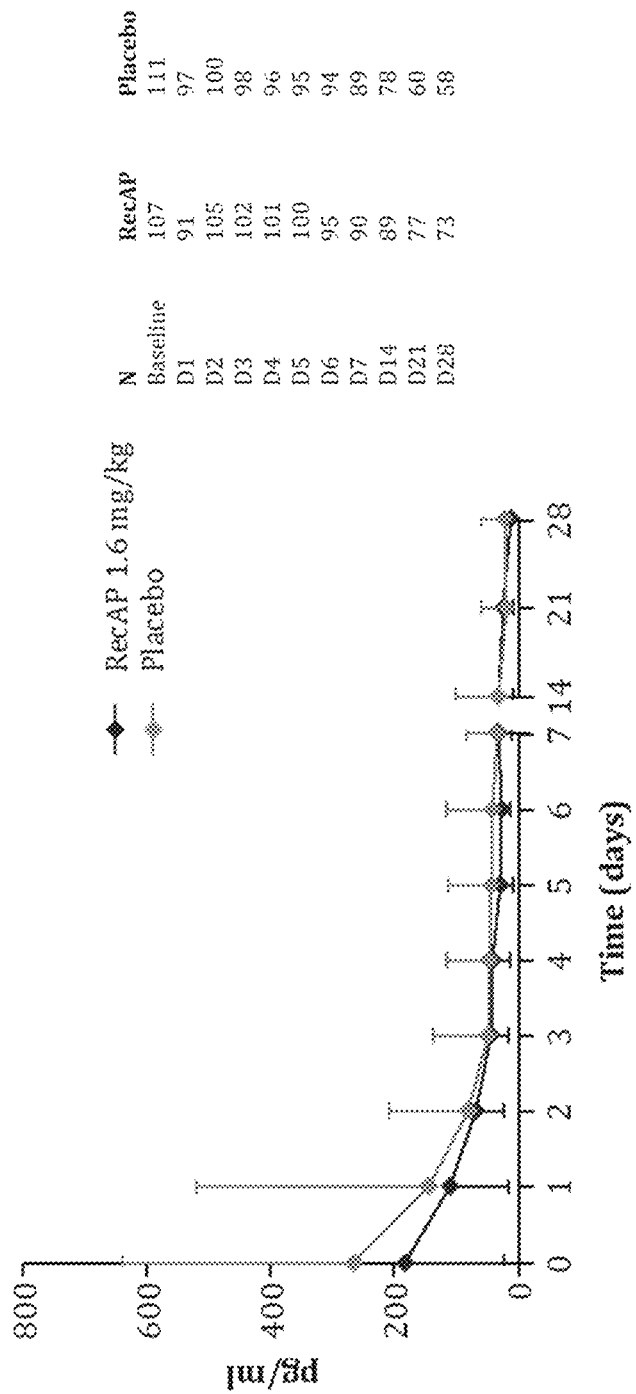

FIG. 15B shows interleukin 6 (IL-6) concentrations (pg/ml), depicted as medians, for the 1.6 mg/kg RecAP dose and placebo groups. Numeric values are show to the right of the graphic.

Figure 15C:
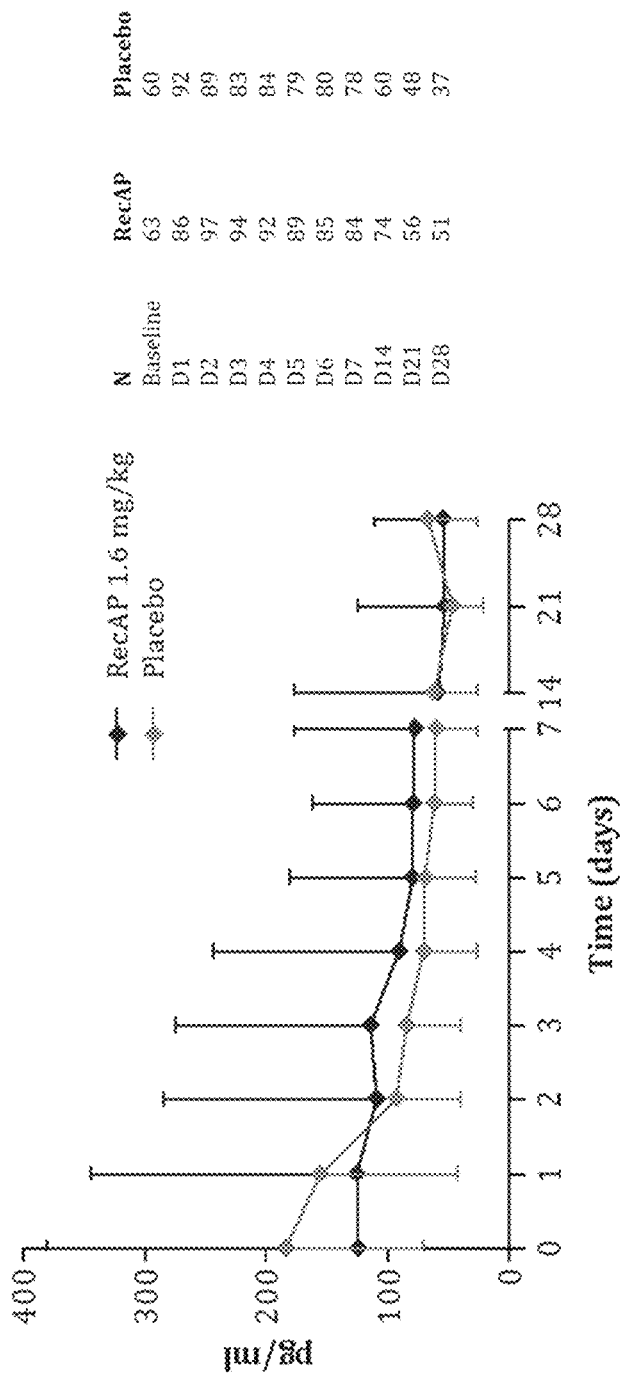

FIG. 15C shows interleukin 18 (IL-18) concentrations (pg/ml), depicted as medians, for the 1.6 mg/kg RecAP dose and placebo groups. Numeric values are show to the right of the graphic.

Figure 15D:
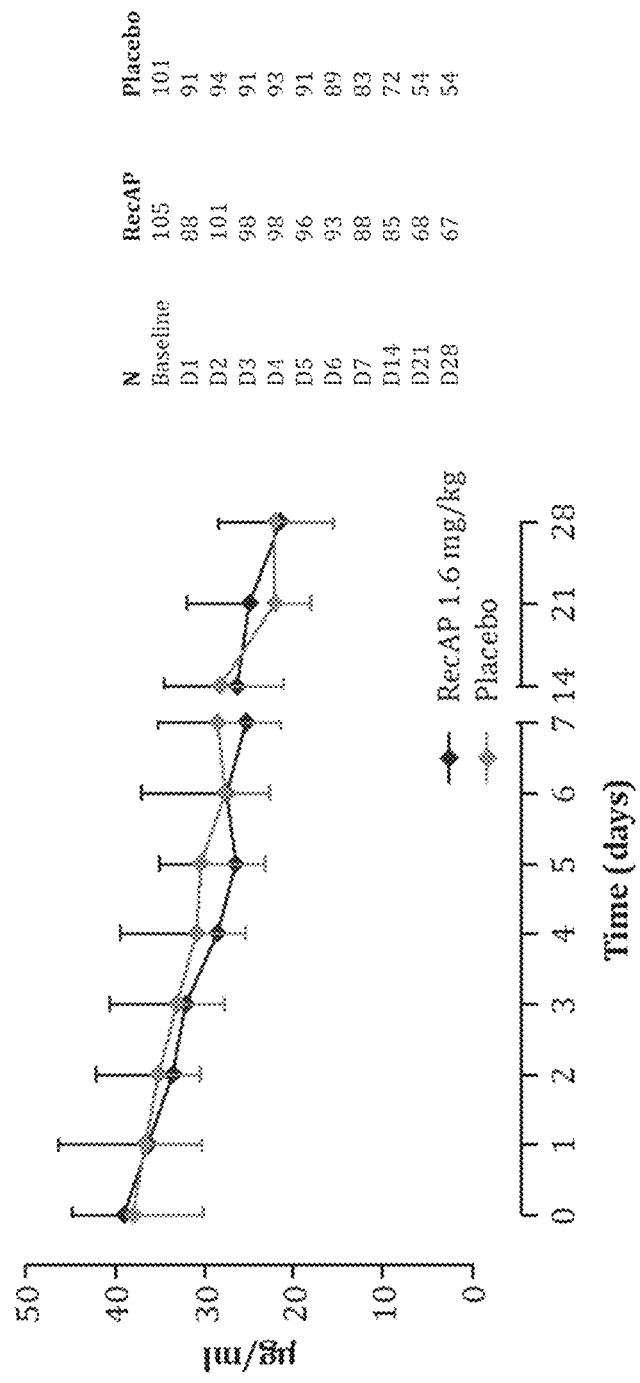

FIG. 15D shows lipopolysaccharide binding protein (LBP) concentrations (μg/ml), depicted as medians, for the 1.6 mg/kg RecAP dose and placebo groups. Numeric values are show to the right of the graphic.

Figure 15E:
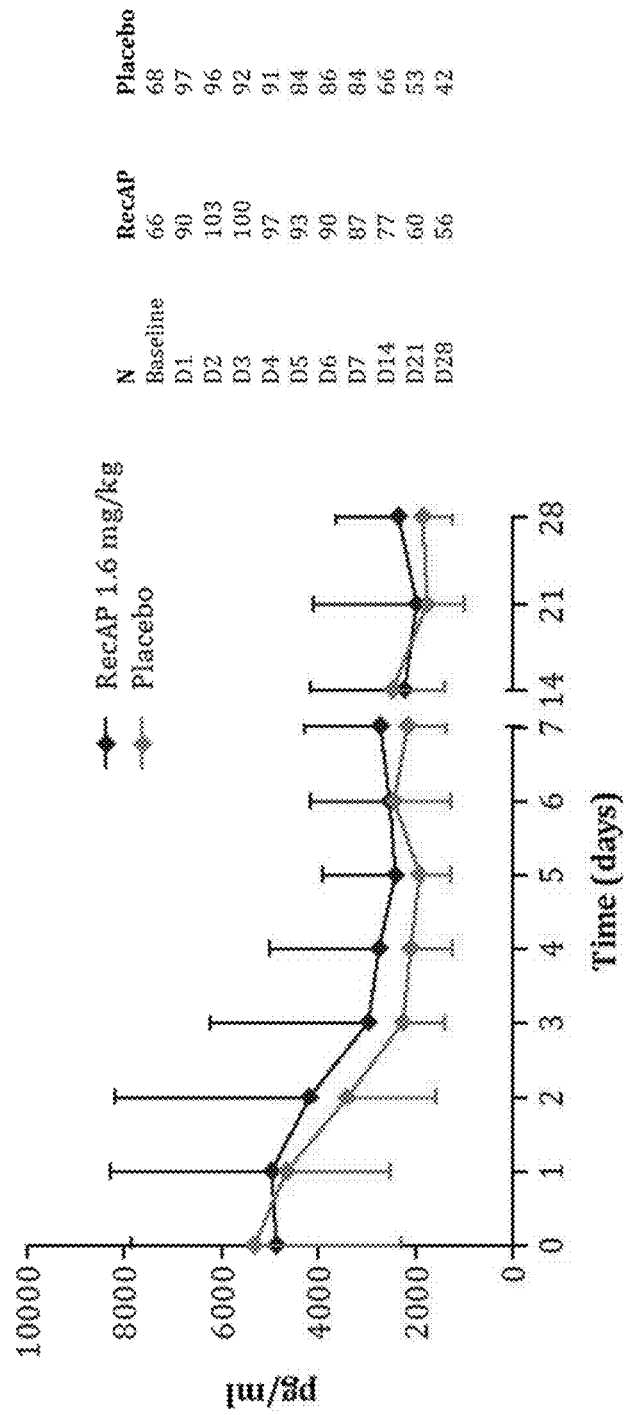

FIG. 15E shows Kidney Injury Molecule 1 (KIM-1) concentrations (pg/ml), depicted as medians, for the 1.6 mg/kg RecAP dose and placebo groups. Numeric values are show to the right of the graphic.

Figure 15F:
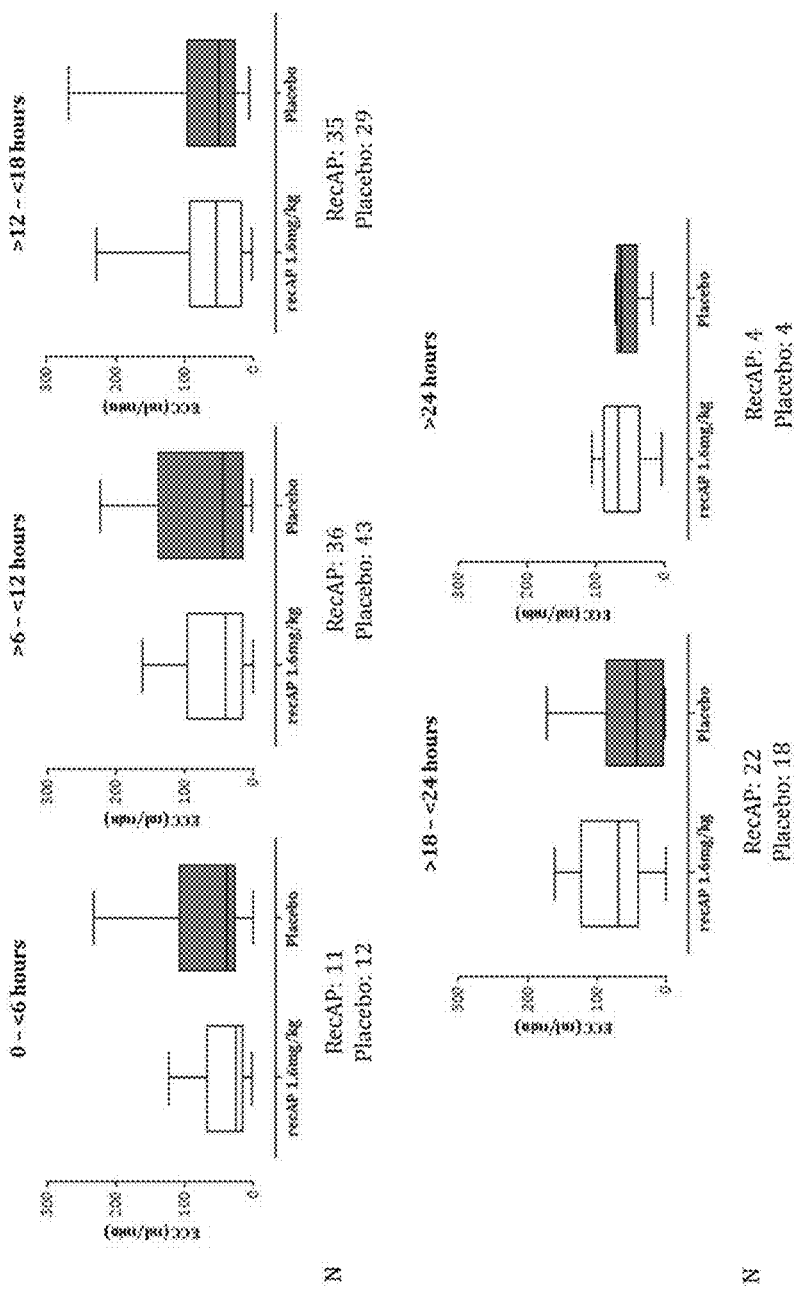

FIG. 15F shows the influence of the duration between first diagnosis of AKI and start of study drug infusion (hours) on primary endpoint ECC.

Figure 15G:
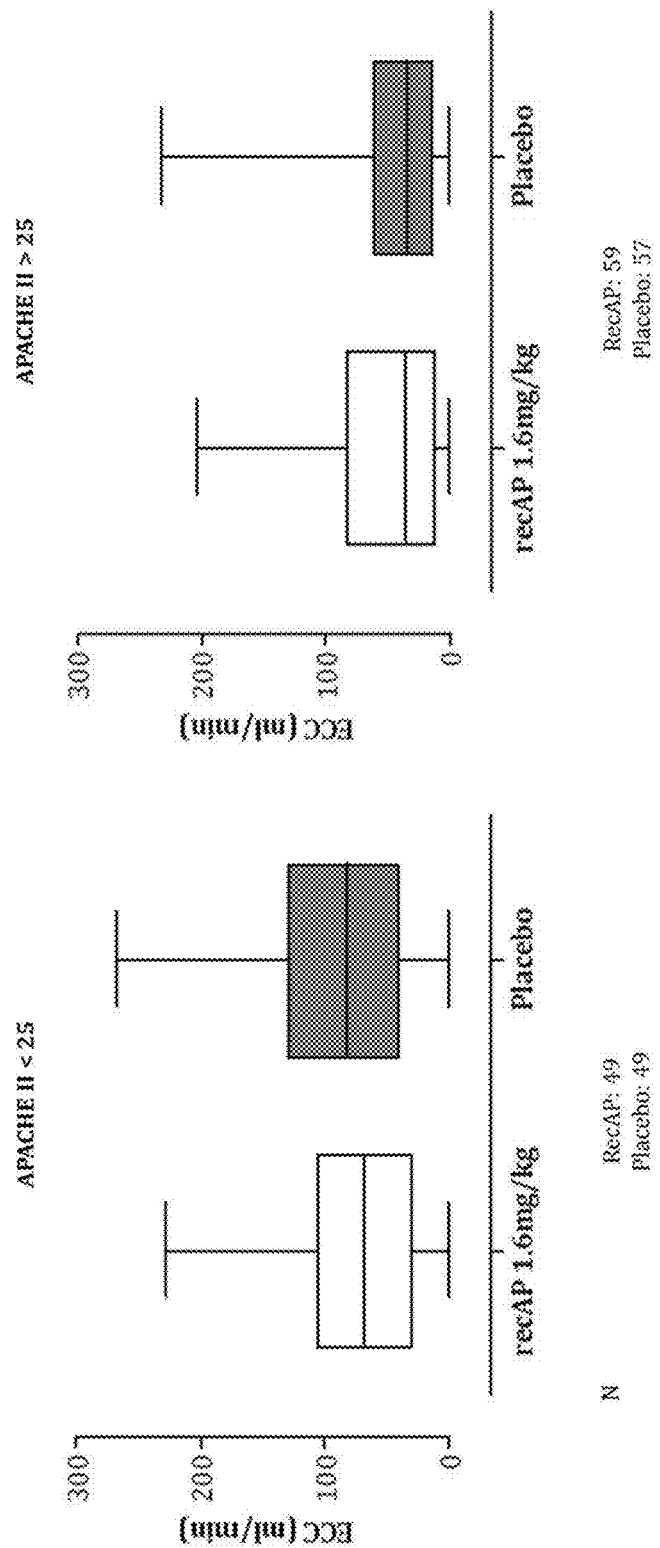

FIG. 15G shows the influence of baseline disease severity by APACHE II score on primary endpoint ECC.

Figure 15H:
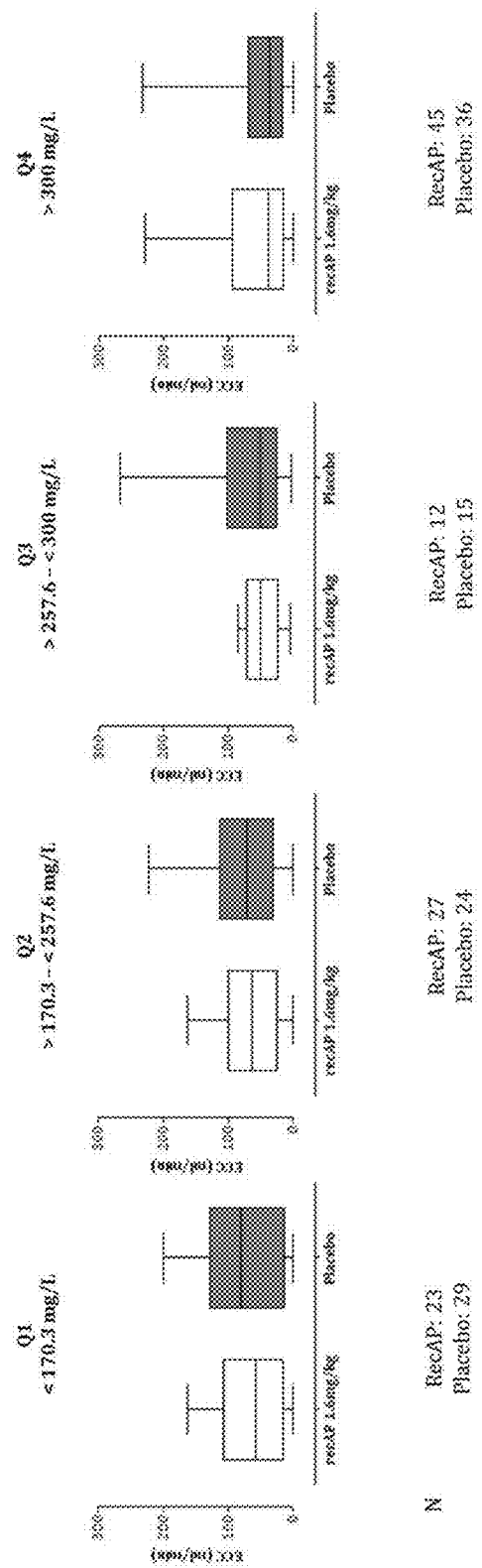

FIG. 15H shows the influence of inflammation as measured by baseline C-reactive protein (CRP) concentrations (mg/L) on primary endpoints ECC.

Figure 15I:
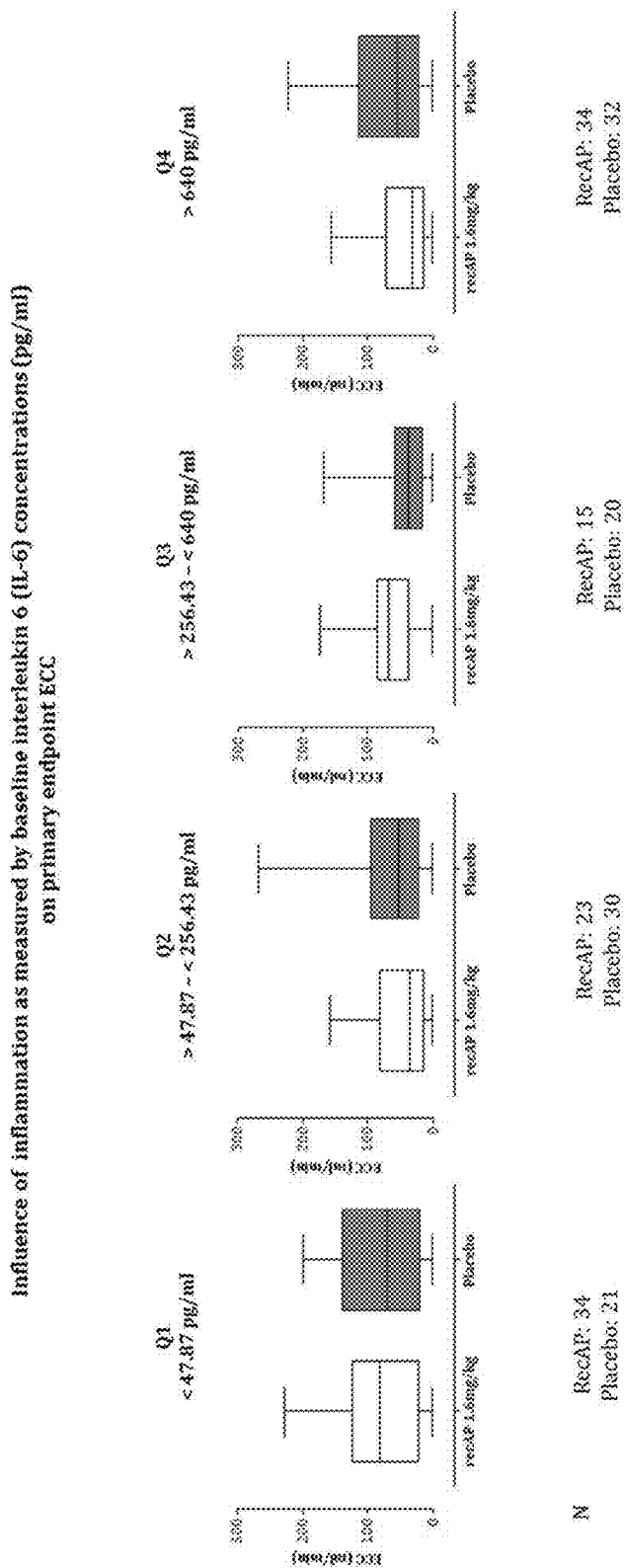

FIG. 15I shows the influence of inflammation as measured by baseline interleukin 6 (IL-6) concentrations (pg/ml) on primary endpoint ECC.

Figure 15J:
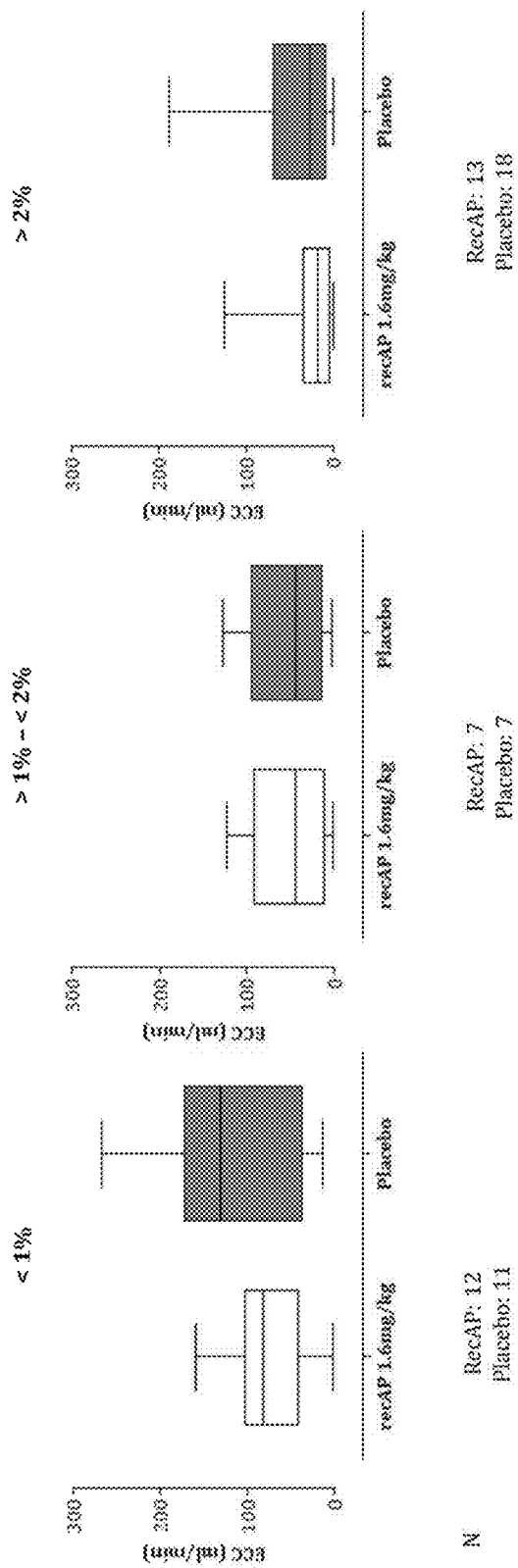

FIG. 15J shows the influence of the fractional excretion of sodium (% of FeNa) at baseline on primary endpoint ECC.

Figure 15K:
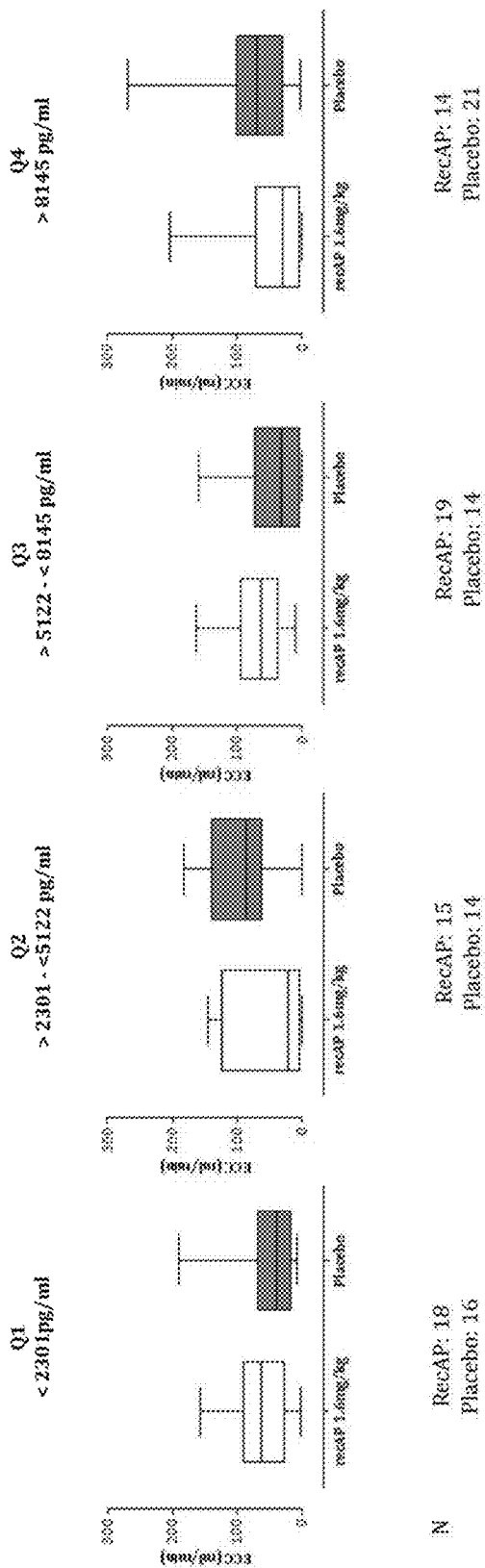

FIG. 15K shows the influence of baseline Kidney Injury Molecule 1 (KIM-1) concentrations (pg/ml) on primary endpoint ECC.

Figure 15L:
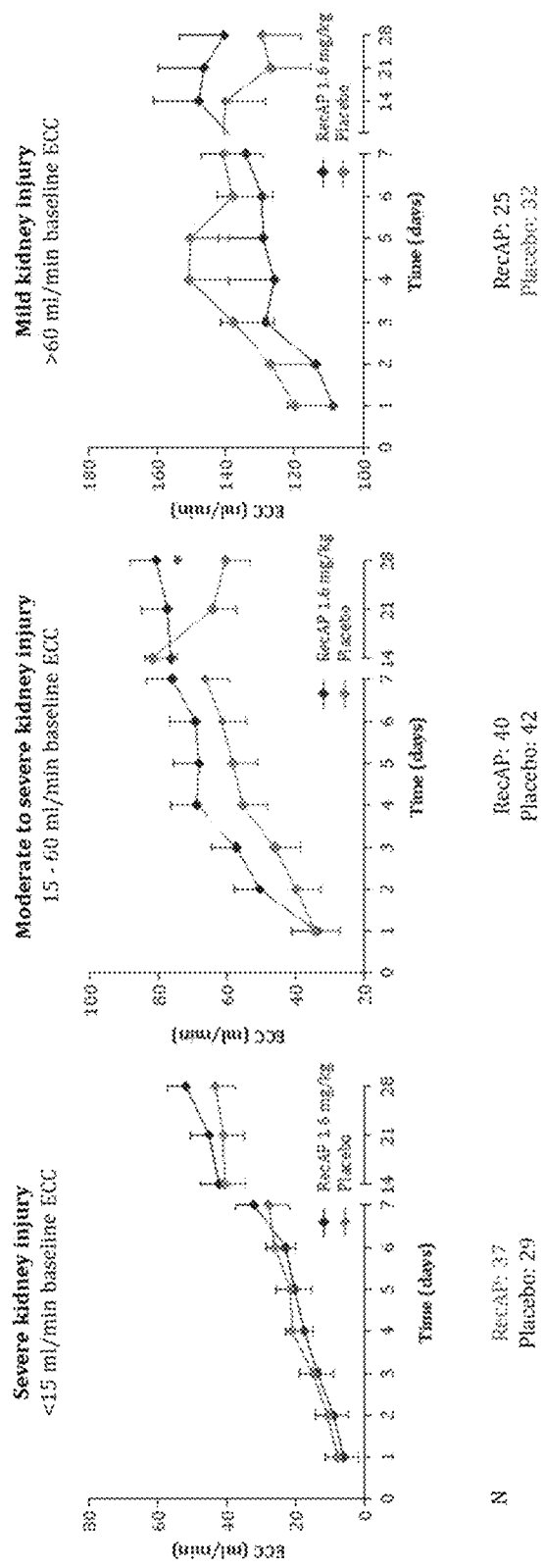

FIG. 15L shows the difference in baseline kidney function on primary endpoint ECC, depicted as medians.

FIG. 16 shows treatment-emergent adverse events observed during the STOP-AKI study.

Figure 17:
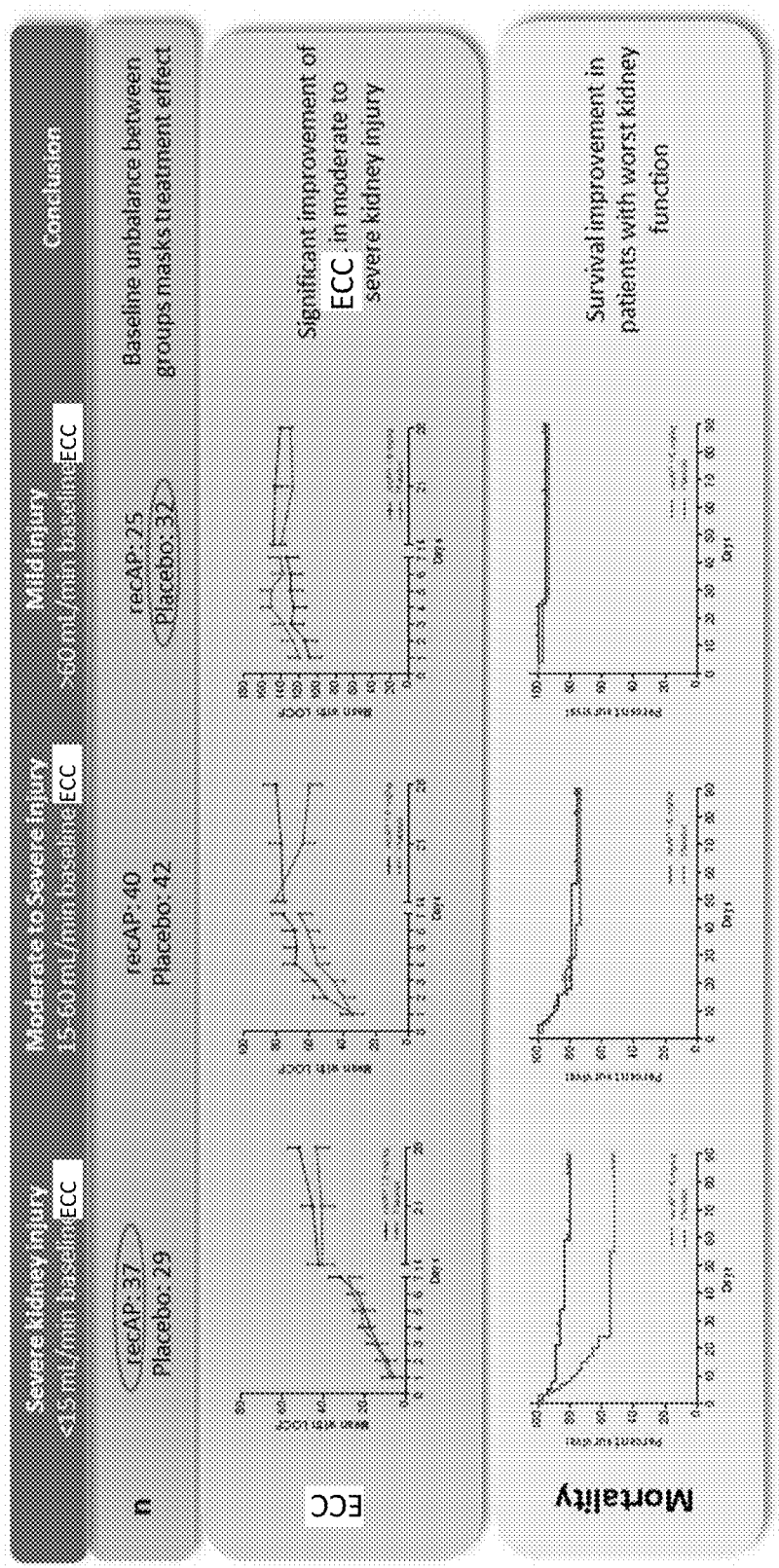

FIG. 17 shows a subgroup analysis of subjects in the STOP-AKI study stratified according to severity in kidney injury. Thresholds or cut-offs are based on ECC.

FIG. 18 shows coefficients and model fit statistics of two different Cox parallel-hazard models (CoxPH). (Model 1) CoxPH model that predicts overall survival (OS) in the STOP-AKI study as a continuous function of the baseline ECC, where the measurements at baseline and day 1 were averaged (MeanBaseECC; missing values were ignored in this calculation). (Model 2) CoxPH model predicting OS in 3 different groups on the basis of MeanBaseECC as follows; <15 as the reference group, >=15 but <60 as the Severe-Mild group and >=60 as the Normal group.

Figure 19:
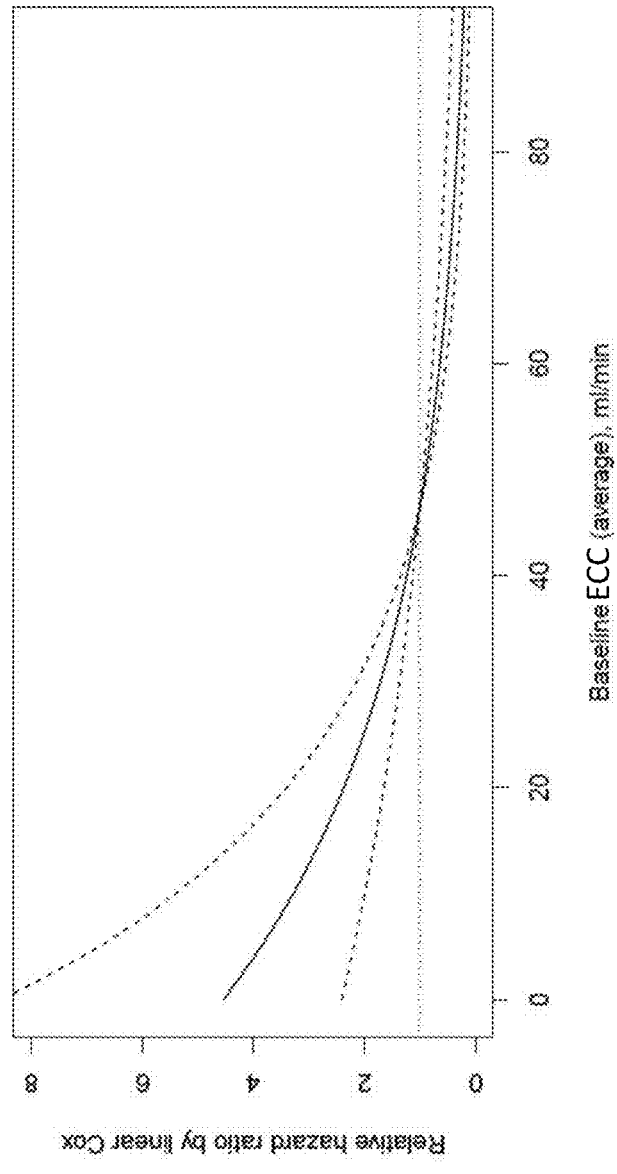

FIG. 19 shows hazard ratios (HR) for overall survival according to the continuous CoxPH model (see Model 1 in FIG. 18) as a function of average baseline ECC, where measurements at baseline and day 1 were averaged. The HR relative to the mean ECC in the population, 46 ml/min, was calculated according to the model at different baseline levels (straight line) together with the standard errors (dashed line) and compared to the reference level, an HR of 1 (dotted horizontal reference line).

FIG. 20 shows hazard ratios (HR) for overall survival according to the continuous CoxPH model (see Model 1 in FIG. 18) at different values of average baseline ECC in ml/min, where measurements at baseline and day 1 were averaged. For each group according to CKD criteria, the median of average baseline ECC is tabulated, together with the number of patients in each group, and the HR for OS relative to the mean average baseline ECC, 46 ml/min, according to the CoxPH model and its standard error (seHR). Additionally, the CKD criteria boundaries, i.e., 15 ml/min between "Kidney failure" (Severe Kidney Injury) and "Severe-mild" (Moderate to Severe Kidney Injury), and subsequently 60 ml/min as the boundary to "Normal" (Mild Injury or Normal) are tabulated with corresponding model HR and standard error.

Figure 21:
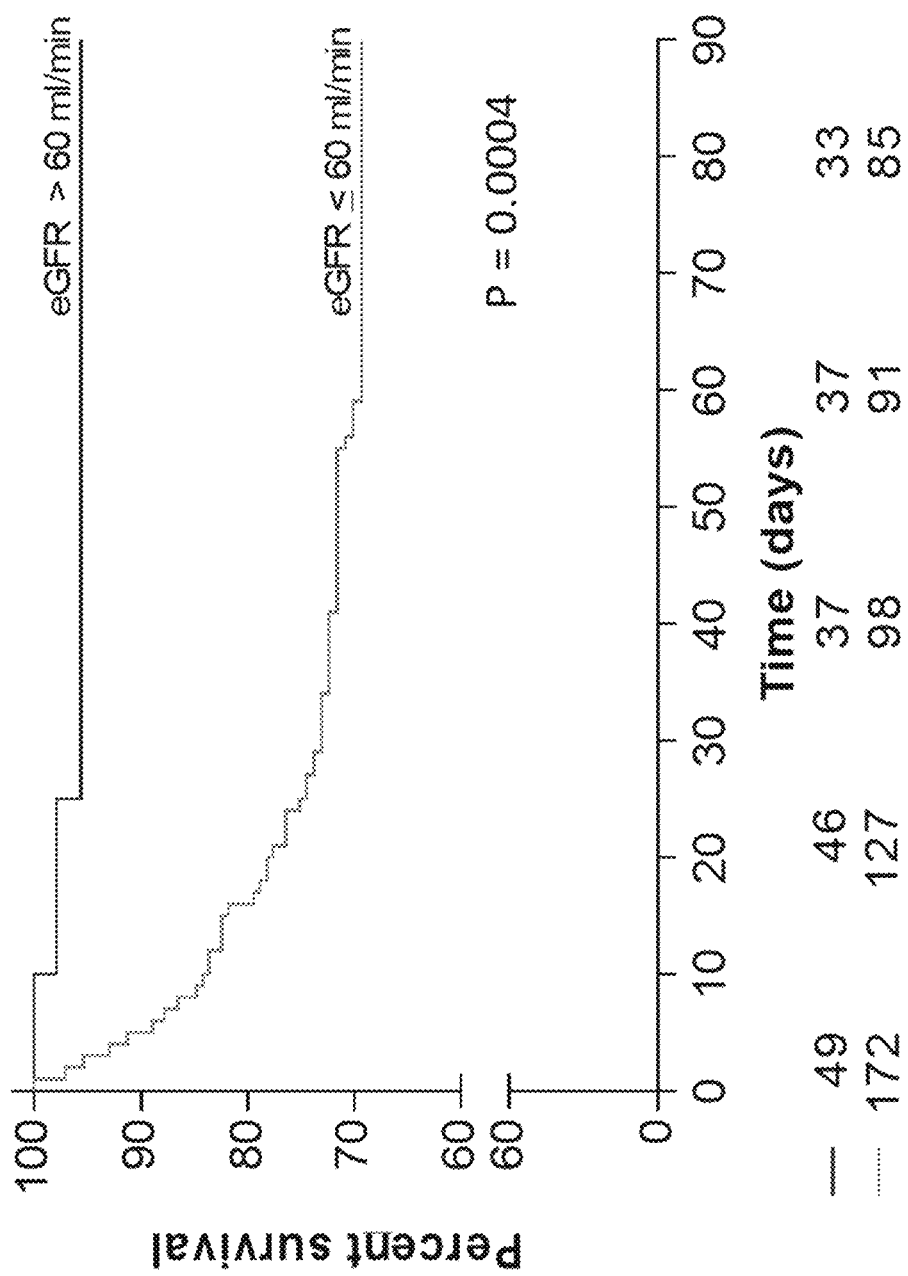

FIG. 21 shows a Kaplan Meier Time to Death curve (per baseline eGFR subgroups). Baseline eGFR was measured with CKD-EPI (Chronic Kidney Disease Epidemiology Collaboration) equation.

Figure 22:
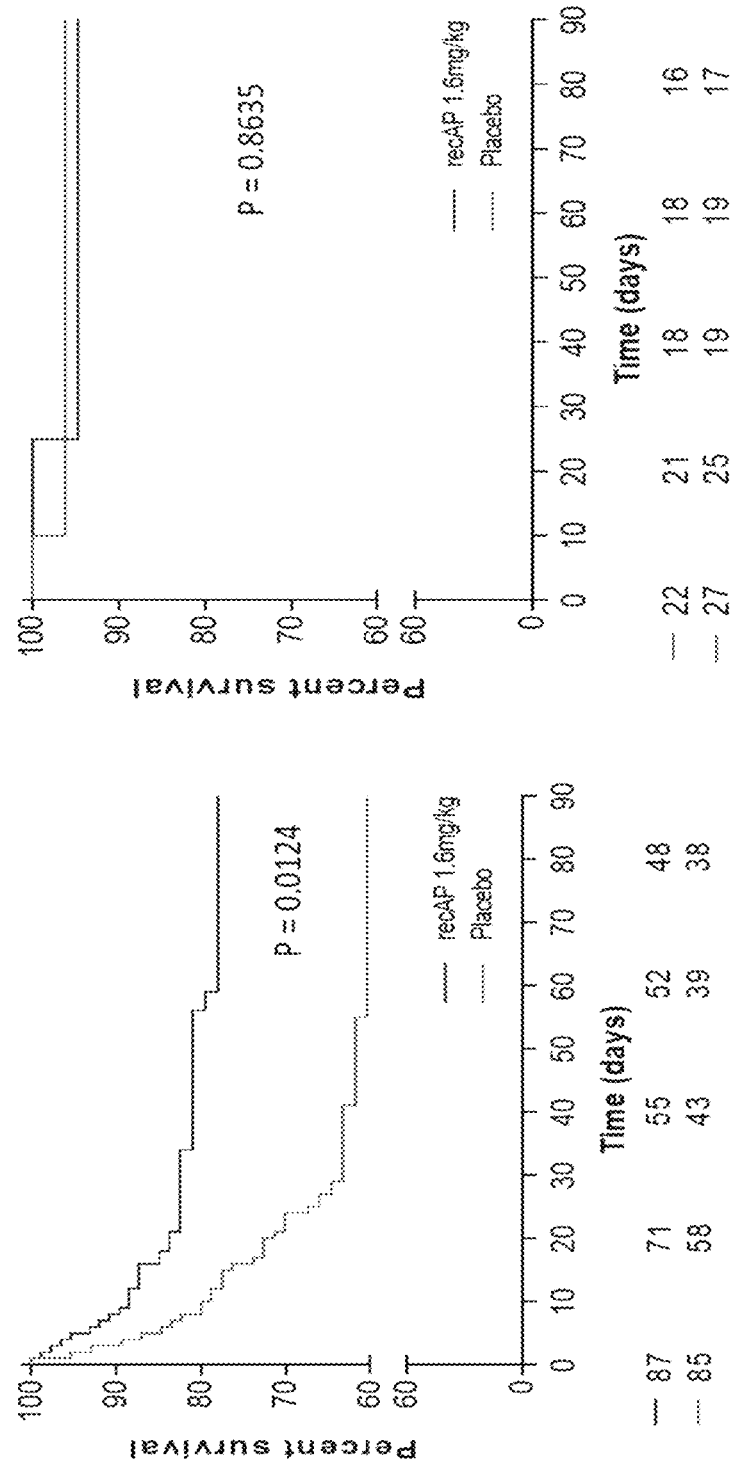

FIG. 22 shows a Kaplan Meier Time to Death curve (recAP versus placebo in subgroups with baseline eGFR above (right panel) and below (left panel) 60 mL/min). Baseline eGFR was measured with CKD-EPI (Chronic Kidney Disease Epidemiology Collaboration) equation.

DETAILED DESCRIPTION

Sepsis-associated AKI (SA-AKI) is a multifactorial syndrome with inflammatory, nephrotoxic, and ischemic insults occurring simultaneously with other pathophysiological responses rapidly leading to renal impairment (Bonventre et al. J Clin Invest 2011; 121:4210-21; Gomez et al. Shock 2014; 41:3-11). Currently, no approved pharmacologic interventions are available to prevent or treat AKI (Joannidis et al. Intensive Care Medicine 2017; 43:730-49). Alkaline phosphatase (AP) was originally considered as a novel treatment for sepsis in general (Poelstra et al. American Journal of Pathology 1997; 151:1163-69.; Verweij et al. Shock 2004; 22:174-9). In two small clinical trials bovine AP administration improved renal function in patients with sepsis (Heemskerk et al. Crit Care Med 2009; 37:417-23, e1; Pickkers et al. Crit Care 2012; 16:R14).

The STOP-AKI clinical trial was an international randomized, double-blind, placebo-controlled, four arm, parallel-group, dose-finding adaptive phase IIa/IIb multicenter study conducted in critically ill adults with sepsis-associated acute kidney injury. In this study a total of 301 patients were enrolled across 53 sites in 11 countries in the European Union and North America. The four arms of the study consisted of patients receiving RecAP 0.4 mg/kg, 0.8 mg/kg, 1.6 mg/kg or placebo. Following the interim-analysis, the study continued with RecAP 1.6 mg/kg as treatment.

RecAP is a chimeric AP that combines the properties of two human isoenzymes, intestinal and placental AP (Kiffer-Moreira et al. PLoS One 2014; 9:e89374). Replacing the crown domain of intestinal AP (the most biologically active isoenzyme) with the crown domain of placental AP (which has the longest half-life) creates a highly stable, biologically active enzyme (Kiffer-Moreira et al. PLoS One 2014; 9:e89374). See, e.g., U.S. Pat. Nos. 8,586,032 and 8,557,545, and U.S. Patent Appl. Publ. Nos. US20170009216 and US20160250299, the disclosures of which are incorporated herein by reference in their entireties.

Compared with placebo, RecAP 1.6 mg/kg did not affect creatinine clearance in the first week or renal replacement therapy rates. However, improvement of endogenous creatinine clearance on days 21 (P=0.02) and 28 (P=0.01) was more pronounced and the incidence of major adverse kidney events at days 60 (P=0.045) and 90 (P=0.03) was lower in patients receiving RecAP. All-cause 28-day mortality was 14.4% in RecAP-treated patients versus 26.7% in placebo-treated patients (P=0.02). No significant differences in (serious) adverse events were observed between groups. RecAP appeared safe and well tolerated.

A key observation of the study was that although short-term renal function was not affected, unexpected long-term beneficial effects derived from RecAP treatment were observed. These unexpected observation showed that treatment with RecAP resulted in enhanced and sustained recovery of renal function and better survival compared to placebo.

The long-term effects varied depending on the severity of the impairment in kidney function, i.e., some specific subgroups of subject responded particularly well to AP therapy. Thus, stratifying patients according to, e.g., particular markers of kidney function and/or biomarkers (e.g., ECC or eGFR) allows to identify particular effects of AP administration on specific subgroups. The parameter or parameters defining each of these subgroups (e.g., a series of thresholds, such as ECC or eGFR thresholds) can be used, for example, to evaluate the likelihood of a positive outcome, to selected patients for treatment, or to make decisions related to the AP treatment (e.g., modify dosage). For example, if the subject had moderate to severe kidney injury (corresponding, e.g., to a 15 mg/ml to 60 ml/min ECC), there was a statistically significant effect of RecAP which resulted in improved kidney function (as evidenced by improved creatinine clearance with respect to placebo). If the subject had severe kidney injury (corresponding, e.g., to <15 ml/min baseline ECC), there was a statistically significant long term effect resulting in improved survival. If the subject had ≤60 eGFR, there was also a statistically significant long term effect resulting in improved survival.

A goal of the present disclosure is to provide methods for preserving or improving renal function in a subject, especially in cases where the subject undergoes a treatment with a risk of reducing renal function, or suffers from or is at risk of sepsis. Another goal of the present disclosure is to prevent or shorten the duration of renal-replacement therapy (RRT), to increase the kidney creatinine clearance, and/or to increase survival.

Accordingly, the present disclosure relates to the use of an alkaline phosphatase (AP), e.g., RecAP, to preserve or improve kidney function in a subject with kidney injury, e.g., acute kidney injury (AKI), and in particular a subject with sepsis-associated AKI (SA-AKI). The disclosure provides, for example, methods for treating a subject with kidney injury, e.g., SA-AKI, comprising administering an AP, e.g., RecAP, to the subject. In some aspects, each dose of AP administered to the subject comprises at least 500 U/kg (0.8 mg/kg in the case of the clinical grade RecAP used). In some particular aspects, each AP dose is at least 1,000 U/g (1.6 mg/kg in the case of the clinical grade RecAP used).

In some aspects, the AP, e.g., RecAP, is administered to the patient if kidney injury, e.g., SA-AKI, is present and the kidney injury has been determined to be moderate to severe, or severe. Thus, in some aspects of the present disclosure, the methods disclosed herein comprise measuring severity of kidney injury, e.g., by determining glomerular filtration rate or a surrogate measure such as ECC or eGFR, prior to treatment with AP to determine whether the subject suffers moderate to severe kidney injury, or severe kidney injury.

In some aspects, kidney injury, e.g., SA-AKI, is classified as moderate to severe if baseline ECC is between about 15 ml/min and about 60 ml/min. In some aspects, kidney injury, e.g., SA-AKI, is classified as severe if baseline ECC is lower that about 15 ml/min. In other aspects, other diagnostic measurements can be used to determine the severity of the kidney injury, e.g. eGFR. In some aspects of the present disclosure, AP treatment is not administered to the subject if kidney injury is determined to be mild injury (e.g., if >60 ml/min baseline ECC) or if >60 ml/min baseline eGFR. With the term "or" in this respect is meant that either ECC or eGFR or both are within the defined range or below or beyond the defined threshold. As can be appreciated by the person skilled in the art, ECC and eGFR are correlated and a person having an ECC of <15 ml/min, for instance, is likely to (also) have an eGFR of <15 ml/min as well and vice versa. The same holds true for an ECC of >60 ml/min in respect of eGFR of >60 ml/min and an ECC of between 15-60 ml/min in respect of eGFR of between 15-60 ml/min. Nevertheless, there may be some differences between ECC and eGFR values and either one, preferably eGFR, may be used for determining whether a patient may or may not benefit from administration of AP.

In some aspects, an AP, e.g., RecAP, is administered prophylactically. In some aspects, the methods disclosed herein comprise administering at least one dose of AP, e.g., RecAP, to the subject wherein each dose is least 500 U/kg (0.8 mg/kg for the clinical grade RecAP used) or 1000 U/kg (1.6 mg/kg for the clinical grade RecAP used). In some specific aspects, the dosage regimen comprises administering 0.5 mg/kg to 2 mg/kg of an AP, e.g., RecAP, by intravenous infusion, in daily doses, for at least three days. In some specific aspects, the dosage regimen comprises administering 0.5 mg/kg to 2 mg/kg of an AP, e.g., RecAP, by intravenous infusion, in daily doses, for at least three days.

In order that the present disclosure can be more readily understood, certain terms are first defined. Additional definitions are set forth throughout the detailed description.

I. Definitions

In this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Wherever aspects are described herein with the language "comprising," otherwise analogous aspects described in terms of "consisting of" and/or "consisting essentially of" are also provided.

The term "about" as used in connection with a numerical value throughout the specification and the claims denotes an interval of accuracy, familiar and acceptable to a person skilled in the art. In general, such interval of accuracy is ±15%.

Unless defined otherwise, all technical and scientific terms used herein have the same meaning as commonly understood by one of ordinary skill in the art to which this disclosure is related.

Units, prefixes, and symbols are denoted in their Système International de Unites (SI) accepted form.

Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

As used herein the terms "treat," "treatment," or "treatment of" refers to (i) reducing the potential or risk for a disease or disorder, e.g., AKI (e.g., SA-AKI), (ii) reducing the occurrence of a disease or disorder, e.g., AKI (e.g., SA-AKI), (iii) reducing the severity (e.g., ameliorating the symptoms) of a disease or disorder, e.g., AKI (e.g., SA-AKI), or (iv) a combination thereof.

For example, treating can refer to the ability of a therapy when administered to a subject, to prevent or reduce the risk of kidney injury, e.g., SA-AKI, from occurring (for example, in subjects diagnosed with sepsis or at a risk for sepsis) and/or to cure or to alleviate symptoms, signs, or causes of kidney injure, e.g., SA-AKI. Treating also refers to mitigating or decreasing at least one clinical symptom and/or inhibition or delay in the progression of the condition and/or prevention or delay of the onset of a disease or illness when compared with a non-treated (or placebo treated) group. Thus, the terms "treat," "treating" or "treatment of" (or grammatically equivalent terms) refer to both prophylactic and therapeutic treatment regimes. In case of renal disease, it is preferred that subjects, after being treated with an AP with a method as disclosed herein improve in renal function or less decline in renal function, relative to subjects that have not been treated with said AP.

As used herein, the term "preserving" includes preventing a reduction, slowing down a reduction, stopping a reduction and/or at least partly reversing a reduction of a renal function. The term "increasing" is not necessarily limited to increasing said renal function to a value equal to or higher than that before said treatment occurred. It includes partly restoring renal function.

The term "treatment with a risk of decreasing renal function" is typically used to refer to a treatment which bears the risk that renal function is reduced by said treatment when comparing the value of at least one renal related parameter to a recognized or average (laboratory) value of said parameter, or by comparing said parameter to the value before said treatment is performed. If, for example, the amount of protein in the urine of a subject, preferably a human being is significantly above a recognized or average (laboratory) value, said renal function is said to be "decreased." The corresponding analysis can be performed in a laboratory but also in a home setting. For example, since September 2006 the Dutch "Nierstichting" has introduced a simple test (named Kidney check ("Niercheck")) which can be performed at home to test whether the kidneys function properly. This test is for instance directed to the amount of protein in the urine.

The terms "subject" or "patient" as used herein refer to any subject, particularly a mammalian subject, for whom therapy or prognosis of kidney injury, e.g., SA-AKI is desired. As used herein, the terms "subject" or "patient" include any human or nonhuman animal. As used herein, phrases such as "a patient having SA-AKI" or a "patient having sepsis" includes subjects, such as mammalian subjects, that would benefit from the administration of a therapy with AP, as disclosed herein.

In some aspects of the present disclosure, a subject is a naïve subject. A naïve subject is a subject that has not been administered a therapy, for example a therapeutic agent. In some aspects, a naïve subject has not been treated with a therapeutic agent prior to being diagnosed with kidney injury, e.g., SA-AKI, or a disease or condition (e.g., sepsis) that can lead to kidney injury.

In another aspect, a subject has received therapy and/or one or more doses of a therapeutic agent prior to being diagnosed as having kidney injury, e.g., SA-AKI, or a disease or condition (e.g., sepsis) that can lead to kidney injury.

In some aspects, a subject can be administered at least one therapeutically effective dose of an AP, e.g., RecAP, if the subject's baseline ECC or eGFR is below a predetermined ECC or eGFR threshold level, or if the baseline ECC or eGFR is above a predetermined ECC or eGFR threshold level, or if the baseline ECC or eGFR is within a predetermined range.

The terms "therapeutic agent" and "drug" as used herein also refer to any therapeutically active substance that is administered to a subject having a disease or disorder, e.g., kidney injury, e.g., SA-AKI, or a disease or condition (e.g., sepsis) that can lead to kidney injury to produce a desired, usually beneficial, effect. A therapeutic agent can also be a pro-drug, which metabolizes into the desired therapeutically active substance when administered to a subject. In some aspects, the therapeutic agent is a prophylactic agent. In addition, a therapeutic agent can be pharmaceutically formulated. A therapeutic agent can also be or comprise a radioactive isotope or agent activated by some other form of energy such as light or ultrasonic energy, or by other circulating molecules that can be systemically administered.

In some aspects of the present disclosure, a therapeutic agent for the treatment, prevention, or amelioration of the symptom of kidney injury, e.g., SA-AKI, or a disease or condition (e.g., sepsis) that can lead to kidney injury can comprise an AP, e.g., RecAP; alone or in combination with one or more standard therapeutic agents generally used for the treatment of kidney injury, e.g., SA-AKI, or a disease or condition (e.g., sepsis) that can lead to kidney injury.

A "therapeutically effective" amount as used herein is an amount of therapeutic agent that provides some improvement or benefit to a subject having a disease or disorder, e.g., kidney injury, e.g., SA-AKI, or a disease or condition (e.g., sepsis) that can lead to kidney injury. Thus, a "therapeutically effective" amount is an amount that provides some alleviation, mitigation, and/or decrease in at least one clinical symptom of a disease or disorder, e.g., kidney injury, e.g., SA-AKI, or a disease or condition (e.g., sepsis) that can lead to kidney injury.

Clinical symptoms associated with kidney injury, e.g., SA-AKI, or a disease or condition (e.g., sepsis) that can lead to kidney injury that can be treated by the compositions, methods, as specific dosage regimens of the disclosure are well known to those skilled in the art. Further, those skilled in the art will appreciate that the therapeutic effects need not be complete or curative, as long as some benefit is provided to the subject. In some aspects, the term "therapeutically effective" refers to an amount of a therapeutic agent therapeutic agent that is capable of altering biomarker levels, e.g., ECC or eGFR in a patient in need thereof.

As used herein, a "sufficient amount" or "an amount sufficient to" achieve a particular result in a patient having a disease or disorder, e.g., kidney injury, e.g., SA-AKI, or a disease or condition (e.g., sepsis) that can lead to kidney injury refers to an amount of a therapeutic agent (e.g., an AP such as RecAP) that is effective to produce a desired effect, which is optionally a therapeutic effect (i.e., by administration of a therapeutically effective amount). In some aspects, such particular result is an improvement in kidney function or an increase in survival.

As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer a therapy to prevent, treat, or ameliorate the symptoms of a disease or disorder, e.g., kidney injury, e.g., SA-AKI, or a disease or condition (e.g., sepsis) that can lead to kidney injury. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy (e.g., an AP such as RecAP), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition a healthcare benefits provides can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, or other related activities.

II. Treatment of Acute Kidney Injury with AP

In certain aspects, the present disclosure is related to methods for preserving or improving kidney in populations of subjects, in particular, SA-AKI patients, that have been determined to respond particularly well to treatment with AP.

The STOP-AKI study has identified statistically significant correlations between thresholds corresponding to degrees of severity of kidney injury and improvements in kidney function (as evidenced by improved creatinine clearance with respect to placebo) and long term survival. As discussed above, stratifying patients in the STOP-AKI clinical trial according to, e.g., markers of kidney function (e.g., ECC or eGFR) has identified particular effects of AP administration on specific subgroups. The parameter or parameters defining each of these subgroups (e.g., a series of thresholds, such as ECC or eGFR thresholds) can be used, e.g., to personalize AP therapy to specific subgroups, to selected patients for treatment, to make decisions related to the AP treatment (e.g., modify dosing or dosage schedule), or to evaluate the likelihood of a positive outcome.

Accordingly, in some aspects, the methods disclosed herein relate to the administration of AP, e.g., RecAP, to a subject determined to have either moderate to severe kidney injury, or with severe kidney injury, e.g., due to SA-AKI, comprising administering an AP such as RecAP to the subject. Administration of AP is particularly effective when administered to subjects having moderate to severe kidney injury or severe kidney injury at doses of at least 500 U/kg. AP was most effective when administered at doses of at least 1,000 U/kg.

As used herein, the term "severe kidney injury" refers to kidney damage or impairment of kidney function resulting in a creatinine clearance rate lower than 15 ml/min. As used herein, the term "moderate to severe kidney injury" refers to kidney damage or impairment of kidney function resulting in a creatinine clearance rate of 15 ml/min to 60 ml/min. As used herein, the term "mild kidney injury" refers to kidney damage or impairment of kidney function resulting in a creatinine clearance rate of higher than 60 ml/min. As used herein the term "baseline ECC" refers to the endogenous creatinine clearance rate at baseline. As used herein the term "baseline eGFR" refers to the estimated glomerular filtration rate at baseline. Both ECC and eGFR are estimations of the actual glomerular filtration rate as measurement of kidney function.

In some aspects, the present disclosure provides, e.g., a method to treat sepsis-associated acute kidney disease injury (SA-AKI) in a subject in need thereof, or alkaline phosphatase (AP) for use in a method to treat sepsis-associated acute kidney disease injury (SA-AKI) in a subject in need thereof, wherein the method comprises administering an effective amount of alkaline phosphatase (AP) to said subject, wherein
  (i) the subject has an ECC (endogenous creatinine clearance) rate ≤60 ml/min or an eGFR ≤60 ml/min prior to the treatment with AP (e.g., RecAP);
  (ii) the AP is administered in at least one dose of about 500 U/kg to about 2,000 U/kg; and,
  (iii) the administration of the AP results in an increase in renal function.

In some aspects, the subject with an ECC rate ≤60 ml/min prior to the treatment with AP has moderate kidney injury (15-60 ml/min baseline ECC). In some aspects, the subject with an ECC rate ≤60 ml/min prior to the treatment with AP has severe kidney injury (<15 ml/min baseline ECC). In some aspects, the subject with an ECC rate ≤60 ml/min prior to the treatment with AP does not have mild kidney injury (>60 ml/min baseline ECC). In some aspects the subject with an eGFR ≤60 ml/min prior to the treatment with AP has 15-60 ml/min baseline eGFR. In some aspects, the subject with an eGFR ≤60 ml/min prior to the treatment with AP has <15 ml/min baseline eGFR. In some aspects, the subject with an eGFR ≤60 ml/min prior to the treatment with AP does not have >60 ml/min baseline eGFR.

In some aspects, the AP (e.g., RecAP) is administered as doses of at least about 500 U/kg, at least about 600 U/kg, at least about 700 U/kg, at least about 800 U/kg, at least about 900 U/kg, at least about 1000 U/kg, at least about 1100 U/kg, at least about 1200 U/kg, at least about 1300 U/kg, at least about 1400 U/kg, at least about 1500 U/kg, at least about 1600 U/kg, at least about 1700 U/kg, at least about 1800 U/kg, at least about 1900 U/kg, or at least about 2000 U/kg per dose. In some aspects, the AP (e.g. RecAP) is administered as doses above 2000 U/kg per dose. In some aspects, the AP (e.g., RecAP) is administered as doses below 500 U/kg per dose.

In some aspects, the AP (e.g., RecAP) is administered at a dose between about 500 U/kg and about 1500 U/kg, between about 600 U/kg and about 1400 U/kg, between about 700 U/kg and about 1300 U/kg, between about 800 U/kg and about 1200 U/kg, or between about 900 U/kg and about 1100 U/kg. In some specific aspects, AP is administered as about 1000 U/kg doses.

In some aspects, the AP is a human AP. In some aspects, the AP is a recombinant AP. In some aspects, the AP is a chimeric AP. In a particular aspects, the chimeric AP is RecAP (SEQ ID NO: 1). In some aspects, an AP disclosed herein has at least about 70%, at least about 75%, at least about 80%, at least about 85%, at least about 90%, at least about 95%, at least about 96%, at least about 97%, at least about 98%, or at least about 99% sequence identity to the amino acid sequence of SEQ ID NO:1. In some aspects, the AP is a functional fragment (i.e., a fragment of the AP, e.g., AP conserving at least about 10%, at least about 20%, at least about 30%, at least 40%, at least about 50%, at least about 60%, at least 70%, at least about 80%, or at least about 90% of the AP activity of the corresponding full length AP). In some aspects, the AP is a variant or a derivative of an AP disclosed herein. Other AP that can be used according to, or for the methods disclosed herein are discussed in detail below.

In some aspects, the AP is RecAP (e.g., the clinical grade RecAP used in the present disclosure), and it is administered at a dose of at least about 0.1 mg/kg, at least about 0.2 mg/kg, at least about 0.3 mg/kg, at least about 0.4 mg/kg, at least about 0.5 mg/kg, at least about 0.6 mg/kg, at least about 0.7 mg/kg, at least about 0.8 mg/kg, at least about 0.9 mg/kg, at least about 1 mg/kg, at least about 1.1 mg/kg, at least about 1.3 mg/kg, at least about 1.4 mg/kg, at least about 1.5 mg/kg, at least about 1.6 mg/kg, at least about 1.7 mg/kg, at least about 1.8 mg/kg, at least about 1.9 mg/kg, at least about 2 mg/kg, at least about 2.1 mg/kg, at least about 2.2 mg/kg, at least about 2.3 mg/kg, or at least about 2.4/kg per dose. In some aspects, the AP is administered as doses above 2.4 mg/kg per dose. In some aspects, the AP is RecAP (e.g., the clinical grade RecAP used in the present disclosure), and it is administered at a dose of at least about 100 U/kg, at least about 200 U/kg, at least about 300 U/kg, at least about 400 U/kg, at least about 500 U/kg, at least about 600 U/kg, at least about 700 U/kg, at least about 800 U/kg, at least about 900 U/kg, at least about 1000 U/kg, at least about 1100 U/kg, at least about 1200 U/kg, at least about 1300 U/kg, at least about 1400 U/kg, at least about 1500 U/kg, at least about 1600 U/kg, at least about 1700 U/kg, at least about 1800 U/kg, at least about 1900 U/kg, or at least about 2000 U/kg., the AP is RecAP, and it is administered at a dose below 100 U/kg., the AP is RecAP, and it is administered at a dose above 2000 U/kg.

In some aspects, the AP is RecAP (e.g., the clinical grade RecAP used in the present disclosure) and it is administered at a dose between about 0.8 mg/kg and about 2.4 mg/kg, between about 0.9 mg/kg and about 2.3 mg/kg, between about 1 mg/kg and about 2.2 mg/kg, between about 1.1 mg/kg and about 2.1 mg/kg, between about 1.2 mg/kg and about 2 mg/kg, between about 1.3 mg/kg and about 1.9 mg/kg, between about 1.4 mg/kg and about 1.8 mg/kg, or between about 1.5 mg/kg and about 1.7 mg/kg. In some specific aspects, AP is administered as about 1.6 mg/kg doses.

In some aspects, the AP is RecAP (e.g., the clinical grade RecAP used in the present disclosure) and it has a specific activity of at least about 100 U/mg, at least about 200 U/mg, at least about 300 U/mg, at least about 400 U/mg, at least about 500 U/mg, at least about 600 U/mg, at least about 700 U/mg, at least about 800 U/mg, at least about 900 U/mg, at least about 1000 U/mg, at least about 1100 U/mg, at least about 1200 U/mg, at least about 1300 U/mg, at least about 1400 U/mg, at least about 1500 U/mg, at least about 1600 U/mg, at least about 1700 U/mg, at least about 1800 U/mg, at least about 1900 U/mg, or at least about 2000 U/mg.

In some aspects, the AP is RecAP (e.g., the clinical grade RecAP used in the present disclosure) and it has a specific activity of about 1000 U:1.6 mg. In some aspects, the AP is RecAP and it has a specific activity between about 600 U/mg and about 700 U/mg, or between about 500 U/mg and about 800 U/mg, or between about 400 U/mg and about 900 U/mg, or between about 300 U/mg and about 1000 U/mg, or between about 200 U/mg and about 1100 U/mg, or between 100 U/mg and about 1200 U/mg. In some aspects, the AP is RecAP and it has a specific activity below 100 U/mg. In some aspects, the AP is RecAP and it has a specific activity above 1200 U/mg.

In some aspects, only one dose of AP (e.g., RecAP) is administered per treatment (e.g., one dose per day for 1-7 days). In other aspects, more than one dose of AP is administered. In some aspects, two, three, four, five, six, seven, eight, nine, 10, 11, 12, 13, 14, 15, 16, 17, 18, 19, 20, or 21 doses of AP are administered (e.g., at least two doses per day for 1-7 days).

In some aspects, the AP doses are administered daily. In other aspects, AP doses are administered every 2, 3, 4, 5, 6 or 7 days.

In some aspects, a single dose is administered every day. In some aspects, 2, 3, or more doses are administered every day.

In some aspects, the treatment with AP is less than about 4 days. In some aspects, the treatment with AP is less than 3 days, less than 2 days, or less than 1 day.

In a particular aspect, the AP is administered as a daily about 1000 U/kg dose administered in 3 consecutive days. In some particular aspects, when the AP is RecAP, the AP is administered as daily 1.6 mg/kg doses administered in 3 consecutive days. In some aspects, each AP, e.g., RecAP (e.g., the clinical grade RecAP used in the present disclosure), dose is between about 0.10 mg/kg and about 3 mg/kg, or between about 0.20 mg/kg and about 2.9 mg/kg, or between about 0.3 mg/kg and about 2.8 mg/kg, or between about 0.4 mg/kg and about 2.7 mg/kg, or between about 0.5 mg/kg and about 2.6 mg/kg, or between about 0.6 mg/kg and about 2.5 mg/kg, or between about 0.7 mg/kg and about 2.4 mg/kg, or between about 0.8 mg/kg and about 2.3 mg/kg, or between about 0.9 mg/kg and about 2.2 mg/kg, or between about 1 mg and about 2.1 mg/kg, or between about 1.1 mg/kg and about 2 mg/kg, or between about 1.2 mg/kg and about 1.9 mg/kg, or between about 1.3 mg/kg and about 1.8 mg/kg, or between about 1.4 mg/kg and about 1.7 mg/kg. In some aspects, each AP, e.g., RecAP, dose comprises at least about 0.1 mg AP/kg, at least about 0.2 mg AP/kg, at least about 0.3 mg AP/kg, at least about 0.4 mg AP/kg, at least about 0.5 mg AP/kg, at least about 0.6 mg AP/kg, at least about 0.7 mg AP/kg, at least about 0.8 mg AP/kg, at least about 0.9 mg AP/kg, at least about 1 mg AP/kg, at least about 1.1 mg AP/kg, at least about 1.2 mg AP/kg, at least about 1.3 mg AP/kg, at least about 1.4 mg AP/kg, at least about 1.5 mg AP/kg, at least about 1.6 mg AP/kg, at least about 1.7 mg AP/kg, at least about 1.8 mg AP/kg, at least about 1.9 mg AP/kg, at least about 2 mg AP/kg, at least about 2.1 mg AP/kg, at least about 2.2 mg AP/kg, at least about 2.3 mg AP/kg, at least about 2.4 mg AP/kg, at least about 2.5 mg AP/kg, at least about 2.6 mg AP/kg, at least about 2.6 mg AP/kg, at least about 2.7 mg AP/kg, at least about 2.8 mg AP/kg, at least about 2.9 mg AP/kg, or at least about 3 mg AP/kg.

The AP may be administered via different routes, for example intravenously, rectally, bronchially or orally. In some specific aspects, the AP is administered intravenously, e.g., via intravenous infusion. In some aspects, AP is administered intravenously via continuous infusion.

Although short term preservation of renal function can have immediate life-saving consequences, it is preferred that the effect of AP on the renal function is long lasting.

ECC can be determined by methods known in the art. One method of calculation of ECC is to collect a urine sample (usually collected for 24-hours) to determine the amount of creatinine that was removed from the blood over a given time interval. If one removes, for instance, 1440 mg in 24 hours, this is equivalent to removing 1 mg/min. If the blood concentration is 0.01 mg/mL (1 mg/dL), then the creatinine clearance is said to be 100 mL/min. This is because, in order to excrete 1 mg of creatinine, 100 mL of blood containing 0.01 mg/mL would need to have been cleared.

eGFR can be determined by methods known in the art. Either the Modification of Diet in Renal Disease (MDRD) Study equation or the Chronic Kidney Disease Epidemiology Collaboration (CKD-EPI) equation can be used, preferably the CKD-EPI equation. The skilled person is aware how to estimate eGFR according to either method, for instance by using a website for calculation of the eGFR as provided, for instance, by the national kidney foundation (kidney.org).

In some aspects, the administration of AP to the subject according to the methods disclosed herein is capable of improving many renal function related parameters, such as BUN, ECC, eGFR, and serum creatinine levels in the subject.

In some aspects, the administration of AP (e.g., RecAP) to the subject results in an increase in renal function comprising an increase in ECC or eGFR with respect to ECC or eGFR, respectively, in the absence of treatment. In some aspects, the increase in ECC or eGFR is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 ml/min with respect to ECC or eGFR in the absence of treatment.

In some aspects, the administration of AP (e.g., RecAP) to the subject results in an increase in renal function comprising an increase in ECC or eGFR with respect to baseline ECC or eGFR, respectively. In some aspects, the increase in ECC or eGFR is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 ml/min with respect to baseline ECC or eGFR, respectively.

In some aspects, the increase in renal function is observed 1, 2, 3, 4, 5, 6, 7, 8, 9, 10, 11, 12, 13, 14, 15, 16, 17, 18, 19, 20, 21, 22, 23, 24, 25, 26, 27, or 28 days after AP administration.

ECC can be used as an approximation of glomerular filtration rate (GFR). However, other parameters can also be assessed in order to determine renal function, e.g., GFR, eGFR, serum creatinine levels, electrolyte derangement, amount of produced urine, BUN, calcium levels, phosphorous levels, albumin levels, and/or red and white blood cells in urine. Another test that can be performed to determine renal function is, e.g., a complete blood count with differential. It is also possible to analyze a urine sample on the presence of absence of an RNA molecule. RNA in urine can be obtained from urine-secreted renal cells. In some aspects, the RNA is an mRNA molecule such iNOS mRNA.

In some aspects, the administration of AP (e.g., RecAP) to the subject results in an increase of the survival rate of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40% compared to the survival rate in the absence of AP treatment.

Conversely, the administration of AP (e.g., RecAP) to the subject results in a decrease of the mortality rate of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40% compared to the mortality rate in the absence of AP treatment.

In some aspects of the methods disclosed herein, AP (e.g., RecAP) is administered to the subject only if sepsis has been detected less than 96 hours prior to the decision to initiate the treatment. In other aspects, AP is administered only if sepsis was detected less than 72 hours prior to SA-AKI detection.

In some aspects of the present disclosure, treatment with AP is initiated within 24 hours after sepsis is detected. The presence of sepsis can be detected, e.g., as disclosed in the Examples section of this application. In some aspects of the present disclosure, treatment with AP is administered to a subject at risk of sepsis in order to prevent reduction in kidney function.

In some aspects, treatment is initiated within 24 hours after SA-AKI is detected.

In some aspects of the methods disclosed herein, the administration of at least one dose of AP results in a shortening of duration or cessation of renal replacement therapy (RRT) in a subject undergoing RRT.

In some aspects of the methods disclosed herein, the administration of at least one dose of AP results in the preservation or increase of glomerular filtration rate (GFR) in the subject. GFR can be assessed in several ways, e.g., by inulin or chromium EDTA clearance, or an approximation of GFR can be made, for instance by calculating ECC. This is calculated from a measured 24 hour urine volume, the urine creatinine level, and the serum creatinine level. The GFR can also be estimated (eGFR), based on serum creatinine.

In some aspects of the methods disclosed herein, the administration of AP results in an increase of renal function or prevents the reduction of renal function below a critical threshold which would preclude the administration of a certain treatment, e.g., the administration of an antibiotic to treat sepsis. Accordingly, in some aspect, AP administration is able to prevent reduction of the renal function below a critical threshold and thus enables such person to receive the treatment. Thus, in some aspects, an indicator of renal function (e.g., ECC or eGFR) is determined prior to administering AP for preserving renal function in order to determine the risk that the renal function of said person is reduced below a certain threshold level.

In some aspect, the methods disclosed herein comprise detecting changes in markers of kidney function, e.g., ECC, eGFR, or BUN clearance, alone or in combination with the detection of changes in the levels of one, two, three, or more biomarkers.

In some aspects, the methods disclosed herein comprise predicting an increased clinical response to therapy with AP, e.g., RecAP, based on detected kidney function parameters (e.g., baseline ECC or baseline eGFR). In some aspects, the methods of the present disclosure comprise evaluating whether a kidney function parameter (e.g., baseline ECC or baseline eGFR) falls within a certain range, or it's above or below a certain threshold (e.g., ECC or eGFR threshold for severity of kidney injury). Thus, if, e.g., the kidney function parameter (e.g., baseline ECC or baseline eGFR), alone or in combination with other biomarkers, indicates that the patient will benefit from therapy with AP, then therapy could commence, or be maintained, or be modified (e.g., increasing or decreasing dosage, or increasing or decreasing frequency of doses).

Conversely, if, e.g., the kidney function parameter (e.g., baseline ECC or baseline eGFR), alone or in combination with other biomarkers, indicates that the patient will not benefit from therapy with AP, then therapy could be discontinued, temporarily suspended, modified (e.g., increasing or decreasing dosage or increasing or decreasing frequency of doses), etc.

In other words, specific levels of a kidney function parameter (e.g., baseline ECC or baseline eGFR) alone or in combination with other molecular or clinical biomarkers are correlated with clinical efficacy of AP therapy and useful to predict clinical outcomes in specific populations of patients suffering from sepsis and/or SA-AKI.

For some jurisdictions, the invention provides alkaline phosphatase (AP) for use in a method to treat sepsis-associated acute kidney disease injury (SA-AKI) comprising administering an effective amount of alkaline phosphatase (AP) to said subject, wherein
(i) the subject has an ECC (endogenous creatinine clearance) rate ≤60 ml/min or eGFR (estimated glomerular filtration rate) ≤60 ml/min prior to the treatment with AP, and
(ii) the AP is to be administered in at least one 300 U/kg to 2,000 U/kg dose. In a preferred embodiment, the subject has moderate kidney injury (15-60 ml/min ECC) prior to the treatment with AP. In another preferred embodiment, the subject has severe kidney injury (<15 ml/min ECC) prior to the treatment with AP. In a preferred embodiment, the subject has 15-60 ml/min eGFR prior to the treatment with AP. In another preferred embodiment, the subject has <15 ml/min eGFR prior to the treatment with AP.

Also provided is an AP for use according to the invention, wherein the subject does not have mild kidney injury (>60 ml/min ECC) prior to the treatment with AP. Also provided is an AP for use according to the invention, wherein the subject does not have >60 ml/min eGFR prior to the treatment with AP.

In one preferred embodiment, an AP for use according to the invention is provided, wherein the AP is a human AP.

In a preferred embodiment, the AP is a recombinant AP, preferably chimeric, more preferably having at least 80%, at least 85%, at least 90%, at least 95%, at least 96%, at least 97%, at least 98%, at least 99%, or at least 100% sequence identity to the amino acid sequence of RecAP (SEQ ID NO: 1).

In a preferred embodiment, an AP for use according to the invention is provided, wherein the administration of AP leads to an increase in renal function and wherein the increase in renal function comprises an increase in ECC with respect to ECC in the absence of treatment or an increase in eGFR with respect to eGFR in the absence of treatment.

In one preferred embodiment, an AP for use according to the invention is provided, wherein sepsis is detected less than 96 hours prior to AP administration.

In one preferred embodiment, an AP for use according to the invention is provided, wherein the sepsis is detected less than 72 hours prior to SA-AKI detection.

Preferably, treatment is initiated within 24 hours after sepsis is detected and/or after SA-AKI is detected.

In a preferred embodiment, AP for use according to the invention is provided, wherein AP is administered once daily. In a preferred embodiment, AP is administered intravenously. In a preferred embodiment, AP is administered in three daily doses.

In a preferred embodiment, AP for use according to the invention is provided, wherein the AP is RecAP and the dose is between 0.06 mg/kg (and/or 375 U/kg) or 3.2 mg/kg (and/or 2,000 U/kg) of RecAP, preferably between 0.08 mg/kg (and/or 500 U/kg).

In one preferred embodiment, AP for use according to the invention is provided, wherein the administration of at least one dose of AP results in a shortening of duration or cessation of renal replacement therapy (RRT) in a subject undergoing RRT.

In one preferred embodiment, AP for use according to the invention is provided, wherein the administration of at least one dose of AP results in the preservation or increase of glomerular filtration rate (GFR) in the subject.

The term "biomarker" as used herein refers to a factor that is a distinctive indicator of a biological process, biological event, and/or pathologic condition, e.g., a predictor of clinical response to treatment with AP, e.g., RecAP. As used herein, the term biomarker encompasses both clinical markers and molecular biomarkers (biological markers). Thus, in the context of the present disclosure, the term "biomarker" encompasses, e.g., "biological biomarkers" or "molecular biomarkers." In some aspects, the biological or molecular biomarkers used to evaluate kidney function comprise markers of liver function (e.g., alanine aminotransferase, aspartate aminotransferase, gamma-glutamyl transferase, bilirubin, or LDH), C-reactive protein (CRP), interleukin 6 (IL-6), interleukin 18 (IL-18), lipopolysaccharide binding protein, kidney injury molecule 1 (KIM-1) or combinations thereof.

As disclosed above, the term "biomarker" also encompasses "clinical biomarkers," also referred to as "clinical status markers," that can be predictive of response to biological therapies, for example, gender, age, concomitant drugs, smoking status, body mass index (BMI), etc.

As discussed above, a cut-off approach based on baseline ECC values is applied to classify AKI as "severe kidney injury," "moderate to severe kidney injury," or "mild kidney injury." The differences in ECC levels observed, e.g., in subjects "severe kidney injury," "moderate to severe kidney injury," or "mild kidney injury," can be applied to predicting clinical outcomes when the patients are treated with an AP, for example, RecAP. Similarly, eGFR may be used, and preferably is used, for a cut-off approach. Thus, if a subject's ECC rate or eGFR at baseline are below a certain threshold (e.g., 60 ml/min or 15 ml/min), that subject would become a candidate for treatment with a certain AP therapy, e.g., therapy with a certain AP regimen comprising one or more doses of RecAP.

In some aspects, the mere determination that the ECC rate or the eGFR is below a predetermined threshold level would suffice to identify a subject as a candidate for treatment with a certain AP therapy, e.g., therapy with RecAP. Thus, in some aspects of the methods disclosed herein, ECC rates or eGFR can be used alone. However, in other aspects, the ECC rate or eGFR can be combined with each other or with other measures of kidney function (e.g., BUN clearance) and/or molecular or clinical biomarkers, such KIM-1 levels.

These findings can be applied, for example, to devising new methods of determining treatment (e.g., by selecting patients as candidates for a certain AP therapy), methods of treating a decrease in kidney function, preventing a decrease in kidney function, increasing kidney function, or preserving kidney function (e.g., to treat SA-AKI), methods of monitoring efficacy of an AP treatment, or methods to adjust formulations, dosage regimens, or routes of administration.

The methods disclosed herein include prescribing, initiating, and/or altering prophylaxis and/or treatment, e.g., for SA-AKI, based at least in part on a subject's ECC or eGFR (or another kidney function parameter), alone or in combination with one or more additional biomarkers.

The present disclosure provides a method of determining whether to treat a patient having SA-AKI with a therapeutic regimen comprising the administration of an AP wherein the method comprises: (a) measuring or instructing a clinical laboratory to measure ECC or eGFR (or another kidney function parameter), and optionally levels of additional biomarkers such as KIM-1 in a sample taken from the patient, and (b) treating or instructing a healthcare provider to treat the patient, or suspending the treatment, not initiating the treatment, denying the treatment, or instructing a healthcare provider to suspend, not initiate, or deny the treatment with a therapeutic regimen comprising the administration of an AP, e.g., RecAP, if the patient is determined to have higher or lower ECC or eGFR (or another kidney function parameter), and optionally levels of additional biomarkers such as KIM-1 in the sample compared to each biomarker predetermined threshold level or levels, or compared to each biomarker level or levels in one or more controls. Also provided is a method of determining whether a patient having SA-AKI is likely to respond to a therapeutic regimen comprising the administration of an AP, wherein the method comprises: (a) measuring or instructing a clinical laboratory to measure ECC or eGFR (or another kidney function parameter), and optionally levels of additional biomarkers such as KIM-1 in a sample taken from the patient, and (b) determining that the patient is likely to respond, or is not likely to respond, to the treatment with a therapeutic regimen comprising the administration of an AP, e.g., RecAP, if the patient is determined to have higher or lower ECC (or another kidney function parameter), and optionally levels of additional biomarkers such as KIM-1 in the sample compared to each biomarker predetermined threshold level or levels, or compared to each biomarker level or levels in one or more controls. In one preferred aspect ECC is measured. In another preferred aspect eGFR is measured.

In one aspect, the disclosure provides a method of determining whether to treat a patient having SA-AKI with a therapeutic regimen comprising the administration of an AP wherein the method comprises: (a) measuring or instructing a clinical laboratory to measure ECC or eGFR (or another kidney function parameter) and optionally levels of additional biomarkers such as KIM-1 in a sample taken from the patient, and (b) treating or instructing a healthcare provider to treat the patient with a therapeutic regimen comprising the administration of an AP if the patient is determined to have lower or decreased ECC or eGFR (or another kidney function parameter), and higher or increased levels of at least one optional additional biomarker such as KIM-1 in the sample compared to a predetermined biomarker threshold level or levels, or compared to a biomarker level or levels in one or more controls. Also provided is a method of determining whether a patient having SA-AKI is likely to respond to a therapeutic regimen comprising the administration of an AP, wherein the method comprises: (a) measuring or instructing a clinical laboratory to measure ECC or eGFR (or another kidney function parameter) and optionally levels of additional biomarkers such as KIM-1 in a sample taken from the patient, and (b) determining that the patient is likely to respond to a therapeutic regimen comprising the administration of an AP if the patient is determined to have lower or decreased ECC or eGFR (or another kidney function parameter), and higher or increased levels of at least one optional additional biomarker such as KIM-1 in the sample compared to a predetermined biomarker threshold level or levels, or compared to a biomarker level or levels in one or more controls.

In one aspect, the disclosure provides a method of determining whether to treat a patient having SA-AKI with a therapeutic regimen comprising the administration of an AP wherein the method comprises (a) measuring or instructing a clinical laboratory to measure the ECC or eGFR (or another kidney function parameter) and optionally levels of additional biomarkers such KIM-1 in a sample taken from the patient, and (b) suspending the treatment, not initiating treatment, denying the treatment, or instructing a healthcare provider to suspend, not initiate, or deny the treatment of the patient with a therapeutic regimen comprising the administration of an AP, e.g., RecAP, to the patient if the patient is determined to have higher or increased ECC or eGFR (or another kidney function parameter), and lower or decreased levels of at least one optional additional biomarker such as KIM-1 in the sample compared to a predetermined biomarker threshold level or levels, or compared to a biomarker level or levels in one or more controls. Also provided is a method of determining whether to treat a patient having SA-AKI with a therapeutic regimen comprising the administration of an AP wherein the method comprises (a) measuring or instructing a clinical laboratory to measure the ECC or eGFR (or another kidney function parameter) and optionally levels of additional biomarkers such KIM-1 in a sample taken from the patient, and (b) determining that the patient is unlikely to respond to a therapeutic regimen comprising the administration of an AP, e.g., RecAP, to the patient if the patient is determined to have higher or increased ECC or eGFR (or another kidney function parameter), and lower or decreased levels of at least one optional additional biomarker such as KIM-1 in the sample compared to a predetermined biomarker threshold level or levels, or compared to a biomarker level or levels in one or more controls.

Also provided is a method of selecting a patient diagnosed with SA-AKI as a candidate for treatment with an AP, comprising (a) measuring or instructing a clinical laboratory to measure ECC or eGFR (or another kidney function parameter) and optionally levels of additional biomarkers such as KIM-1 in a sample taken from the patient, and (b) treating or instructing a healthcare provider to treat the patient with an AP if the patient is determined to have lower or decreased ECC or eGFR (or another kidney function parameter), and higher or increased levels of at least one optional additional biomarker such as KIM-1 in the sample compared to a predetermined threshold level or levels, or compared to a biomarker level or levels in one or more controls. Also provided is a method of selecting a patient diagnosed with SA-AKI as a candidate for treatment with an AP, comprising (a) measuring or instructing a clinical laboratory to measure ECC or eGFR (or another kidney function parameter) and optionally levels of additional biomarkers such as KIM-1 in a sample taken from the patient, and (b) determining that the patient is likely to respond to a treatment with AP if the patient is determined to have lower or decreased ECC or eGFR (or another kidney function parameter), and higher or increased levels of at least one optional additional biomarker such as KIM-1 in the sample compared to a predetermined threshold level or levels, or compared to a biomarker level or levels in one or more controls.

Also provided is a method of selecting a patient diagnosed with SA-AKI as a candidate for treatment with an AP comprising (a) measuring or instructing a clinical laboratory to measure ECC or eGFR (or another kidney function parameter) and optionally levels of additional biomarkers such KIM-1 in a sample taken from the patient, and (b) suspending the treatment, not initiating treatment, denying the treatment, or instructing a healthcare provider to suspend, not initiate, or deny the treatment of the patient with an AP, e.g., RecAP, to the patient if the patient is determined to have higher or increased ECC or eGFR (or another kidney function parameter), and lower or decreased levels of at least one optional additional biomarker such as KIM-1 in the sample compared to a predetermined threshold level or levels, or compared to a biomarker level or levels in one or more controls. Also provided is a method of selecting a patient diagnosed with SA-AKI as a candidate for treatment with an AP comprising (a) measuring or instructing a clinical laboratory to measure ECC or eGFR (or another kidney function parameter) and optionally levels of additional biomarkers such KIM-1 in a sample taken from the patient, and (b) determining that the patient is unlikely to respond to treatment with an AP, e.g., RecAP, if the patient is determined to have higher or increased ECC or eGFR (or another kidney function parameter), and lower or decreased levels of at least one optional additional biomarker such as KIM-1 in the sample compared to a predetermined threshold level or levels, or compared to a biomarker level or levels in one or more controls.

In some aspects, the methods disclosed can entail ordering and/or performing one or more additional assays. For example, the ECC or eGFR (or another kidney function parameter) determination assay may be repeated to rule out a false negative result, and/or one or more additional ECC or eGFR (or another kidney function parameter) determination assays may be performed to monitor the subject's status. Conversely, it may be desirable repeat the ECC or eGFR (or another kidney function parameter) determination assays to rule out a false positive result.

In some aspects, the predetermined ECC or eGFR threshold level is about 15 ml/min (threshold differentiating between severe kidney injure and moderate to severe kidney injury), or about 60 ml/min (threshold differentiating between moderate to severe kidney injury and mild kidney injury).

In some aspects, the presence of ECC or eGFR (or another kidney function parameter) above or below a predetermined threshold level in a patient with SA-AKI can be used in combination with one or more of clinical or molecular biomarkers specific for sepsis, or for the specific infection that lead to sepsis.

A person skilled in the art would understand that ECC or eGFR (or another kidney function parameter) can be used according to the methods disclosed herein, including but not limited to treatment, diagnostic, and monitoring methods, as a positive selector, i.e., a specific action would be taken (e.g., treating a patient) if the ECC or eGFR (or another kidney function parameter) value in a sample taken from the patient is below or above a predetermined ECC or eGFR (or another kidney function parameter) threshold level, or ECC or eGFR (or another kidney function parameter) is increased or decreased relative to the ECC or eGFR (or another kidney function parameter) in one or more controls.

A person skilled in the art would understand that ECC or eGFR (or another kidney function parameter) can be used according to the methods disclosed herein, including but not limited to treatment, diagnostic, and monitoring methods, as a negative selector, i.e., a specific action would not be taken (e.g., treating a patient) if ECC or eGFR (or another kidney function parameter) value in a sample taken from the patient is below or above a predetermined ECC or eGFR (or another kidney function parameter) threshold level, or ECC or eGFR (or another kidney function parameter) is increased or decreased relative to the ECC or eGFR (or another kidney function parameter) in one or more controls.

In one aspect, the disclosure includes methods to facilitate a determination by a healthcare provider, a healthcare benefits provider, or a clinical laboratory to as to whether a patient will benefit from treatment with an AP.

In one aspect, the methods disclosed herein include making a diagnosis, which may be a differential diagnosis, based at least in part on ECC or eGFR (or another kidney function parameter) of a patient. In some aspects, the methods disclosed herein include informing the subject of a result of the ECC or eGFR (or another kidney function parameter) determination assay and/or of a diagnosis based at least in part on ECC or eGFR (or another kidney function parameter). The patient can be informed verbally, in writing, and/or electronically. This diagnosis can also be recorded in a patient medical record.

The term "medical record" or "patient medical record" refers to an account of a patient's examination and/or treatment that typically includes one or more of the following: the patient's medical history and complaints, the physician's physical findings, the results of diagnostic tests and procedures, and patient medications and therapeutic procedures. A medical record is typically made by one or more physicians and/or physicians' assistants and it is a written, transcribed or otherwise recorded record and/or history of various illnesses or injuries requiring medical care, and/or inoculations, and/or allergies, and/or treatments, and/or prognosis, and/or frequently health information about parents, siblings, and/or occupation. The record may be reviewed by a physician in diagnosing the condition.

The medical record can be in paper form and/or can be maintained in a computer-readable medium. The medical record can be maintained by a laboratory, physician's office, a hospital, a healthcare maintenance organization, an insurance company, and/or a personal medical record website. In some aspects, a diagnosis, based at least in part on the measured ECC or eGFR, is recorded on or in a medical alert article such as a card, a worn article, and/or a radiofrequency identification (RFID) tag. As used herein, the term "worn article" refers to any article that can be worn on a subject's body, including, but not limited to, a tag, bracelet, necklace, arm band, or head band.

As used herein, the term "diagnosis" means detecting a disease or determining the stage or degree of a disease. Usually, a diagnosis of a disease is based on the evaluation of one or more factors and/or symptoms that are indicative of the disease. That is, a diagnosis can be made based on the presence, absence or amount of a factor which is indicative of presence or absence of the disease or disorder. Each factor or symptom that is considered to be indicative for the diagnosis of a particular disease does not need be exclusively related to the particular disease, e.g. there may be differential diagnoses that can be inferred from a diagnostic factor or symptom. Likewise, there may be instances where a factor or symptom that is indicative of a particular disease is present in an individual that does not have the particular disease.

The term "diagnosis" also encompasses determining the therapeutic effect of a drug therapy, e.g., AP therapy, or predicting the pattern of response to a drug therapy. The diagnostic methods may be used independently, or in combination with other diagnosing and/or staging methods known in the medical arts for a particular disease.

As used herein, the term "differential diagnosis" refers to the determination of which of two or more diseases with similar symptoms is likely responsible for a subject's symptom(s), based on an analysis of the clinical data. The term is also used to refer to the determination of whether a patient is susceptible to treatment with an AP depending on whether the measured ECC or eGFR (or another kidney function parameter) in a patient sample is above or below a predetermined threshold level, or elevated or decreased relative to the level in one or more controls.

The term "prognosis" as used herein refers to a prediction of the probable course and outcome of a clinical condition or disease, e.g., sepsis or SA-AKI. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease, e.g., sepsis or SA-AKI. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include increased kidney function, preservation of kidney function, increase in ECC or eGFR (or another kidney function parameter), and the like.

The disclosure includes methods of treating SA-AKI in a subject, or AP for use in a method of treating SA-AKI in a subject, based on the changes in expression of ECC (or another kidney function parameter). The disclosure provides a method of treating a patient having SA-AKI, or AP for use in a method of treating SA-AKI in a subject, wherein the method comprises: administering an AP to the patient if the patient is determined to have a lower or decreased ECC or eGFR (or another kidney function parameter) in one or more samples taken from the patient compared to predetermined ECC or eGFR (or another kidney function parameter) threshold levels, or compared to the ECC or eGFR (or another kidney function parameter) in one or more controls.

The disclosure also provides a method of treating a patient having SA-AKI, or AP for use in a method of treating a patient having SA-AKI, wherein the method comprises: (a) submitting a sample taken from the patient for measurement of ECC or eGFR (or another kidney function parameter) in the sample, and (b) administering an AP to the patient if the patient has a lower or decreased ECC or eGFR (or another kidney function parameter) in the sample taken compared to a predetermined ECC or eGFR (or another kidney function parameter) threshold level, or compared to the level of ECC or eGFR (or another kidney function parameter) in one or more controls.

Also provided is method of treating a patient having SA-AKI, or AP for use in a method of treating a patient having SA-AKI, wherein the method comprises: (a) submitting a sample taken from the patient for measurement of ECC or eGFR (or another kidney function parameter) in the sample, and (b) suspending or not initiating the administration of AP, e.g., RecAP, to the patient if the patients has a higher or increased ECC or eGFR (or another kidney function parameter) in the sample compared to a predetermined ECC or eGFR (or another kidney function parameter) threshold level, or compared to the level of ECC or eGFR (or another kidney function parameter) in one or more controls.

The disclosure also provides a method of treating a patient having SA-AKI, or AP for use in a method of treating a patient having SA-AKI, wherein the method comprises: (a) measuring ECC or eGFR (or another kidney function parameter) in a sample obtained from the patient; and (b) determining whether ECC or eGFR (or another kidney function parameter) values in the sample is higher or increased, or lower or decreased compared to a predetermined ECC or eGFR (or another kidney function parameter) threshold level. In some aspects the method further comprises administering or advising a healthcare provider to administer an AP, e.g., RecAP, to the patient if the patient is determined to have a lower or decreased ECC or eGFR (or another kidney function parameter) in the sample compared to a predetermined ECC or eGFR (or another kidney function parameter) threshold level, or compared to the ECC or eGFR (or another kidney function parameter) level in one or more controls; or to suspend or deny the administration of an AP if the patient is determined to have a higher or increased ECC or eGFR (or another kidney function parameter) level in the sample compared to a predetermined ECC or eGFR (or another kidney function parameter) threshold level, or compared to the ECC or eGFR (or another kidney function parameter) level in one or more controls.

Also provided is a method of treating a patient having SA-AKI, or AP for use in a method of treating a patient having SA-AKI, wherein the method comprises: (a) submitting a sample taken from a patient for measurement of ECC or eGFR (or another kidney function parameter) in a sample obtained from the patient, and (b) administering an AP to the patient if the patient is determined to have a lower or decreased ECC or eGFR (or another kidney function parameter) measured from the sample compared to a predetermined ECC or eGFR (or another kidney function parameter) threshold level, or compared to the ECC or eGFR (or another kidney function parameter) level in one or more controls; or suspending, not initiating, or denying the administration of an AP to the patient if the patient is determined to have a higher or increased ECC or eGFR in the sample compared to a predetermined ECC or eGFR (or another kidney function parameter) threshold level, or compared to the ECC or eGFR (or another kidney function parameter) level in one or more controls.

In some aspects, the sample is a urine sample obtained from the patient and is submitted for measurement of ECC or estimation of eGFR in the sample, for example, to a clinical laboratory.

In some aspects, the ECC or eGFR (or another kidney function parameter) determination assay is performed on a sample obtained from the patient, by the healthcare professional treating the patient. In some aspects, a sample is obtained from the patient and is submitted, e.g., to a clinical laboratory, for measurement of ECC or eGFR (or another kidney function parameter) in the sample according to the healthcare professional's instructions. In some aspects, the clinical laboratory performing the assay will advise the healthcare provider as to whether the patient can benefit from treatment with an AP based on whether the patient's ECC or eGFR (or another kidney function parameter) is above or below a predetermined ECC or eGFR (or another kidney function parameter) threshold value or is elevated or reduced relative to one or more controls.

The disclosure also provides a method of measuring the efficacy or pharmacodynamics of an AP in a patient diagnosed with SA-AKI, comprising: (a) conducting a first measurement of the patients' ECC or eGFR (or another kidney function parameter) in a first sample taken from the patient; (b) administering the AP, e.g., RecAP; and (c) conducting a second measurement of ECC or eGFR (or another kidney function parameter) in a second sample taken from the patient, wherein an increase of the ECC or eGFR (or another kidney function parameter) in the second measurement compared to the patient's ECC or eGFR (or another kidney function parameter) in the first measurement, indicates that the patient is responding to treatment with the AP, e.g., RecAP. The disclosure also provides a method of measuring the efficacy or pharmacodynamics of an AP in a patient diagnosed with SA-AKI, comprising: (a) conducting a first measurement of the patients' ECC or eGFR (or another kidney function parameter) in a first sample taken from the patient; and (b) conducting a second measurement of ECC or eGFR (or another kidney function parameter) in a second sample taken from the patient after the patient has been provided with the AP, e.g. RecAP, wherein an increase of the ECC or eGFR (or another kidney function parameter) in the second measurement compared to the patient's ECC or eGFR (or another kidney function parameter) in the first measurement, indicates that the patient is responding to treatment with the AP, e.g., RecAP.

The disclosure also provides a method of measuring the efficacy or pharmacodynamics of an AP in a patient diagnosed with SA-AKI, comprising: (a) conducting a first measurement of the patients' ECC or eGFR (or another kidney function parameter) in a first sample taken from the patient; (b) administering the AP, e.g., RecAP; and (c) conducting a second measurement of ECC or eGFR (or another kidney function parameter) in a second sample taken from the patient, wherein a decrease of the ECC or eGFR (or another kidney function parameter) in the second measurement compared to the patient's ECC or eGFR (or another kidney function parameter) in the first measurement, indicates that the patient is not responding to treatment with the AP, e.g., RecAP. The disclosure also provides a method of measuring the efficacy or pharmacodynamics of an AP in a patient diagnosed with SA-AKI, comprising: (a) conducting a first measurement of the patients' ECC or eGFR (or another kidney function parameter) in a first sample taken from the patient; and (b) conducting a second measurement of ECC or eGFR (or another kidney function parameter) in a second sample taken from the patient after the patient has been provided with the AP, e.g. RecAP, wherein a decrease of the ECC or eGFR (or another kidney function parameter) in the second measurement compared to the patient's ECC or eGFR (or another kidney function parameter) in the first measurement, indicates that the patient is not responding to treatment with the AP, e.g., RecAP.

In some aspects, the second measurement is conducted 1, 2, 3, 4, 5, 6, 7, 8, 9, 10, 11, 12, 13, 14, 15, 16, 17, 18, 19, 20, 21, 22, 23, 24, 25, 26, 27, or 28 days, or at 1, 2, 3, 4, 5, 6, 7, 8, 9, 10, 11, 12, 13, 14, 15 or 16 weeks, or at intervening times, after administering the AP, e.g., RecAP.

In certain aspects, in all the treatment methods disclosed herein, a "loading" dose of an AP is administered to achieve a desired level of kidney function in the patient. If the AP loading dose does not affect the patient's kidney function significantly a decision could be made to discontinue treatment—e.g., to switch to an alternative therapy.

If the loading dose results in increased kidney function in the patient a decision could be made to reduce the AP dose size or frequency to a "maintenance" dose. It is important to note that the methods provided here are guidelines for a healthcare provider to administer treatment, and the ultimate treatment decision will be based on the healthcare provider's sound judgment.

In some aspects, this disclosure includes a method of treating a patient having SA-AKI, or AP for use in a method of treating a patient having SA-AKI, wherein the method comprises: measuring, e.g., in a clinical laboratory, the ECC or eGFR (or another kidney function parameter) level and optionally one or more biomarker levels in a first sample obtained from a patient having SA-AKI, e.g., a sample provided by a healthcare provider, wherein the patient's ECC or eGFR (or another kidney function parameter) level in the first sample is, for example, measured; determining whether the patient's ECC or eGFR (or another kidney function parameter) level in the first sample is below a predetermined ECC or eGFR (or another kidney function parameter) threshold level, or is reduced relative to the ECC or eGFR (or another kidney function parameter) level in one or more controls; and advising a healthcare provider to administer an AP, e.g., RecAP, to the patient if the patient's ECC or eGFR (or another kidney function parameter) level is below a predetermined ECC or eGFR threshold level, or is decreased relative to the ECC or eGFR (or another kidney function parameter) level in one or more controls.

In some aspects, a sample is obtained from the patient (e.g., a 24 hour urine sample or a blood sample) and is submitted, e.g., to a clinical laboratory, for measurement of ECC or eGFR (or another kidney function parameter) alone or in combination with the level of at least another biomarker; or a combination thereof in the sample.

In some aspects, the clinical laboratory performing the assay will advise the healthcare provider as to whether the patient can benefit from treatment with an AP based on whether the patient's ECC or eGFR (or another kidney function parameter) is below or above a predetermined ECC or eGFR (or another kidney function parameter) threshold value.

The formulation, dosage regimen, and route of administration of an AP, e.g., RecAP, can be adjusted to provide an effective amount for an optimum therapeutic response according to the method disclosed herein. With regard to the administration of an AP, the AP may be administered through any suitable means, compositions and routes known in the art. With regard to dosage regiments, a single bolus can be administered, several divided doses can be administered over time or the dose can be proportionally reduced or increased as indicated by the exigencies of the therapeutic situation.

III. Alkaline Phosphatases (AP)

Alkaline phosphatase (AP; EC 3.1.3.1 according to IUBMB Enzyme Nomenclature), is an enzyme that catalyzes the reaction of a phosphatase monoester and H2O to an alcohol and phosphate. Other name(s) for AP are alkaline phosphomonoesterase;

phosphomonoesterase; glycerophosphatase; alkaline phosphohydrolase; alkaline phenyl phosphatase; orthophosphoric-monoester phosphohydrolase (alkaline optimum). The systemic name of AP is phosphate-monoester phosphohydrolase (alkaline optimum).

AP is a wide specificity enzyme, it also catalyzes trans-phosphorylations. In humans and other mammals at least four distinct but related AP are known. They are intestinal, placental, placental-like, and liver/bone/kidney (or tissue non-specific) AP. The first three are located together on chromosome 2 while the tissue non-specific form is located on chromosome 1.

Figure 2:
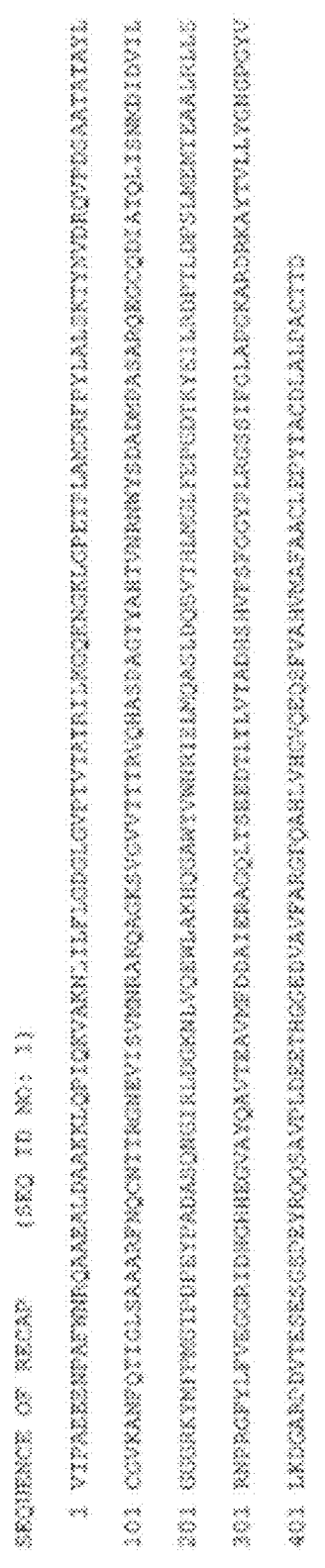

The term "AP of the present disclosure" refers to isolated alkaline phosphatases, including splice variants, isoforms, and polymorphic forms thereof. Also included are recombinant AP and chimeric AP. In a specific aspects, the AP is RecAP. The amino acid sequence of RecAP is shown in FIG. 2. In some aspects, an AP disclosed herein has at least about 70%, at least about 75%, at least about 80%, at least about 85%, at least about 90%, at least about 95%, at least about 96%, at least about 97%, at least about 98%, or at least about 99% sequence identity to the amino acid sequence of SEQ ID NO:1. In some aspects, the AP is a functional fragment (i.e., a fragment of the AP, e.g., AP conserving at least about 10%, at least about 20%, at least about 30%, at least about 40%, at least about 50%, at least about 60%, at least 70%, at least about 80%, or at least about 90% of the AP activity of the corresponding full length AP). In some aspects, the AP is a variant or a derivative of an AP disclosed herein.

An AP for use according to the present disclosure can be a commercial AP enzyme, or any composition comprising the AP enzyme and any means capable of producing a functional AP enzyme in the context of the current invention, such as DNA or RNA nucleic acids encoding an AP protein.

The nucleic acid encoding AP may be embedded in suitable vectors such as plasmids, phagemids, phages, (retro)viruses, transposons, gene therapy vectors and other vectors capable of inducing or conferring production of AP. Also native or recombinant micro-organisms, such as bacteria, fungi, protozoa and yeast may be applied as a source of AP in the context of the current disclosure.

AP containing compositions for use according to the present disclosure can comprise a eukaryotic AP, e.g., a mammalian AP, which may be of the types tissue non-specific AP, such as liver-bone or kidney type, or tissue specific such as placental AP, intestinal AP and placental-like AP. The latter, also known as germ cell AP, is localized to testis, thymus and certain germ cell tumors, and is closely related to both the placental and intestinal forms of AP.

In some aspects, the mammalian AP is a human or a bovine AP. Non-limiting examples of a human AP sequence can be found in the NCBI (Genpept) collection and include: NP_001622 (intestinal AP), NP_001623 (placental AP), NP_112603 (placental-like AP) or NP_000469 (tissue non-specific AP). In some aspects, the AP comprises a polymorphism. In some aspects, the AP is placental AP, placental-like AP, intestinal AP, liver/bone/kidney AP, or a combination thereof. In some aspects, the AP is recombinant AP.

From a conformational point of view, an AP roughly consists of two domains: a crown domain and an active-site domain. The active-site domain can be divided in separate parts like the catalytic residue and the three metal ion sites (Zn1, Zn2 and Mg3). From a primary structure point of view, the crown domain is flanked by the amino acids that form the active site domain. The amino acid sequence of APs and the relative positions of the catalytic and crown domain are known by the skilled person.

In some aspects of the present disclosure, the AP is an isolated or recombinant AP comprising a crown domain and a catalytic domain, wherein said crown domain and said catalytic domain are obtained from different APs and wherein at least one of said different phosphatases is a human phosphatase. In some aspects, the AP is, for example, ECAP (*Escherichia coli* AP) or one of the seven known BIAPs (Bovine Intestinal AP).

In some aspects, AP is an isolated or recombinant AP comprising a crown domain and a catalytic domain, wherein said crown domain and said catalytic domain are obtained from different APs and wherein the different APs are human APs. This is especially useful if the modified phosphatase is subsequently used in human therapy. AP for use in the disclosed methods can be modified, e.g., genetically modified, APs of human origin which are not or only weakly immunogenic.

A modified AP disclosed herein can be used, for example, in "in vitro" or "ex vivo" diagnostics or treatments. Such modified phosphatase can comprise, for example, a human and an *E. coli* AP or may be composed of a bovine and an *E. coli* AP.

In some aspects of the present disclosure, the AP is an isolated or recombinant AP comprising a crown domain and a catalytic domain, wherein said crown domain and said catalytic domain are obtained from different APs and wherein said crown domain is the crown domain of placental AP (ALPP) and wherein said catalytic domain is the catalytic domain of intestinal AP (ALPI). In some aspects, at least one of the different APs is a human phosphatase. In other aspects, both different APs are human phosphatases.

Domain swapped mutants suitable for the methods disclosed herein which are based on the human APs are listed in TABLE 1.

TABLE 1

Domains swapped alkaline phosphatase enzymes. ALPI is intestinal AP, ALPP is placental AP, GCAP is placental-like AP and TNAP is tissue nonspecific AP.

| Catalytic domain | Crown domain | Referred to as |
| --- | --- | --- |
| ALPI | GCAP | catALPI/crownGCAP |
|  | TNAP | catALPI/crownTNAP |
| ALPP | GCAP | catALPP/crownGCAP |
|  | TNAP | catALPP/crownTNAP |
| GCAP | ALPI | catGCAP/crownALPI |
|  | ALPP | catGCAP/crownALPP |
|  | TNAP | catGCAP/crownTNAP |
| TNAP | ALPI | catTNAP/crownALPI |
|  | ALPP | catTNAP/crownALPP |
|  | GCAP | catTNAP/crownGCAP |

In some aspects, the AP is a combinations between the catalytic domain of ECAP or any of the human forms (ALPI, ALPP, GCAP or TNAP) with the crown domain of BIAP. Moreover, combinations of the crown domain of BIAP with the catalytic domain of ECAP or any of the human forms can also be produced.

In some aspects, the modified AP is an AP which under natural conditions are linked to the membrane of a cell via a glycosylphosphatidylinositol (GPI) anchor but which is modified such that it is no longer attached to the membrane of a cell. All isoenzymes are functionally active in the cell membrane and GPI-anchor deficient forms are not naturally present at detectable levels. Although serum AP activity has been demonstrated it is generally accepted that the enzyme is still present in shed membrane fractions or membrane vesicles. AP activity in milk is also present in fractions containing membrane vesicles. The GPI anchor is stored as a precursor molecule in the cell where it is attached to the attachment site through a transamidase. The backbone of the GPI-anchor is identical in mammals, but cell-type dependent modifications are known.

In some aspects, for treatment of human subjects, the AP is human. This is primarily due to the fact that AP forms obtained from other species may be immunogenic in human subjects and treatment could elicit immunological reactions and pathological side effects. In some subjects even lethal side effects, i.e., anaphylactic shock may occur and the risks of immunological side effects are therefore preferably minimized by use of human AP forms.

As isolation of AP from humans is not practical, human recombinant forms of AP proteins can be routinely produced in different recombinant expression platforms. However, expression and purification of GPI modified and membrane-anchored proteins is notoriously difficult; GPI proteins are difficult to separate from membranes and difficult to isolate and purify. Thus, in some aspects, the recombinant APs comprises a modification in the GPI signal sequence, wherein said modification results in a secreted AP, i.e., the AP is not attached to the cell membrane.

There is no general sequence responsible for the attachment of a GPI anchor, but there some specific consensus characteristics:

(i) hydrophobic stretch of amino acids at the C-terminus (at least 11 amino acids, but preferably more than 11 amino acids);

(ii) upstream of the hydrophobic region, a spacer of hydrophilic amino acids (5-12 amino acids);

(iii) GPI is attached to a small amino acid: glycine, aspartic acid, asparagine, alanine, serine or cysteine; and, (iv) the 2 subsequent amino acids downstream of the GPI attachment site must be small amino acids and in the majority of cases they are selected from glycine, aspartic acid, asparagine, alanine, serine or cysteine.

In some aspects, the recombinant AP comprises a modification in the GPI signal sequence, wherein said modification results in a secreted AP that is biological active, i.e., it shows activity towards a biologically relevant substrate. In some aspects, the secreted AP is a human AP. In some aspects, the secreted human AP human liver-kidney-bone phosphatase, human intestinal AP, or human placental-like alkaline phosphatase.

Based on the consensus characteristics above, a skilled person can introduce modifications, e.g., by inserting one or multiple amino acids, that would disrupt part of the consensus a result in an AP not capable of attaching a GPI anchor. Thus, in some aspects, the recombinant AP comprises a modification in the GPI signal sequence which results in a secreted AP, wherein the modification comprises a mutation or a deletion of at least one amino acid in the sequence encompassing the consensus GPI signal sequence.

In some aspects, the AP is an AP disclosed in U.S. Pat. No. 8,557,545. In some aspects, the AP is a chimeric AP or chimeric AP-like protein such as those described in in U.S. Patent Appl. Publ. No. US2017/0009216 and US2014/0193388. In some specific aspects of the present disclosure, the AP is a recombinant alkaline phosphatase comprising the catalytic domain of ALPI (intestinal alkaline phosphatase) and the crown domain of ALPP (placental alkaline phosphatase), e.g., RecAP (SEQ ID NO: 1). RecAP is also known as catALPI/crownALPP, Xinplap, and sALPI-ALPP-CD. In some aspects, the AP is an improved RecAP, e.g., LVL-RecAP (corresponding to SEQ ID NO:1 in U.S. Patent Appl. Publ. No. US2017/0009216).

In some aspects, an AP of the present disclosure comprises (i) a sequence having at least about 70%, at least about 75%, at least about 80%, at least about 85%, at least about 90%, at least about 95%, at least about 96%, at least about 97%, at least about 98%, or at least 99% sequence identity with the crown domain of a human ALPP, and (ii) a sequence having at least about 70%, at least about 75%, at least about 80%, at least about 85%, at least about 90%, at least about 95%, at least about 96%, at least about 97%, at least about 98%, or at least 99% sequence identity with the catalytic domain of a human ALPI.

In some aspects, said sequence having said sequence identity to the crown domain of ALPP is situated in a protein according to the invention at approximately the same position as the crown domain of ALPP in the native ALPP protein The percentage of identity of an amino acid or nucleic acid sequence, or the term "% sequence identity", is defined herein as the percentage of residues in a candidate amino acid or nucleic acid sequence that is identical with the residues in a reference sequence after aligning the two sequences and introducing gaps, if necessary, to achieve the maximum percent identity. In a preferred embodiment, the calculation of said at least percentage of sequence identity is carried out without introducing gaps. Methods and computer programs for the alignment are well known in the art, for example "Align 2" or the BLAST service of the National Center for Biotechnology Information (NCBI).

V. Amelioration of Adverse Effects from Treatments and Diagnostics

In addition to, e.g., treatment or amelioration of the symptoms of SA-AKI, the methods disclosed herein can be applied to treat and/or prevent loss of renal function caused by the treatment of other diseases or conditions, diagnostic methods, etc., wherein loss of renal function is an adverse effect. In some aspects, the methods disclosed herein can be applied to SA-AKI patients that have to undergo renal replacement, subjected to the use of contrast media for diagnostic purposes, etc.

Renal Replacement Therapy: Reduced renal function can be an indication for RRT, but in some cases reduced renal function may also be a contra-indication for RRT. This is explained by the fact that RRT generally is accompanied by intravasal fluid depletion and critically ill patients do not tolerate fluctuations in amount of intravasal fluid. This may ultimately lead to hypovolemic shock, which compromises the blood flow to the kidneys, exposing the kidneys to an ischemic insult. Complete loss of residual renal function has been observed in subjects receiving chronic RRT. The present invention now provides a method to decrease and/or prevent loss of renal function, e.g., complete loss of residual renal function, in a subject receiving chronic RRT comprising administering an AP, preferably an AP as disclosed herein, e.g., RecAP, before and/or during RRT. The present invention also provides AP for use in a method to decrease and/or prevent loss of renal function, e.g., complete loss of residual renal function, in a subject receiving chronic RRT, wherein an AP, preferably an AP as disclosed herein, e.g., RecAP, is administered before and/or during RRT.

Contrast media: Another treatment with a risk of reducing renal function is the use of intravascular contrast media, such as for instance iodinated contrast media. Especially the ionic contrast media, which are highly hyperosmolar in comparison with (blood)plasma are often associated with a reduction in renal function. The effect of ionic contrast media may be explained as follows. The hyperosmolar contrast agent may attract extravasal fluids into the vascular system, which can cause the arteries of the kidneys to expand. When the arteries expand vasoconstrictors are released to compensate for the artery expansion. These actions can result in a rapid opening and closing action of the arteries. The result of this action is a diminished blood supply to kidneys which can lead to total shut down of the kidneys. Arteries can also be constricted to an extent that they totally close. The body attempts to regulate the fluid overload in the vascular system. However, if the kidneys are non-functional, either as a result of the contrast media or independent thereof, the fluid is forced to seek other avenues of escape causing fluid overload to occur in other body systems. One of the major results of this event is pulmonary edema. Accordingly, the present disclosure provides methods to retain or improve renal function when ionic contrast media are used comprising administering an AP, preferably an AP as disclosed herein, e.g., RecAP. In such case, a patient requiring contrast media can receive such necessary treatment with reduced risk of reducing renal function. In cases were contrast media was contra-indicated in patients with (severe) reduced renal function, due to alternative treatment that could preserve or improve renal function, it is now possible to treat such patients with an AP, preferably an AP as disclosed herein, e.g., RecAP, in order to enable them to receive such contrast media. In some aspects, an AP, preferably an AP as disclosed herein, e.g., RecAP, can be administered before and/or during and/or after administration of contrast media. As used herein, the term "contrast media" encompasses not only a single contrast medium (contrast agent) but also combinations of two or more contrast media.

Cardiac surgery and kidney transplantation: Cardiac surgery can also reduce renal function. Cardiac surgery itself is a risk factor for AKI, but peri-operative parameters can influenced independently the risk on AKI after cardiac surgery. These parameters are, e.g., preoperative anemia, red blood cell transfusion, and surgical re-exploration. These parameters, and heart surgery as such, are all believed to cause ischemia to the kidney. Not only heart surgery, but also, e.g., kidney surgery or transplantation can cause ischemia to renal tissue. Thus kidney transplantation is also regarded as a treatment with a risk of reducing renal function. As cardiac surgery is a treatment carrying a risk of reducing renal function, administration of an AP, preferably an AP as disclosed herein, e.g., RecAP, can improve or retain renal function in a patient receiving cardiac surgery.

Medication: Other treatments having a risk of reducing renal function include for instance the use of certain medication or drugs. Renal dysfunction and injury secondary to medications are common, and can present as subtle injury and/or overt renal failure. Some drugs perturb renal perfusion and induce loss of filtration capacity. Others directly injure vascular, tubular, glomerular and interstitial cells, such that specific loss of renal function leads to clinical findings, including microangiopathy, Fanconi syndrome, acute tubular necrosis, acute interstitial nephritis, nephrotic syndrome, obstruction, nephrogenic diabetes insipidus, electrolyte abnormalities and chronic renal failure. Specifically, the use of certain anti-microbial agents (such as Amphotericin B, caspofungin, vancomycin, levofloxacin, and aminoglycosides such as tobramycin and gentamicin), other drugs (e.g., chemotherapeutic agents such as cisplatin, carboplatin, or methotrexate; protease inhibitors such as indinavir or ritonavir; gold; lithium; anti-inflammatory drugs such as non-steroidal anti-inflammatory drugs; cyclosporin; tacrolimus; sirolimus; anti-hypertensive drugs such as angiotensin converting enzyme (ACE) inhibitors and angiotensin receptor blockers (ARBs)); and certain chemicals such as silicates, hydrocarbons, heavy metals (such as Cd, Hg, Pb), insecticides, herbicides, ethylene glycol, and bacterial toxins (such as tetanus, streptococcal toxins) are known to bear the risk of reducing renal function in subjects who have taken or have been exposed to said agents or chemicals. Accordingly, the present disclosure provides a method, or AP for use in a method, to reduce the effect of these agents or chemicals by administering an AP, preferably an AP as disclosed herein, e.g., RecAP, to subjects exposed to such agents or chemicals. It also possible to reduce the amount of certain drugs, as the present invention provides the insight that a use of AP according to the invention reduces the amount of comedication in a patient.

In some aspects, the present disclosure provides methods, or AP for use in a method, to treat a subject at risk of reduced renal function due to RRT, exposure to intravascular contrast media, kidney and/or heart surgery, kidney and/or heart transplantation, blood transfusion, red blood cell transfusion, drug treatment, and surgical (re)exploration wherein the method comprises administering an AP, preferably an AP as disclosed herein, e.g., RecAP, to the subject. The treatment with an AP, preferably an AP as disclosed herein, e.g., RecAP, can take place before and/or during and/or after RRT, exposure to intravascular contrast media, kidney and/or heart surgery, kidney and/or heart transplantation, blood transfusion, red blood cell transfusion, drug treatment, or surgical (re)exploration.

A treatment having a risk of reducing renal function may result in reducing the blood flow through the kidneys. The outer medulla of the kidney is especially susceptible to injury and/or cell damage when the blood supply is decreased, leading to an ischemic event. Thus, it is especially useful to use an AP, preferably an AP as disclosed herein, e.g., RecAP, for retaining or improving renal function when the mean arterial blood pressure is, or is expected to become, less than 80 mm Hg. Below a mean arterial blood pressure of 80 mm Hg, the kidney is at risk of being injured, which generally results in a reduction of renal function.

Thus, in some aspects of the present disclosure, an AP, preferably an AP as disclosed herein, e.g., RecAP is provided in a treatment with a risk of reduce renal function, wherein the treatment results in or is accompanied by, hypoperfusion of the kidney, e.g., due to mean arterial blood pressure being below 80 mm Hg, or below 75 mm Hg, or below 70 mm Hg, or below 65 mm Hg, or below 60 mm Hg. In some aspects, the administration of an AP, preferably an AP as disclosed herein, e.g., RecAP is able to, at least in part, prevent a reduction in renal function by preventing kidney injury due to the drop in mean arterial blood pressure.

VI. Reduction of Co-Medication

As discussed above, administration of an AP, preferably an AP as disclosed herein, e.g., RecAP to patients with SA-AK results in an increase in kidney function and/or survival. Accordingly, the present disclosure provides a method of reducing the amount of medication administered to a patient with sepsis, or AP for use in a method of reducing the amount of medication administered to a patient with sepsis, the method comprising administering an AP, preferably an AP as disclosed herein, e.g., RecAP to the patient.

In some aspects, administering an AP, preferably an AP as disclosed herein, e.g., RecAP can be used to reduce the amounts of medication or comedication used in the treatment of diseases and conditions other than SA-AKI that may adversely affect kidney function in the subject.

In some aspects, the medication is for the treatment of a heart condition, such as a heart condition resulting from myocardial infarction or heart failure. Thus, is some aspects, the present disclosure provides a method for reducing the amount of medication for the treatment of a heart condition, or AP for use in a method for reducing the amount of medication for the treatment of a heart condition, thereby reducing for instance the adverse side effects of such medication, the method comprising administering AP, e.g., RecAP, to a patient.

In some aspects, the administration of AP, preferably RecAP or any of the AP disclosed above, to a subject in need thereof can reduce the amount of (co)medication, thereby at least in part preserving and/or increasing renal function. In some aspects, the present disclosure provides a method according to the disclosure for reducing the amount of (co)medication in a patient already suffering (or at risk of suffering) from reduced renal function. In a further embodiment, the invention provides an alkaline phosphatase for use in a method according to the invention, comprising administering an AP as disclosed herein, e.g., RecAP.

In some aspects, the (co)medication is for the treatment of a heart condition, e.g., a heart condition resulting from myocardial infarction or heart failure. In another aspect, the (co)medication is a diuretic medicament. Diuretic medicaments influence the fluid balance in an individual by forced diuresis. Diuretics have been proven useful for, amongst others, the treatment of heart failure, hypertension and renal diseases. On the other hand, in a person already suffering from reduced renal function, diuretics may reduce renal function even further, as a result of the reduction in blood pressure due to diuresis. AP, however, is able to reduce such reduction in blood pressure and/or prevent or improve reduced renal function resulting from such reduction in blood pressure.

In another aspect, the present disclosure provides a method for reducing (co) medication, or AP for use in a method for reducing (co) medication, the method comprising administering an AP, preferably an AP as disclosed herein, e.g., RecAP, wherein the (co)medication is a class III anti-arrhythmic, a selective β-blocker, a digitalis glycoside, a vitamin K antagonist, or a selective β-2-adrenoceptor agonist.

In yet another aspect, the present disclosure provides a method for reducing (co) medication, or AP for use in a method for reducing (co) medication, the method comprising administering an AP, preferably an AP as disclosed herein, e.g., RecAP, wherein the (co) medication is potassium, a benzo-derivative, a plain sulfonamide, magnesium and/or digitalis glycosides. As the above mentioned drugs are potentially harmful for the kidney, the use of AP for reducing the amount of these drugs, consequently reduces the risk of reducing renal function in patients receiving AP.

Without being bound to theory, it is believed that the reduction in (co)medication observed in individuals that have received AP is a direct or indirect beneficial effect of AP on the risk of atrial fibrillation or other cardiovascular or vascular disorders. Thus, in some aspects, the present disclosure provides a method for preventing and/or treating atrial fibrillation, or AP for use in a method for preventing and/or treating atrial fibrillation, the method comprising administering an AP, preferably an AP as disclosed herein, e.g., RecAP. The atrial fibrillation can be due, e.g., to reduced renal function and/or (co)medication.

As discussed before, AP is especially useful in reducing the amount and/or adverse side effects of (co)medication. Therefore, also provided is a method for decreasing the amount of (co)medication, or AP for use in a method for decreasing the amount of (co)medication, the method comprising administering an AP, preferably an AP as disclosed herein, e.g., RecAP to a subject receiving (co)medication or being at risk of receiving the (co)medication. In some aspects, administering an AP, preferably an AP as disclosed herein, e.g., RecAP, not only decreases the amount of (co)medication in subjects receiving AP in comparison with subjects receiving placebo, but also reduces adverse effects of (co)medication. Accordingly, the present disclosure provides a method for decreasing adverse effects of (co)medication in a subject receiving said (co)medication or being at risk of receiving said (co)medication, or AP for use in a method for decreasing adverse effects of (co)medication in a subject receiving said (co)medication or being at risk of receiving said (co)medication, the method comprising administering an AP, preferably an AP as disclosed herein, e.g., RecAP, before, during and/or after the subject receives the medication, thereby decreasing adverse effects of the (co)medication in the subject.

In some aspects, the present disclosure provides a method for reducing (co)medication for the treatment of a heart condition, e.g., a heart condition resulting from myocardial infarction or heart failure, or AP for use in a method for reducing (co)medication for the treatment of a heart condition, e.g., a heart condition resulting from myocardial infarction or heart failure, the method comprising administering an AP, preferably an AP as disclosed herein, e.g., RecAP.

In some aspects, the (co)medication is a class III antiarrhythmic, a selective β-blocker, a digitalis glycoside, a vitamin K antagonist, or a selective β-2-adrenoceptor agonist.

In other aspects, the (co)medication is potassium, a benzo-derivative, a plain sulfonamide, magnesium and/or digitalis glycosides. As the before mentioned drugs are potentially kidney damaging in subjects exposed to them, reducing the amount of these drugs results in a reduced risk of reduced renal function in these subjects.

In one aspect, the present disclosure provides a method for preventing and/or treating atrial fibrillation, or AP for use in a method for preventing and/or treating atrial fibrillation, wherein the method comprises administering an AP, preferably an AP as disclosed herein, e.g., RecAP, to a subject suffering or at risk of suffering from atrial fibrillation, thereby preventing or treating said atrial fibrillation.

While the current application may describe features as part of the same embodiment or as parts of separate embodiments, the scope of the present invention also includes embodiments comprising any combination of all or some of the features described herein.

Preferred Aspects

Aspect 1. Alkaline phosphatase (AP) for use in a method to treat sepsis-associated acute kidney disease injury (SA-AKI) in a subject in need thereof, the method comprising administering an effective amount of alkaline phosphatase (AP) to said subject, wherein (i) the subject has an ECC (endogenous creatinine clearance) rate ≤60 ml/min prior to the treatment with AP or an eGFR (estimated glomerular filtration rate) ≤60 ml/min prior to the treatment with AP,
  (ii) the AP is administered in at least one 500 U/kg to 2,000 U/kg dose, and
  (iii) the administration of the AP results in an increase in renal function.

Aspect 2. AP for use according to Aspect 1, wherein the subject has moderate kidney injury (15-60 ml/min ECC) or 15-60 ml/min eGFR prior to the treatment with AP.

Aspect 3. AP for use according to Aspect 1 or Aspect 2, wherein the subject has severe kidney injury (<15 ml/min ECC) or <15 ml/min eGFR prior to the treatment with AP.

Aspect 4. AP for use according to any one of Aspects 1-3, wherein the subject does not have mild kidney injury (>60 ml/min ECC) or >60 ml/min eGFR prior to the treatment with AP.

Aspect 5. AP for use according to any one of Aspects 1-4, wherein the AP is a human AP.

Aspect 6. AP for use according to any one of Aspects 1-5, wherein the AP is a recombinant AP Aspect 7. AP for use according to any one of Aspects 1-6, wherein the recombinant AP is chimeric.

Aspect 8. AP for use according to any one of Aspects 1-7, wherein the chimeric AP has at least 80%, at least 85%, at least 90%, at least 95%, at least 96%, at least 97%, at least 98%, at least 99%, or 100% sequence identity to the amino acid sequence of RecAP (SEQ ID NO: 1).

Aspect 9. AP for use according to any one of Aspects 1-8, wherein the increase in renal function comprises an increase in ECC with respect to ECC in the absence of treatment or an increase in eGFR with respect to eGFR in the absence of treatment.

Aspect 10. AP for use according to any one of Aspects 1-9, wherein sepsis is detected less than 96 hours prior to AP administration.

Aspect 11. AP for use according to any one of Aspects 1-10, wherein sepsis is detected less than 72 hours prior to SA-AKI detection.

Aspect 12. AP for use according to any one of Aspects 1-11, wherein treatment is initiated within 24 hours after sepsis is detected.

Aspect 13. AP for use according to any one of Aspects 1-12, wherein treatment is initiated within 24 hours after SA-AKI is detected.

Aspect 14. AP for use according to any one of Aspects 1-13, wherein AP is administered once daily.

Aspect 15. AP for use according to any one of Aspects 1-14, wherein AP is administered intravenously.

Aspect 16. AP for use according to any one of Aspects 1-15, wherein AP is administered in three daily doses.

Aspect 17. AP for use according to any one of Aspects 1-16, wherein the AP dose is 0.8 mg/kg or 1.6 mg/kg of RecAP.

Aspect 18. AP for use according to any one of Aspects 1-17, wherein the AP dose is 500 U/kg or 1000 U/kg of RecAP.

Aspect 19. AP for use according to any one of Aspects 1-18, wherein the administration of at least one dose of AP results in a shortening of duration or cessation of renal replacement therapy (RRT) in a subject undergoing RRT.

Aspect 20. AP for use according to any one of Aspects 1-19, wherein the administration of at least one dose of AP results in the preservation or increase of glomerular filtration rate (GFR) or eGFR in the subject.

EXAMPLES

Example 1

Human Recombinant Alkaline Phosphatase for Sepsis-Associated Acute Kidney Injury Sepsis-associated acute kidney injury (AKI) adversely affects long-term renal outcomes and survival. Administration of the detoxifying enzyme alkaline phosphatase improved renal function and survival in preclinical studies. We investigated the efficacy and safety of a human recombinant alkaline phosphatase (RecAP) (FIG. 2) in patients with sepsis-associated AKI.

In Part 1 of the adaptive phase 2a/2b STOP-AKI trial, patients were randomized to receive RecAP 0.4, 0.8, or 1.6 mg/kg, or placebo, once daily for 3 days to establish the optimal dose.

In Part 2, this dose was compared with placebo. The primary endpoint was time-corrected area under the curve of the endogenous creatinine clearance for days 1-7 ($AUC_{1-7}$ ECC), with renal replacement therapy (RRT) as a key secondary endpoint. Longer-term renal function, major adverse kidney events (MAKE) on days 28, 60, and 90, and survival were also analyzed. Overall, 301 patients were enrolled. Compared with placebo (n=116), RecAP (1.6 mg/kg, n=111) did not significantly affect $AUC_{1-7}$ ECC or RRT rates. However, ECC improvement on days 21 (P=0.02) and 28 (P=0.01) was more pronounced and composite MAKE at days 60 (P=0.045) and 90 (P=0.03) had a lower incidence in patients receiving RecAP. All-cause 28-day mortality was 14.4% in RecAP-treated patients versus 26.7% in placebo-treated patients (P=0.02). No differences in (serious) adverse events were observed between groups.

RecAP treatment resulted in enhanced and sustained recovery of renal function and better survival versus placebo. RecAP appeared safe and well tolerated.

Methods

I. STOP-AKI Trial Design and Participants

The STOP-AKI trial, was an international randomized, double-blind, placebo-controlled, four arm, parallel-group, dose-finding adaptive phase 2a/2b trial conducted in critically ill adults with SA-AKI. The protocol, including slight changes in eligibility criteria implemented after inclusion of 120 patients, was published previously (Peters et al. BMJ Open 2016; 6:e012371).

ICU patients aged >18 years with a diagnosis of sepsis (Levy et al. Crit Care Med 2003; 31:1250-6) and a first diagnosis of AKI (Mehta et al. Crit Care 2007; 11:R31) were eligible for study participation. The inclusion and exclusion criteria are provided below Inclusion Criteria To be included the study, the subject
(i) has informed consent form signed by patient or legal representatives or independent investigator, according to local rules and regulations,
(ii) is aged 18-85 years, inclusive,
(iii) is admitted to the intensive care unit or intermediate care unit,
(iv) has diagnosis of sepsis (<96 hours prior to first study drug administration or <72-hour prior to acute kidney injury (AKI) diagnosis), according to criteria defined by the American College of Chest Physicians/Society of Critical Care Medicine (Bone et al. Chest 1992; 101:1644-55.), based on
  A. a proven or strongly suspected bacterial infection
  B. at least two of the following four SIRS criteria within a timeframe of 72 hours at the time of AKI diagnosis (Note: it is not required that symptoms are present simultaneously at study randomisation)
    1. Core temperature >38° C. or <36° C.
    2. Heart rate >90 bpm (unless the patient has a medical condition known to increase heart rate or is receiving treatment to prevent tachycardia)
    3. Respiratory rate >20 breaths/min, $PaCO_2$<32 mm Hg or the use of mechanical ventilation for an acute respiratory process
    4. White cell count >12,000/mm$^3$ or <4000/mm$^3$ or a differential count showing >10% immature neutrophils
(v) has first diagnosis of AKI, defined as AKI Stage 1 or greater, according to the following AKIN criteria (Note: adjusted in regard to time-window):
  A. Urinary output <0.5 ml/kg/h for >6 hours following adequate fluid resuscitation when applicable, in the absence of underlying primary renal disease, or
  B. Increase (absolute) in serum creatinine >26.2 µmol/l (0.30 mg/dl) compared with a serum creatinine value within the previous 48 hours, or presumed to have occurred in the previous 48 hours when compared with a reference creatinine value (see below), or
  C. Increase (relative) in serum creatinine to >150% (>1.5-fold) compared with a serum creatinine value in the previous 48 hours or presumed to have occurred in the previous 48 hours, when compared with a reference creatinine value (in the absence of primary underlying renal disease).
  The reference creatinine value is a serum creatinine value in the following order of preference:
    1. Lowest value within 3 months of the hospital admission. If not available:
    2. At hospital admission. If not available:
    3. At ICU admission. If not available:
    4. Lowest value between 3 and 12 months prior to hospital admission
(vi) when the diagnosis of AKI is made according to one of the AKIN serum creatinine criteria, continuing AKI needs to be confirmed by a confirmative fluid-corrected serum creatinine measure, defined as no decrease in serum creatinine ≥26.2 µmol/l (≥0.30 mg/dl). The result must be available prior to randomisation. Administration of study treatment must be started within 24 hours after first AKI diagnosis
(vii) when the AKI diagnosis was made according to the AKIN urine output criteria, the oliguria or anuria should still meet the AKIN urine output criteria prior to randomisation. Administration of study treatment must be started within 24 hours after first AKI diagnosis Exclusion Criteria Subjects were excluded from the study if at least one of the following conditions was fulfilled:
(i) Woman of childbearing potential with a positive pregnancy test (blood or urine), pregnant or breast feeding
(ii) Weighs more than 115 kg (253 lb)
(iii) Has life-support limitations (eg, do not intubate, do not dialyse, do not resuscitate)
(iv) Is known to be HIV-positive
(v) Has urosepsis. As urogenital obstruction, frequently observed during urosepsis, may also account for an increase in serum creatinine levels, it is not possible to define which proportion might be due to SA-AKI. Therefore, urosepsis patients are excluded.
(vi) Is already on renal replacement therapy (RRT) or a decision has been made to initiate RRT within 24 hours after planned start of study drug administration
(vii) Is receiving immunosuppressant treatment or is on chronic high doses (high-dose therapy exceeding 2 weeks of treatment) of steroids equivalent to prednisone/prednisolone 0.5 mg/kg/day, including solid organ transplant patients. Patients with septic shock treated with hydrocortisone (eg, 3×100 mg) can be included (viii) Is expected to have rapidly fatal outcome (within 24 hours)
(ix) Has known, confirmed fungal sepsis
(x) Has advanced chronic liver disease, confirmed by a Child-Pugh score of 10-15 (Class C)
(xi) Has acute pancreatitis with no established source of infection
(xii) Has participated in another investigational study within 30 days prior to enrolment into the study
(xiii) Is not expected to survive for 28 days due to medical conditions other than SA-AKI, including cancer (previous haematological malignancies that are not actively treated allowable), end-stage cardiac disease, cardiac arrest requiring cardiopulmonary resuscitation or with pulseless electrical activity or asystole within the past 30 days, end-stage lung disease and end-stage liver disease
(xiv) Has known prior history of CKD with a documented eGFR <60 ml/min by a commonly used formula such as MDRD or CKD-EPI, known GFR <60 ml/min or a known history of persistent creatinine level ≥150 µmol/l (1.70 mg/dl) prior to entry for reasons other than the current sepsis condition. CKD is a disease with a distinct pathophysiology compared with AKI. Also, if eGFR is impaired, the chances of an intervention to prevent further deterioration are limited. To increase homogeneity of the study population, these patients are therefore excluded.
AKI, acute kidney injury; AKIN, acute kidney injury network; CDK, chronic kidney disease; CKD-EPI, Chronic Kidney Disease Epidemiology Collaboration; eGFR, estimated glomerular filtration rate; ICU, intensive care unit; IV, intravenous; MDRD, Modification of Diet in Renal Disease; NSAIDs, non-steroidal anti-inflammatory drugs; RRT, renal replacement therapy; SIRS, systemic inflammatory response syndrome.
(xv) Has diagnosis of malaria or other parasite infections
(xvi) Has burns on >20% of body surface
(xvii) Has had AKI diagnosis according to the AKI inclusion criteria for a period longer than 24 hours prior to study drug administration
(xviii) Is anticipated to be treated with non-continuous RRT from day 1 to day 7
(xix) During day 1 to day 7, continuous RRT is anticipated to be started or stopped not according to per protocol criteria
(xx) The AKI is most likely attributable to other causes than sepsis, such as nephrotoxic drugs (NSAIDs, contrast, aminoglycosides) and renal perfusion-related (acute abdominal aortic aneurysm, dissection, renal artery stenosis)
(xxi) Improvement in serum creatinine of at least 26.2 µmol/l (0.30 mg/dl) prior to administration of the study drug
(xxii) Patients who use nephrotoxic medication and who fulfil the SA-AKI inclusion criteria at screening are not eligible if the use of this nephrotoxic medication is planned to continue (eg, NSAIDs, ACE inhibitors, gentamycin, tobramycin) when alternative, medically appropriate non-nephrotoxic medication is available.
(xxiii) Has a history of known intravenous drug abuse
(xxiv) Is an employee or family member of the investigator or study site personnel
(xxv) Has active heamatological malignancy Treatment was initiated within 24 hours after SA-AKI was first diagnosed and within 96 hours following fulfilment of sepsis criteria (Levy et al. Crit Care Med 2003; 31:1250-6.). Patients enrolled during the first part of the study were randomly assigned to receive either placebo or one of three RecAP doses (0.4; 0.8; 1.6 mg/kg) once daily for 3 days using an 1:1:1:1 allocation ratio.

After the 120th patient, futility or superiority of the intervention on the primary endpoint data and the fit to an assumed maximum effect attributable to the drug ($E_{max}$) model dose-response curve was assessed. An interim analysis proceeded as follows.

Interim analysis: An unblinded interim analysis was conducted on the Part 1 data to determine the optimal RecAP dose for Part 2. This analysis compared the primary efficacy endpoint and a selection of the safety data for the four treatment groups from Part 1. The interim analysis was conducted when the first 7 days of laboratory data had been collected for 120 patients from Part 1, unless the patient was randomized but had died or discontinued before completing 7 days.

To maintain the blind, the interim analysis was conducted and delivered by an unblinded PPD biostatistics team located at a different site to the blinded PPD biostatistics personnel involved in the study. A futility analysis was conducted at the interim analysis.

Futility analysis: At the interim analysis, the data were reviewed to identify whether none of the RecAP doses show evidence of efficacy. The results were assessed from the comparison of each RecAP dose with placebo on the primary endpoint, using a one-sided significance level of 0.8. This significance level was chosen for the futility analysis to ensure a sufficient overall power for the study and to allow for the multiple comparison to placebo. At the futility analysis, each RecAP dose would only be deemed as having shown some evidence of efficacy if the one-sided, unadjusted p-value for its comparison with placebo is less than 0.8.

Selection of optimal RecAP dose: The optimal dose was defined as the dose with the best safe improvement on creatinine clearance compared to placebo.

Unless the DSMB had safety concerns pertaining to specify dose level(s) of RecAP and/or the Emax model (dose-response modelling of the primary endpoint) highlights unusual trend(s), the optimal dose would be, preferably, the highest dose of RecAP (i.e. 1.6 mg/kg).

If there were safety concerns and/or some concerns with regard to the dose-response curve, the selection of the optimal dose would be carried out using the following effectiveness criteria. The optimal dose level would be selected amongst the dose levels where there are no safety or/and dose-response modelling concerns.

The effectiveness of a dose level would be determined based on the one-sided unadjusted p-value for comparison with placebo on the primary endpoint, i.e. the dose with the smallest p-value would be considered the most effective dose. Any dose with a one-sided unadjusted p-value less than 0.025 would be considered to have a significantly greater improvement on creatinine clearance than placebo. However, the comparison with placebo did not have to be significant at the 2.5% level for a dose to be considered the most effective dose. Should more than one dose have appeared to be the most effective with the same effect, the safety data as well as the Emax dose-response modelling should be closely examined for selecting the optimal dose.

The adaptive design directed the cessation of two treatment arms, as described in the statistical analysis plan such that, in Part 2, patients were randomly assigned to receive either placebo or the optimal dose of RecAP selected based on interim analysis of the primary endpoint data.

II. Randomization and Study Medication

The randomization schedule was stratified by site. Study drug dose rationale (Peters et al. BMJ Open 2016; 6:e012371) is explained below.

Dose Rationale and Pharmacokinetics

Selection of Doses in the Study and Timing of Doses for Each Patient: No dose-limiting toxicity was observed in pre-clinical and clinical studies with RecAP up to daily doses of 18 mg/kg (10 000 U/kg) and 36 mg/kg (20 000 U/kg) maintained for 14 days in Gottingen mini-pigs, and in healthy volunteers for a single dose up to 3.2 mg/kg (2000 U/kg) and for multiple doses up to 3 daily doses of 1.6 mg/kg (1000 U/kg). Therefore, the dose rationale was primarily based on: 1) observed Phase 1 RecAP PK parameters; 2) trough levels (293 U/l, corresponding to 0.171 mg/l RecAP) obtained in a previous study using Bovine Intestinal Alkaline Phosphatase (BiAP); and 3) exposure maintained during the previous study using BiAP and associated with clinical activity. The three dose-level schedules for the first part of this Phase 2 study, in addition to the placebo group, are shown in FIG. 1.

Using PK simulation experiments, these schedules provided the area under the concentration-time curve from zero up to an infinite time ($AUC_{0\text{-}inf}$) and observed minimum post-administration plasma or serum concentration ($C_{min}$) levels that were similar to or exceeded the presumed minimal requirements based on two different BiAP studies. Furthermore, these dose groups were likely to achieve significantly different exposures when comparing three groups of 30 patients (as informed by the observed PK variability in Phase 1 patients). Analyzing PK simulations, the RecAP low-dose group was expected to achieve sufficient exposure, with $C_{min}$ dropping below target trough concentration before re-infusion, whereas the mid-dose and high-dose groups exceeded target exposure and $C_{min}$. If clinical activity was observed to be different in the Phase 2 study of STOP-AKI at interim analysis, the proposed design of dose groups was likely to enable a clear decision on optimal RecAP dose for continuation into the second part of the study.

Pharmacokinetics: The PK model developed in phase I is still applicable, indicating similar pharmacokinetic properties. See FIG. 6. The PK model allows for a co-variate analysis. Covariates studied include: age, weight, BMI, race, AKIN stage, RRT, baseline ClCr, KIM, CRP, IL6, IL18, LBP, FeNa, BUN, albumin, ALAT, ASAT, and bilirubin. Except for ALAT and ASAT at baseline, none of these parameters appears to have an influence on the PK of RecAP.

The lowest dose was selected in order to reach trough plasma concentrations below the estimated effective concentration. The middle and highest doses were selected to have trough concentrations at or in excess of the estimated effective concentration, respectively. Study drug was administered as a 1-hour intravenous infusion within 24 hours after SA-AKI was first diagnosed, and then 24±1 and 48±1 hours later. Administration of nephrotoxic drugs were avoided where possible, as recommended (Okusa et al. Kidney Int 2014; 85:39-48). Personnel involved in this study were blinded to treatment assignment during Parts 1 and 2; therefore, to maintain blinding, AP levels were not measured until day 14 (details on blinding are shown below).

Blinding: RecAP was supplied as a clear, colorless, pyrogen-free solution for intravenous infusion with a content of 40 mg per vial at 8.0 mg/ml in an aqueous buffer. Matching placebo was supplied in an identical manner. All ampoules and drug boxes had a fully identical appearance and label. All persons involved in the study were blinded to treatment assignment. The randomization schedule was held by an independent team at a different regional location and was not revealed to the blinded study team until all patients had completed the study and the database had been finalized for the end of the study. The determination of AP activity, often part of the routine clinical chemistry panel, could lead to unblinding and to erroneous interpretation of liver function, as the RecAP administered would increase the AP activity, exceeding many times the reference range AP levels. For that reason, AP activity levels from samples taken during the first 14 days of the study were not allowed to be reported to the study team members or to any other study staff member involved in the conduct of the study. After day 14, considering the terminal half-life of RecAP, AP activity levels were expected to have returned to normal levels. Therefore, results of AP activity in samples that were taken after day 14 were reported.

IV. Outcome Measures

Figure 3:
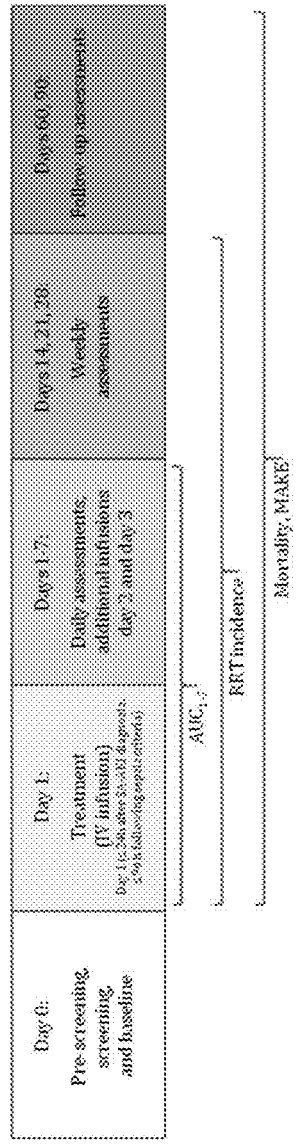
FIG. 3 shows a timeline of the STOP-AKI study, including dosage regimen and timeframes to determine $AUC_{1-7}$, RRT incidence, and mortality and MAKE.

The primary objective of this study was to investigate the optimal therapeutic dose of RecAP and to evaluate its effect on renal function (ECC), defined as the area under the time-corrected (i.e. measured per day) curve (AUC) for ECC from day 1 through 7, divided by 7 to provide a mean creatinine clearance ($AUC_{1\text{-}7}$ ECC). Requirement for renal replacement therapy (RRT) was the main related clinical parameter. Sites were advised to follow criteria for the initiation and termination of RRT (Bellomo et al. The Lancet 2012; 380:756-66.). Other renal endpoints included blood urea nitrogen (BUN) clearance, RRT-free days, renal function (ECC and estimated glomerular filtration rate (eGFR)) and MAKE composite scores at days 28 (RRT or death<28 days), 60 (eGFR<60 ml/min, or chronic RRT, or death<60 days), and 90 (eGFR<60 ml/min, or chronic RRT, or hospitalization for new episode of AKI, or death<90 days). See FIG. 3.

Safety, tolerability, pharmacokinetics (in the first 120 patients), immunogenicity, systemic and urinary biomarkers, and the effect of RecAP on quality of life in patients with SA-AKI were also investigated. A-priori subgroup analyses were planned to determine whether RecAP treatment demonstrates different levels of efficacy in specific patient groups. All endpoints, including non-safety and non-renal secondary end points are described in detail below.

Study Endpoints

Primary Endpoint: The primary endpoint was the area under the time-corrected endogenous creatinine-clearance (ECC) curve from Day 1 to Day 7 ($AUC_{1\text{-}7}$), calculated as the average of the standardized endogenous creatinine clearance values over the 7 days. Urine was collected for 5-7 hours and the ECC was calculated from the urine and serum creatinine concentration and urine volume. The ECC was determined daily from day 1 to day 7. The complete AUC was calculated and divided by 7 to produce a mean ECC.

Secondary Endpoints (a) Key Secondary Endpoint: The key secondary endpoint was RRT incidence during the period from day 1 (after first treatment) to day 28, inclusive.

(b) Other Secondary Endpoints:

Renal

Renal endpoints included the following:

Volume of urine (daily from day 1 to day 7, inclusive, and on subsequent visit days if reliable 6-hour urine collection was possible) normalized per hour.

Serum creatinine and BUN/urea (daily from day 1 to day 7, inclusive, and on subsequent visit days).

BUN/Urea clearance (daily from day 1 to day 7, inclusive, and on subsequent visit days if reliable urine collection was possible).

Peak value of serum creatinine and peak values of BUN/urea (during the period from day 1 to day 7, inclusive).

RRT-free days: Days alive and not dependent of RRT from randomization to day 28, inclusive. Support-free days were calculated as described here. In the Statistical Analysis Plan, support-free days were defined as 'a day on which a patient did not receive support' (RRT/mechanical ventilation/vasopressor/inotropic) in which the last observation was carried forward in case of death or withdrawal.

Total number of days on RRT (during the period from day 1 to day 28, inclusive). A day on RRT was defined as a day on which a patient received any form of RRT (including RRT with interruptions) for any period of time on that day.

Reasons for initiation of RRT (during the period from day 1 to day 28, inclusive).

Kidney function at days 14, 21, and 28 as assessed by measured creatinine clearance if available, otherwise as assessed by eGFR (estimated by the CKD-EPI formula based on serum creatinine concentration).

Kidney function at day 60 and day 90 as assessed by eGFR (estimated by the CKD-EPI formula based on serum creatinine concentration).

Sustained loss of kidney function at day 60 and day 90, defined by eGFR <60 mL/min (with eGFR estimated by the CKD-EPI formula based on serum creatinine concentration).

Incidence of dialysis dependency at day 60 and day 90.

Other Organs

Endpoints for organs other than kidney included the following:

Liver enzymes (aspartate aminotransferase [AST], alanine aminotransferase [ALT], gamma-glutamyl transpeptidase [GGT], lactate dehydrogenase [LDH], bilirubin) with the exception of AP.

Lung function as assessed by fraction partial pressure arterial oxygen ($PaO_2$)/fraction of inspired oxygen ($FiO_2$) (P/F ratio) Carrico index, positive end expiratory pressure (PEEP), and tidal volume in mechanically ventilated patients.

Mechanical ventilator-free days: Days alive and not dependent of mechanical ventilation from randomization to day 28, inclusive#. A ventilator-free day was defined as a day on which a patient was not on ventilator (invasive or non-invasive mechanical ventilation).

Time from start of first administration of study drug to being off mechanical ventilator (from day 1 to day 28, inclusive) for those patients who were on mechanical ventilator at the start of this period.

Shock-free days. Days alive and not dependent of vasopressor/inotropic therapy from randomization to day 28, inclusive. A patient was considered to be shock free if he or she was not on vasopressors or inotropic agents (including, but not limited to noradrenaline, adrenaline, dobutamine, dopamine, vasopressin, or enoximone). Support-free days were calculated as described here. In the Statistical Analysis Plan, support-free days were defined as 'a day on which a patient did not receive support' (RRT/mechanical ventilation/vasopressor/inotropic) in which the last observation was carried forward in case of death or withdrawal.

Time from start of first administration of treatment to being shock free (from day 1 to day 28, inclusive) for those patients who were not shock free at the start of this period.

Sequential organ failure assessment (SOFA) scores during ICU/intermediate care stay.

Number of dysfunctional organs as assessed by SOFA scores (from Baseline to day 28, inclusive).

Deaths during the 90-day study period (by recording date).

Biomarkers

Biomarker endpoints included the following:

Kidney function markers.

Tubular injury biomarkers.

Biomarkers for systemic inflammation.

Pharmacokinetics of RecAP in all three active treatment groups during Part 1 of the study.

In addition to RecAP PK concentration measurements, baseline (pre-dose) AP was measured by activity (central laboratory).

Other Endpoints

Additional endpoints included the following:

Three major adverse kidney events (MAKE) composite endpoints: patients who met, or did not meet, at least one of the following criteria:

MAKE composite endpoint 1: Received RRT or died (before day 28 [inclusive]).

MAKE composite endpoint 2: eGFR <60 mL/min at day 60 (estimated by the CKD-EPI formula); or dialysis dependency; or died (before day 60).

MAKE composite endpoint 3: eGFR <60 mL/min at day 90 (estimated by the CKD-EPI formula); or dialysis dependency; hospitalized for a new episode of AKI (at day 90), or died (before day 90).

Serology as assessed by immunoglobulin G (IgG), immunoglobulin E (IgE), and total immunoglobulin.

Safety parameters, including (serious) adverse events, laboratory assessments (clinical chemistry, hematology, and urinalysis parameters not considered in the efficacy analysis), vital signs, and ECG data.

Quality of life, assessed by EQ-5D questionnaire at baseline, ICU/intermediate care discharge, and day 90.

Time from start of first administration of treatment to discharge from ICU/intermediate care, where discharge was defined as the time when the decision was made to transfer the patient (as opposed to the time of actual transfer, that could be delayed due to placement issues).

Total time in ICU/intermediate care from the start of first administration of study drug (during the period Day 1 to Day 28 inclusive and during the period from day 1 to day 90, inclusive) using the time of actual transfer.

Time from start of first administration of treatment to discharge from hospital, where discharge was defined as the time when the decision was made to transfer the patient (as opposed to the time of actual transfer).

Total time in hospital from the start of first administration of study drug (during the period from day 1 to day 28, inclusive, and during the period day 1 to day 90, inclusive) using the time the decision was made to discharge the patient.

V. Statistical Analysis

Data were analyzed according to the intention-to-treat principle for patients from whom informed consent was obtained and who were randomized to a treatment arm. Details related to the sample size calculations are described below.

Sample Size Calculations

A sample size was planned of $n_1=30$ patients per treatment group in Part 1 with an additional $n_2=85$ patients recruited to the optimal RecAP-dose and placebo treatment groups in Part 2 (for a total sample size of n=290 patients). Custom-programmed simulations were performed using SAS software V.9.2 to determine power and type I error rate of the chosen sample size and design in a number of different dose-response scenarios. Each scenario assumed a standard deviation of 49 ml/min for the primary end point with an assumed response of 60 ml/min for the placebo group, and between 60 mL/min (no treatment effect) and 79 ml/min (strong treatment effect) for the RecAP dose groups.

Fifty thousand simulations were performed to show that the one-sided type I error rate is 2.4% (and hence is well controlled at the one-sided 2.5% significance level). The power was defined as the probability of rejecting the null hypothesis (of no difference between treatment groups) when one or more RecAP dose groups have a treatment effect, defined as a response of 69.5 ml/min. This was investigated across seven scenarios with 10 000 simulations performed for each. The chosen design achieved power of between 79% and 86% for scenarios with strong treatment effects for the medium and high RecAP dose groups; a varying response for the low-dose group, and between 66% and 67% when only the high-dose group had a strong treatment effect. As the sample size determination was based on the number of patients required for the intention-to-treat (ITT) analysis, patients who are randomly assigned and subsequently withdrew prior to completion of the study were not to be replaced.

A per-protocol analysis compared the intervention groups with the placebo group for patients who received study medication according to the study protocol, and had no more than two missing ECC values on days 1 through 7, as detailed in the statistical analysis plan.

For the descriptive statistics, continuous variables are presented as mean with standard deviation or median with interquartile range, depending on their distribution. Normally distributed variables were compared using Student's t test; Mann-Whitney U tests were used to compare non-normally distributed variables. Categorical (and binary) variables are presented as numbers with percentages and analyzed using chi-squared tests. Survival analyses with Kaplan-Meier curves were used for graphical presentation. Cox proportional-hazard regression analyses were used to estimate the hazard ratio for survival and for the number of RRT-, shock-, and mechanical ventilation-free days during study days 1-28 with the use of RecAP versus placebo.

The analysis of the primary efficacy endpoint was performed by an analysis of variance. All analyses performed on the secondary endpoints were for exploratory purposes only, therefore no multiplicity adjustment was required. A post-hoc multivariate analysis was conducted to establish the robustness of the RecAP effect. All statistical tests (SAS software version 9.4; SAS Institute Inc., Cary, NC, U.S.A.), performed on the intention-to-treat population, were two-sided using a 5% significance level.

Results

I. Participants

Of 326 patients who passed an initial screen, 301 patients were enrolled (FIG. 4) across 53 sites in 11 countries in the European Union and North America. Patients received RecAP 0.4 mg/kg, (n=30), 0.8 mg/kg, (n=32), 1.6 mg/kg (n=29 in Part 1 and n=82 in Part 2) or placebo (n=30 in Part 1 and n=86 in Part 2). Randomization resulted in well-balanced demographic and patient characteristics, except for slight baseline differences in renal function between groups (FIG. 5).

II. Efficacy Outcomes

In the dose-finding Part 1 of the trial, the median $AUC_{1-7}$ ECC was 47.0, 63.5, 60.7 ml/min in patients treated with RecAP 0.4, 0.8, 1.6 mg/kg, respectively, compared with 46.2 ml/min in the placebo group. See FIG. 7.

Following the interim analysis, the DSMB advised continuing the study with RecAP 1.6 mg/kg. As per the statistical analysis plan, only the effects of the RecAP 1.6 mg/kg group were compared with those of the placebo group in the primary analyses. When data from the RecAP 1.6 mg/kg groups from Parts 1 and 2 were combined (n=111), no significant difference was observed in the primary efficacy outcome ($AUC_{1-7}$ ECC) for RecAP treatment compared with placebo (n=116). Furthermore, the requirement of RRT was not significantly affected by RecAP treatment (FIG. 8).

As study drug infusion started as soon as possible following the AKI diagnosis, in less than half of the patients clearance data was obtained on day 0. In FIG. 9A and FIG. 9B, the difference in ECC and BUN clearance was calculated from day 1 onwards. Improvement of ECC (P=0.036) (FIG. 9A), as well as BUN clearance (P=0.033) (FIG. 9B), over 28 days was enhanced in RecAP-treated patients compared with those receiving placebo, based on differences that occurred from day 21 onwards.

Treatment with RecAP did not affect $MAKE_{28}$, but resulted in a significantly lower incidence of MAKE at day 60 (P=0.045) and day 90 (P=0.031) compared with placebo, (FIG. 8).

All-cause mortality by day 28 was statistically significantly lower in the RecAP group versus the placebo group (14.4% vs 26.7%, respectively; P=0.022). FIG. 10 shows mortality through to day 90 (favored treatment, P=0.030). A similar survival benefit was observed in the RecAP 0.8 mg/kg dose group. See FIG. 11, which presents a Kaplan Meier survival curve for all groups.

Inflammatory and renal injury biomarkers, as well as other non-renal endpoints were not significantly influenced by RecAP treatment. See FIG. 12 (table presenting primary and secondary endpoints for all groups) and FIGS. 13A to 31E.

Per protocol analyses yielded comparable results.

To test the robustness of the RecAP-mediated effect on survival, a post-hoc multivariate analysis was conducted, including Sequential Organ Failure Assessment (SOFA) subgroups and study arm as covariates. Treatment with RecAP remained significantly related to survival (hazard ratio 0.50, 95% CI 0.28-0.90; P=0.02; see FIG. 14).

III. Subgroup Analyses

No statistically significant effects on the primary endpoint and key secondary endpoint were observed in the a-priori defined subgroups. See FIGS. 15A to 15L. Baseline and day-1 ECC strongly correlated with $AUC_{1-7}$ ECC [r=0.88, common slope 1.023 (95% confidence interval [CI] 0.946-1.100); P<0.0001], indicating the relevance of initial renal function.

IV. Safety

Treatment emergent Serious Adverse Events were reported in 43% of patients that received RecAP 1.6 mg/kg and in 50% of patients that received placebo. See FIG. 16. No RecAP dose-dependency in the incidence and nature of Adverse Events (AE's) was observed. Anti-drug antibody titers were just above the detection limit in 9 patients treated with RecAP.

Discussion

In this multinational double-blind, randomized controlled trial involving patients with SA-AKI, we observed that addition of RecAP to standard of care had a large impact on survival, associated with an improved and sustained recovery of renal function and longer-term clinical outcomes, including composite MAKE endpoints. Because this was a dose-finding proof-of-principle phase 2 trial, it was designed to include endpoints related to both renal dysfunction (e.g. short-term ECC) and the long-term, more patient-centered, clinical outcomes (e.g. $MAKE_{day60-90}$, survival).

Function is a competing endpoint with death and may therefore differ from clinical outcome (Billings et al. Nephron Clinical practice 2014; 127:89-93). In the current study, no penalty for death on functional measures was used, so separation of survival curves makes it harder to account for function in non-survivors, which may explain the discrepancy between the short- and longer-term therapeutic efficacy observed.

In sepsis, injury is known to be heterogeneous throughout the kidney with patchy tubular damage being the most common histological finding (Kellum et al. Nat Rev Nephrol 2018). By contrast, renal function is a global measure. Consequently, acute measures of organ function may belie underlying organ damage that only becomes evident later. RecAP reduced kidney damage and facilitated organ function could manifest after weeks. Several additional reasons are plausible for the observed RecAP on short-term ECC and its positive effects on the longer-term clinical outcomes. First, creatinine and its clearance are recognized to be of limited precision to estimate renal function (Shemesh et al. Kidney International 1985; 28:830-8; Perrone et al. Clin Chem 1992; 38:1933-53), however no feasible alternative is currently available. Second, despite randomization, there was a slight imbalance in renal function between groups. Previous work (Kellum et al. Am J Respir Crit Care Med 2017; 195:784-91), as well as the current trial, illustrates that the degree of initial renal dysfunction dictates the extent of renal recovery and survival, as more severe kidney failure correlates with worse outcomes. Therefore, the somewhat more impaired renal function may account for the absence of an improvement of ECC in the first week. Third, statistically significant differences in recovery of ECC between treatment groups emerged from day 21 onwards. Fourth, the significantly higher survival rate in the RecAP-treated group likely affected the primary and key secondary outcomes, as poor renal function in the most severely ill, but surviving, patients in the treatment group may have attenuated the ECC. Of interest, the survival benefit in the treatment arm did not negatively affect any of the other endpoints, such as quality of life. To further explore the robustness of the effect of RecAP on survival we performed a post-hoc multivariate analysis including SOFA-subgroups, known to influence survival. In this analysis, randomization to the treatment arm remained a strong predictor of survival.

In the current larger trial, we evaluated a human recombinant AP that is suitable for widespread clinical use. It remains unclear to what extent renal protection is mediated through direct effects on tubular cells or systemic effects indirectly prevent damage to the kidneys, or whether kidney function improves as general effect of improving sepsis. On one hand, AP is depleted in the kidney following an ischemic insult (Khundmiri et al. Am J Physiol 1997; 273:849-56), and RecAP attenuates the inflammatory response in isolated human proximal tubule cells (Peters et al. Br J Pharmacol 2015; 172:4932-45). On the other hand, systemic detoxifying properties may lead to more swift normalization of circulating inflammatory markers (Pickkers et al. Crit Care 2012; 16:R14) indirectly benefiting the kidneys. It appears that direct effects on renal tissue are important. Treatment with RecAP can attenuate renal inflammation and thereby influences its detrimental long-term effects, and/or RecAP may possibly enhance renal recovery from AKI opposed to prevention of the primary injury itself.

In conclusion, RecAP therapy was considered safe and well-tolerated. In sepsis patients with AKI, RecAP treatment was observed to provide significant improvements of longer-term renal function, $MAKE_{60-90}$, and survival.

A post-hoc analysis in which patients were stratified according to the severity of kidney disease defined according to baseline ECC or baseline eGFR revealed distinct effects resulting from the administration of RecAP to patients with moderate to severe injury and for patients with severe kidney injury. See FIG. 17. Mild SA-AKI did not increase mortality in patients, and administration of AP appears to have had no effect on the survival of that population. The same was observed on the moderate to severe SA-AKI group. Surprisingly, patients that presented with a baseline eGFR <60 ml/min benefit from AP administration with regard to mortality similarly as the ECC <15 ml/min group. See FIG. 22. On the other hand, individuals with severe SA-AKI (as determined by ECC <15 ml/min) treated with AP had a survival rate comparable to both AP treated or placebo treated moderate to severe injury and mild injury groups. In contrast, SA-AKI patients treated with placebo has a much lower survival rate. The treatment of patients with several SA-AKI with 1000 U/kg doses of RecAP during three days after the onset of sepsis resulted in a dramatic survival increase (>20%) up to 90 days after treatment. Furthermore, statistically significant increases in kidney function (increased creatinine clearance) were observed in the moderate to severe SA-AKI at days 21 and 28 after treatment. An increase in kidney function was observed the severe SA-AKI group. See also FIGS. 18, 19 and 20. The model fit statistics presented in FIG. 18 such as R squared and Log likelihood Ratio (LR) test demonstrate a comparable but slightly better fit for the continuous model (Model 1) compared to the categorical model (Model 2) with one less parameter; the categorical model however provides however coefficients that are interpretable as hazard ratios (HR).

Example 2

Determination of RecAP Enzyme Activity and Protein Concentration

Activity Assay:

Determination of recAP enzyme activity was based on the conversion (hydrolysis) of 4-nitrophenolphosphate into 4-nitrophenol which is colored yellow. The change in optical density at 405 nm per unit time is a measure for the alkaline phosphatase activity. The assay buffer consisted of 0.25M Glycine buffer pH 9.6 at 25° C. with 2 mM $MgCl_2$ and 0.1 mM $ZnCl_2$ and 8.5 mM 4-nitrophenolphosphate.

The unit (U) definition for recAP, expressed as U/mL, is the amount of enzyme causing the hydrolysis of 1 μmol of 4-nitrophenolphosphate per minute at pH 9.6 and 25° C.

Protein Concentration:

Determination of total protein concentration in RecAP Drug Substance and Drug Product was performed by UV/Vis analysis. A RecAP solution is analysed at 280 nm and the absorbance is a measure for protein content (mg/mL) using the formula:

Concentration (mg/mL)=[$A/(a \times b)$]×$DF$ with $A=A280$; $b$=path length; $a$=mass extinction coefficient of 1.01 mL mg-1 cm-1; DF is dilution factor.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method to treat sepsis-associated acute kidney disease injury (SA-AKI) in a subject in need thereof comprising administering an effective amount of alkaline phosphatase (AP) to the subject, wherein
   (i) the subject has an ECC (endogenous creatinine clearance) rate 15-60 ml/min prior to the treatment with AP or an eGFR (estimated glomerular filtration rate) 15-60 ml/min prior to the treatment with AP,
   (ii) the AP is administered in at least one 500 U/kg to 2,000 U/kg dose, and
   (iii) the administration of the AP results in an increase in renal function,
   wherein the AP is a chimeric AP having 100% sequence identity to the amino acid sequence of SEQ ID NO: 1.

2. The method of claim 1, wherein the AP is a human AP.

3. The method of claim 1, wherein the increase in renal function comprises an increase in ECC with respect to ECC in the absence of treatment or an increase in eGFR with respect to eGFR in the absence of treatment.

4. The method of claim 1, wherein sepsis is detected less than 96 hours prior to AP administration.

5. The method of claim 1, wherein the sepsis is detected less than 72 hours prior to SA-AKI detection.

6. The method of claim 1, wherein treatment is initiated within 24 hours after sepsis is detected.

7. The method of claim 1, wherein treatment is initiated within 24 hours after SA-AKI is detected.

8. The method of claim 1, wherein AP is administered once daily.

9. The method of claim 1, wherein AP is administered intravenously.

10. The method of claim 1, wherein AP is administered in three daily doses.

11. The method of claim 1, wherein the AP dose is 0.8 mg/kg or 1.6 mg/kg.

12. The method of claim 1, wherein the AP dose is 500 U/kg or 1000 U/kg.

13. The method of claim 1, wherein the administration of at least one dose of AP results in the preservation or increase of glomerular filtration rate (GFR) or eGFR in the subject.

* * * * *

SEQUENCE LISTING

```
<160> NUMBER OF SEQ ID NOS: 1

<210> SEQ ID NO 1
<211> LENGTH: 484
<212> TYPE: PRT
<213> ORGANISM: Homo sapiens

<400> SEQUENCE: 1

Val Ile Pro Ala Glu Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
            20                  25                  30

Ala Lys Asn Leu Ile Leu Phe Leu Gly Asp Gly Leu Gly Val Pro Thr
        35                  40                  45

Val Thr Ala Thr Arg Ile Leu Lys Gly Gln Lys Asn Gly Lys Leu Gly
    50                  55                  60

Pro Glu Thr Pro Leu Ala Met Asp Arg Phe Pro Tyr Leu Ala Leu Ser
65                  70                  75                  80

Lys Thr Tyr Asn Val Asp Arg Gln Val Pro Asp Ser Ala Ala Thr Ala
                85                  90                  95

Thr Ala Tyr Leu Cys Gly Val Lys Ala Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Gln Ala Gly Lys Ser Val Gly
    130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205
```

```
Pro Met Gly Thr Pro Asp Pro Glu Tyr Pro Ala Asp Ala Ser Gln Asn
    210             215                 220

Gly Ile Arg Leu Asp Gly Lys Asn Leu Val Gln Glu Trp Leu Ala Lys
225             230                 235                 240

His Gln Gly Ala Trp Tyr Val Trp Asn Arg Thr Glu Leu Met Gln Ala
                245                 250                 255

Ser Leu Asp Gln Ser Val Thr His Leu Met Gly Leu Phe Glu Pro Gly
                260                 265                 270

Asp Thr Lys Tyr Glu Ile Leu Arg Asp Pro Thr Leu Asp Pro Ser Leu
            275                 280                 285

Met Glu Met Thr Glu Ala Ala Leu Arg Leu Leu Ser Arg Asn Pro Arg
            290                 295                 300

Gly Phe Tyr Leu Phe Val Glu Gly Gly Arg Ile Asp His Gly His His
305             310                 315                 320

Glu Gly Val Ala Tyr Gln Ala Val Thr Glu Ala Val Met Phe Asp Asp
                325                 330                 335

Ala Ile Glu Arg Ala Gly Gln Leu Thr Ser Glu Glu Asp Thr Leu Thr
                340                 345                 350

Leu Val Thr Ala Asp His Ser His Val Phe Ser Phe Gly Gly Tyr Pro
            355                 360                 365

Leu Arg Gly Ser Ser Ile Phe Gly Leu Ala Pro Gly Lys Ala Arg Asp
370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
                405                 410                 415

Pro Glu Tyr Arg Gln Gln Ser Ala Val Pro Leu Asp Glu Glu Thr His
                420                 425                 430

Gly Gly Glu Asp Val Ala Val Phe Ala Arg Gly Pro Gln Ala His Leu
            435                 440                 445

Val His Gly Val Gln Glu Gln Ser Phe Val Ala His Val Met Ala Phe
    450                 455                 460

Ala Ala Cys Leu Glu Pro Tyr Thr Ala Cys Asp Leu Ala Leu Pro Ala
465                 470                 475                 480

Cys Thr Thr Asp
```